US009896695B2

(12) United States Patent
Chan et al.

(10) Patent No.: US 9,896,695 B2
(45) Date of Patent: Feb. 20, 2018

(54) HAHB11 PROVIDES IMPROVED PLANT YIELD AND TOLERANCE TO ABIOTIC STRESS

(71) Applicants: Raquel Lia Chan, Santa Fe (AR); Julieta Virginia Cabello, Santa Fe (AR); Jorge Ignacio Giacomelli, Santa Fe (AR); Universidad Nacional del Litoral (UNL), Santa Fe (AR)

(72) Inventors: Raquel Lia Chan, Santa Fe (AR); Julieta Virginia Cabello, Santa Fe (AR); Jorge Ignacio Giacomelli, Santa Fe (AR)

(73) Assignees: Consejo Nacional de Investigaciones Cientificas y Tecnicas (CONICET), Caba, Buenos Aires (AR); Universidad Nacional del Litoral (UNL), Santa Fe (AR)

( * ) Notice: Subject to any disclaimer, the term of this patent is extended or adjusted under 35 U.S.C. 154(b) by 287 days.

(21) Appl. No.: 14/376,411

(22) PCT Filed: Feb. 1, 2013

(86) PCT No.: PCT/US2013/024473
§ 371 (c)(1),
(2) Date: Jul. 20, 2015

(87) PCT Pub. No.: WO2013/116750
PCT Pub. Date: Aug. 8, 2013

(65) Prior Publication Data
US 2016/0002660 A1 Jan. 7, 2016

Related U.S. Application Data

(60) Provisional application No. 61/594,133, filed on Feb. 2, 2012.

(51) Int. Cl.
*A01H 5/00* (2006.01)
*C12N 15/82* (2006.01)
*C07K 14/415* (2006.01)
*A01H 1/00* (2006.01)
*C12N 15/00* (2006.01)

(52) U.S. Cl.
CPC ........ *C12N 15/8273* (2013.01); *C07K 14/415* (2013.01); *C12N 15/8261* (2013.01); *C12N 15/8271* (2013.01)

(58) Field of Classification Search
None
See application file for complete search history.

(56) References Cited

U.S. PATENT DOCUMENTS

2009/0144847 A1 6/2009 Shaikh et al.
2010/0192252 A1 7/2010 Chan et al.
2011/0030092 A1 2/2011 Portereiko et al.

FOREIGN PATENT DOCUMENTS

WO WO/2013/116750 8/2013

OTHER PUBLICATIONS

Michelmore et al., EST Database, Acc. No. DY923855, Oct. 5, 2006, see Result 1.*
Arce A.L., et al., "Uncharacterized conserved motifs outside the HD-Zip domain in HD-Zip subfamily I transcription factors; a potential source of functional diversity," BMC Plant Biol. 11:42, 19 pages, BioMed Central, England (2011).
Ariel F., et al., "Environmental Regulation of Lateral Root Emergence in Medicago truncatula Requires the HD-Zip I Transcription Factor HB1," Plant Cell 22:2171-2183, American Society of Plant Biologists, United States (2010).
Ariel F.D., et al., "The true story of the HD-Zip family," Trends Plant Sci. 12:419-426, Elsevier Ltd., England (2007).
Cabello J.V., et al., "The homologous HD-Zip I transcription factors HaHB1 and AtHB13 confer cold tolerance via the induction of chitinase and glucanase proteins," The Plant Journal 69:141-153, Blackwell Publishing Ltd., England(201 1).
Carles C., et al., "Regulation of *Arabidopsis thaliana* Em Genes:Role ofAB15," Plant J. 30:373-383, Blackwell Science Ltd., England (2002).
Chan R.L., et al., "Homeoboxes in plant development," Biochim. Biophys. Acta 1442:1-19, Elsevier Science B.V., Netherlands (1998).
Clough S.J. and Bent A.F., "Floral dip: a simplified method for Agrobacterium-mediated transformation of *Arabidopsis thaliana*," Plant J. 16:735-743, Blackwell Science Ltd., England (1998).
Dezar C.A., et al., "The promoter of the sunflower HD-Zip protein gene Hahb4 directs tissue-specific expression and is inducible by water stress, high salt concentrations and ABA," Plant Sci. 169:447-459, Elsevier Ireland Ltd., Ireland (2005).
Dezar C.A., et al., "Hahb-4, a sunflower homeobox-leucine zipper gene, is a developmental regulator and confers drought tolerance to *Arabidopsis thaliana* plants," Transgenic Res. 14:429-440, Springer, England (2005).
Easterling, W.E., "Climate change and the adequacy of food and timber in the 21st century," PNAS 104:19679, National Academy of Sciences , United States (2007).
Drew M.C. and Sisworo E.J., "Early effects of flooding on nitrogen deficiency and leaf chlorosis in barley," New Phytol. 79:567-571 (1977).

(Continued)

*Primary Examiner* — Phoenix Bui
(74) *Attorney, Agent, or Firm* — Sterne, Kessler, Goldstein & Fox P.L.L.C.

(57) ABSTRACT

The present invention provides isolated HaHB11 polypeptides and nucleic acids encoding the same. Also provided are methods of introducing a nucleic acid encoding HaHB11 polypeptides into a plant cell, plant part or plant, e.g., to increase tolerance to abiotic stress, to delay development and/or prolong the life span of a plant, and/or to increase yield from the plant. The invention also provides nucleic acids comprising HaHB11 promoter sequences and methods for expressing a nucleotide sequence of interest operably associated with the HaHB11 promoters of the invention in a plant cell, plant part, or plant. Also provided are transformed plants, plant tissues, plant cells and plant seed comprising the nucleic acids, expression cassettes and vectors of the invention.

7 Claims, 37 Drawing Sheets

(56) References Cited

OTHER PUBLICATIONS

Fukao T., et al., "The Submergence Tolerance Regulator SUB IA Mediates Crosstalk Between Submergence and Drought Tolerance in Rice," Plant Cell 23:412-427, American Society of Plant Biologists, United States (2011).

Gago, G.M., et al., "Hahb-4, a homeobox-leucine zipper gene potentially involved in abscisic acid-dependent responses to water stress in sunflower," Plant Cell Environ. 25, 633-640, Blackwell Science Ltd., England (2002).

Henriksson E., et al., "Homeodomain Leucine Zipper Class I Genes in *Arabidopsis*. Expression Patterns and Phylogenetic Relationships," Plant Physiol. 139:509-518, American Society of Plant Biologists, United States (2005).

Hirayama T. and Shinozald K. "Perception and Transduction of Abscisic Acid Signals:Keys to the Function of the Versatile Plant Hormone ABA," Trends in Plant Science, Elsevier Ltd., England (2007).

Jefferson, R.A., et al., "GUS fusions: β-glucuronidase as a sensitive and versatile gene fusion marker in higher plants," EMBO J. 6:3901-3907, IRL Press Limited, England (1987).

Kyu Hong J., et al., "Function of a Novel GDSL-type Pepper Lipase Gene, CaGLIP1, in Disease Susceptibility and Abiotic Stress Tolerance," Planta 227:539-558, Springer-Verlag, Germany (2008).

Liu Q., et al., "Two Transcription Factors, DREB1 and DREB2, with an EREBP/AP2 DNA Binding Domain Separate two Cellular Signal Transduction Pathways in Drought-and Low-Temperature-Responsive Gene Expression, respectively, in *Arabidopsis*," Plant Cell 10:1391-1406, American Society of Plant Physiologists, United States (1998).

Lopez-Molina L., et al., "A Postgermination Developmental Arrest Checkpoint is Mediated by Abscisic Acid and Requires the AB15 Transcription Factor in *Arabidopsis*," PNAS 98:4782-4787, National Academy of Sciences, United States (2001).

Manfre A.J., et al., "The *Arabidopsis* Group 1 Late Embryogenesis Abundant Protein ATEM6 Is Required for Normal Seed Development," Plant Physiol. 140:140-149, American Society of Plant Biologists, United States (2006).

Manavella, P.A., et al., "Cross-talk between ethylene and drought signaling pathways is mediated by the sunflower Hahb-4 transcription factor," Plant. J. 48:125-137, Blackwell Publishing Ltd., England (2006).

Manavella, P.A. and Chan, R.L., "Transient transformation of sunflower leaf discs via an Agrobacterium-mediated method: applications for gene expression and silencing studies," Nat. Protoc. 4:1699-1707, Nature Publishing Group, England (2009).

Manavella P.A., et al., "The sunflower HD-Zip transcription factor HAHB4 is up regulated in darkness acting as a repressor of photosynthesis related genes transcription," J Exp. Bot. 59:3143-3155, Oxford University Press, England (2008).

Manavella P.A., et al., "HAHB4, a sunflower HD-Zip protein, integrates signals from the jasmonic acid and ethylene pathways during wounding and biotic stress responses," Plant J. 56:376-388, Blackwell Publishing Ltd., England (2008).

Manavella PA, et al., "Two ABREs, two redundant root-specific and one W-box cis-acting elements are functional in the sunflower HAHB4 promoter," Plant. Physiol. Biochem. 46:860-867, Elsevier Masson SAS, France (2008).

Mitsuda N. and Ohme-Tagaki M., "Functional Analysis of Transcription Factors in *Arabidopsis*," Plant and Cell Physiology 50:1232-1248, Japanese Society of Plant Physiologists, Japan (2009).

Nakashima K. and Yamaguchi-Shinozaki K., "Molecular Studies on Stress-Responsive Gene Expression in *Arabidopsis* and Improvement of Stress Tolerance in Crop Plants by Regulon Biotechnology," Japan Agricultural Research Quarterly 39:221-229 (2005).

Olsson A.S., et al., "The Homeobox Genes Athb12 and Athb7 Encode Potential Regulators of Growth in Response to Water Deficit in *Arabidopsis*," Plant Mol. Biol. 55:663-677, Kulwer Academic Publishers, Netherlands (2004).

Schena, M. and Davis, R.W., "HD-Zip protein members of *Arabidopsis* homeodomain protein superfamily," Proc. Natl Acad. Sci. USA 89:3894-3898 National Academy of Sciences, United States (1992).

Thomashow M.F., "So what's New in the Field of Plant Cold Acclimation? Lots!" Plant Physiol. 125:89-93, American Society of Plant Biologists, United States (2001).

Visser E.J.W, et al., "Flooding and Plant Growth," Ann. Bot. 91:107-109, Annals of Botany Company, England (2003).

Whatley F.R., et al., "Separation of the Light and Dark Reactions in Electron Transfer during Photosynthesis," Proc. Natl Acad. Sci. USA 49:266-270, National Academy of Sciences, United States (1963).

Xu K., et al., "Sub1A is an ethylene-response—factor-like gene that confers submergence tolerance to rice," Nature 10:705-708, Nature Publishing Group, England (2006).

Yamaguchi-Shinozaki K. and Shinozaki K., "A Novel cis-Acting Element in an *Arabidopsis* Gene is Involved in Responsiveness to Drought, Low-Temperature, or High Salt Stress," Plant Cell 6:251-264, American Society of Plant Physiologists, United States (1994).

Zou X., et al., "Identification of transcriptome induced in roots of maize seedlings at the late stage of waterlogging," BMC Plant Biol. 10:189-215, BioMed Central, England (2010).

Cabello, J.V., et al., "The intron of the *Arabidopsis thaliana* COX5c gene is able to improve the drought tolerance conferred by the sunflower Hahb-4 transcription factor," Planta 226:1143-1154, Springer-Verlag, Germany (2007).

GenBank Report, "Sunflower HA89 ESTs from the Compositae Genome Project," Accession No. GE515297, accessed at http://www.ncbi.nlm.nih.gov/nucest/GE515297, 1 page, Nov. 2008.

GenBank Report, "Sunflower (*Helianthus annuus*) ESTs (set 2) from the Compositae Genome Project," Accession No. DY923855, accessed at http://www.ncbi.nlm.nih.gov/nucest/90461976?report=genbank, 1 page, Oct. 2006.

* cited by examiner

FIG. 1A — SCHEMATIC REPRESENTATION OF THE SUNFLOWER HAHB11 GENE

FIG. 2A

```
HAHB11.1
HAHB11.2

HAHB11.1
HAHB11.2

HAHB11.1
HAHB11.2

HAHB11.1
HAHB11.2
```

FIG. 2B

```
Helianthus annuus HaHB11.1   MAEN...---...
Helianthus annuus HaHB11.2   MAEN...
Helianthus tuberosus 1       MAE...
Helianthus agrophyllus       MAE...---...
Helianthus ciliaris          MAE...---...
Helianthus tuberosus 2       -LRRGRNVVREEED...
Helianthus tuberosus 3       --RGAER...

Helianthus annuus HaHB11.1
Helianthus annuus HaHB11.2
Helianthus tuberosus 1
Helianthus agrophyllus
Helianthus ciliaris
Helianthus tuberosus 2
Helianthus tuberosus 3

Helianthus annuus HaHB11.1   ...-------...---...
Helianthus annuus HaHB11.2   ...-------...
Helianthus tuberosus 1       ...-------...
Helianthus agrophyllus       ...-------...
Helianthus ciliaris          ...-------...
Helianthus tuberosus 2       ...DMAIYSD......-----...
Helianthus tuberosus 3       ...DMAIYS...-...

Helianthus annuus HaHB11.1
Helianthus annuus HaHB11.2
Helianthus tuberosus 1
Helianthus agrophyllus
Helianthus ciliaris
Helianthus tuberosus 2
Helianthus tuberosus 3
```

FIG. 2C

HAHB11 PROVIDES IMPROVED PLANT YIELD AND TOLERANCE TO ABIOTIC STRESS

This application is a 371 of international application PCT/US2013/024473, filed Feb. 1, 2013, which claims priority to and benefit of U.S. Provisional Application No. 61/594,133, filed Feb. 2, 2012. The disclosures of these prior applications are incorporated in their entirety herein by reference thereto.

The content of the electronically submitted sequence listing (Name: 3181_0040001_SeqListing.txt, Size: 22 kilobytes; and Date of Creation: Sep. 18, 2015) is identical to the sequence information in the computer readable form of prior International Patent Application No. PCI/US2013/024473, and is herein incorporated by reference in its entirety.

FIELD OF THE INVENTION

The present invention relates to the field of plant molecular biology, more particularly to methods of expressing nucleic acids in plants.

BACKGROUND OF THE INVENTION

Global climate change influences the frequency and magnitude of hydrological fluctuations, causing devastating events such as floods and drought. These events, generating stress to plants, are the primary cause of crop loss worldwide, causing average yield losses of more than 50% for major crops. Drought is the major factor that globally limits crop productivity, and flooding represents another severe constraint that limits crop growth and productivity. Both high and low extremes in precipitation increasingly limit food, fiber and forest production worldwide (Easterling et al., PNAS. 104:19679 (2007)).

Progress has been made in plant transformation for enhanced abiotic stress tolerance through manipulation of either transcription and/or signaling factors during the last two decades. However, none of these transformed crops has yet been marketed.

Transcription factors (TFs) regulate gene expression in response to environmental stresses. Bioinformatics studies have indicated that *Arabidopsis* has around 2000 genes encoding TFs (Riechmann et al., Science 290:2105-2110 (2000); and Mitsuda et al., Plant and Cell Phys. 50:1232-1248 (2009)), which are classified into different families according to the structure of their binding domains as follows: NAC, DOF, WRKY, bZIP, ERF/AP2, MYB, Zn-finger and homeodomain (HD). HD is a 60 amino acid DNA-binding domain that is present in TFs across all eukaryotic organisms, and which is encoded by a 180 bp sequence designated as Homeobox (HB). In plants, HD proteins are divided into different families, for example, HD-Zip, PHD finger, Bell, ZF-HD, WOX and KNOX (Chan et al., Biochim. Biophys. Acta 1442:1-19 (1998); Ariel et al., Trends Plant Sci. 12:419-426 (2007)). Members of the HD-Zip family exhibit an association of a HD and a downstream leucine zipper motif (LZ). This association in a single protein is unique to plants (Schena et al., PNAS 89, 3894-3898 (1992)). HD-Zip proteins can be divided into four subfamilies, named I to IV, according to several structural and functional features.

SUMMARY OF THE INVENTION

The invention encompasses HaHB11 related compositions and their use. HaHB11.1 encodes a 175 amino acid protein, initially identified in *Helianthus annuus*, belonging to the HD-Zip family of transcription factors. HaHB11.2 encodes a 181 amino acid protein, initially identified in *Helianthus annuus*, belonging to the HD-Zip family of transcription factors. Recently, phylogenetic trees constructed with proteins from several species resolved HD-Zip I members in six groups according to the conservation within and outside of the HD-Zip domain (Arce et al., BMC Plant Biol. 11:42 (2011)). Neither HaHB11 nor the well-characterized HaHB4 transcription factor (Gago et al., Plant Cell Environ. 25:633-640 (2002); Dezar et al., Transgenic Res. 14:429-440 (2005), Dezar et al., Plant Sci. 169:447-459 (2005); Manavella et al., Plant J. 48:125-137 (2006); Cabello et al., 2007; Manavella et al., Plant Physiol. Biochem. 46:860-867 (2008), Manavella et al., Plant J. 56:376-388 (2008), and Manavella et al., J. Exp. Bot. 59: 3143-3155 (2008)) were resolved into any of these six groupings, indicating that they are divergent members and probably possess differential functions (Arce et al., BMC Plant Biol. 11:42 (2011)).

The inventors have found that HaHB11 provides increased tolerance to abiotic stress and has dual functionality, participating in both drought and flooding tolerances. The inventors have also found that HaHB11 provides increased salinity tolerance. Transgenic plants expressing HaHB11 exhibit longer roots. Moreover, transgenic plants expressing HaHB11 exhibit larger rosettes and improved yield as compared with controls under normal growth conditions (e.g., normal irrigation and no salt stress) and conditions of abiotic stress.

Accordingly, as a first aspect, the invention provides a transgenic plant stably transformed with an isolated nucleic acid encoding a polypeptide selected from the group consisting of:

(a) a polypeptide comprising (i) a HD-Zip domain that binds CAAT(A/T)ATTG (SEQ ID NO:7) and (ii) amino acids 111 to 175 of SEQ ID NO:3; and (b) a polypeptide comprising (i) a HD-Zip domain that binds CAAT(A/T)ATTG (SEQ ID NO:7) and (ii) an amino acid sequence that is at least about 70% similar to amino acids 111 to 175 of SEQ ID NO:3.

In some embodiments, the invention provides a transgenic plant stably transformed with an isolated nucleic acid encoding a polypeptide selected from the group consisting of:

(a) a polypeptide comprising (i) a HD-Zip domain that binds CAAT(A/T)ATTG (SEQ ID NO:7) and (ii) amino acids 114 to 181 of SEQ ID NO:10; and (b) a polypeptide comprising (i) a HD-Zip domain that binds CAAT(A/T)ATTG (SEQ ID NO:7) and (ii) an amino acid sequence that is at least about 96% similar or at least 96%, 97%, 98% or 99% identical to amino acids 114 to 181 of SEQ ID NO:10.

In some embodiments, the invention provides a transgenic plant stably transformed with an isolated nucleic acid encoding a polypeptide selected from the group consisting of:

(a) a polypeptide comprising (i) a HD-Zip domain that binds CAAT(A/T)ATTG (SEQ ID NO:7) and (ii) amino acids 115 to 113 of SEQ ID NO:10; and (b) a polypeptide comprising (i) a HD-Zip domain that binds CAAT(A/T)ATTG (SEQ ID NO:7) and (ii) an amino acid sequence that is at least about at least 96%, 97%, 98% or 99% identical to amino acids 15 to 181 of SEQ ID NO:10.

In some embodiments, the invention provides a transgenic plant stably transformed with an isolated nucleic acid encoding a polypeptide selected from the group consisting of:

(a) a polypeptide comprising (i) a HD-Zip domain that binds CAAT(A/T)ATTG (SEQ ID NO:7) and (ii) amino acids 114 to 180 of SEQ ID NO:11, amino acids 111 to 179 of SEQ ID NO:12; amino acids 111 to 177 of SEQ ID NO:13, amino acids 113 to 183 of SEQ ID NO:14 or amino acids 112 to 186 of SEQ ID NO:15;

(b) a polypeptide comprising (i) a HD-Zip domain that binds CAAT(A/T)ATTG (SEQ ID NO:7) and (ii) an amino acid sequence that is at least about 96% similar or at least 96%, 97%, 98% or 99% identical to amino acids amino acids 114 to 180 of SEQ ID NO:11, amino acids 111 to 179 of SEQ ID NO:12; amino acids 111 to 177 of SEQ ID NO:13, amino acids 113 to 183 of SEQ ID NO:14, or amino acids 112 to 186 of SEQ ID NO:15.

In representative embodiments, the transgenic plant has an increased tolerance to abiotic stress and/or increased yield.

As a further aspect, the invention provides a transgenic plant stably transformed with an isolated nucleic acid comprising a nucleotide sequence selected from the group consisting of:

(a) the nucleotide sequence of SEQ ID NO:2;

(b) a nucleotide sequence comprising at least 100 consecutive nucleotides of the nucleotide sequence of SEQ ID NO:2;

(c) a nucleotide sequence having at least 95% sequence identity to the nucleotide sequence of (a) or (b);

(d) a nucleotide sequence that hybridizes to the complete complement of the nucleotide sequence of (a) or (b) under stringent hybridization conditions; and (e) a nucleotide sequence that differs from the nucleotide sequence of any of (a) to (d) due to the degeneracy of the genetic code.

In some embodiments, the invention provides a transgenic plant stably transformed with an isolated nucleic acid comprising a nucleotide sequence selected from the group consisting of:

(a) the nucleotide sequence of SEQ ID NO:9;

(b) a nucleotide sequence having at least 96% sequence identity to the nucleotide sequence of (a); and (c) a nucleotide sequence that differs from the nucleotide sequence of any of (a) or (b) due to the degeneracy of the genetic code.

In representative embodiments, the transgenic plant has an increased tolerance to abiotic stress and/or increased yield.

As yet another aspect, the invention provides a method of increasing yield and/or increasing tolerance of a plant to abiotic stress, the method comprising:

(a) stably transforming a plant cell with an isolated nucleic acid encoding a polypeptide selected from the group consisting of:

(i) a polypeptide comprising (a) a HD-Zip domain that binds CAAT(A/T)ATTG (SEQ ID NO:7) and (b) amino acids 111 to 175 of SEQ ID NO:3; and (ii) a polypeptide comprising (a) a HD-Zip domain that binds CAAT(A/T)ATTG (SEQ ID NO:7 and (b) an amino acid sequence that is at least about 70% similar to amino acids 111 to 175 of SEQ ID NO:3.

In some embodiments, the invention provides a method of increasing yield and/or increasing tolerance of a plant to abiotic stress, the method comprising:

(a) stably transforming a plant cell with an isolated nucleic acid encoding a polypeptide selected from the group consisting of:

(i) a polypeptide comprising (a) a HD-Zip domain that binds CAAT(A/T)ATTG (SEQ ID NO:7) and (b) amino acids 114-181 of SEQ ID NO:10; and (ii) a polypeptide comprising (a) a HD-Zip domain that binds CAAT(A/T)ATTG (SEQ ID NO:7) and (b) an amino acid sequence that is at least about that is at least about 96% similar or at least 96%, 97%, 98% or 99% identical to amino acids 114 to 180 of SEQ ID NO:10.

In some embodiments, the invention provides a method of increasing yield and/or increasing tolerance of a plant to abiotic stress, the method comprising:

(a) stably transforming a plant cell with an isolated nucleic acid encoding a polypeptide selected from the group consisting of:

(i) a polypeptide comprising (a) a HD-Zip domain that binds CAAT(A/T)ATTG (SEQ ID NO:7) and (b) amino acids 114 to 180 of SEQ ID NO:11, amino acids 111 to 179 of SEQ ID NO:12; amino acids 111 to 177 of SEQ ID NO:13, amino acids 113 to 183 of SEQ ID NO:14, or amino acids 112 to 186 of SEQ ID NO:15; and (ii) a polypeptide comprising (a) a HD-Zip domain that binds CAAT(A/T)ATTG (SEQ ID NO:7) and (b) an amino acid sequence that is at least about that is at least about 96% similar or at least 96%, 97%, 98% or 99% identical to amino acids 114 to 180 of SEQ ID NO:11, amino acids 111 to 179 of SEQ ID NO:12; amino acids 111 to 177 of SEQ ID NO:13, amino acids 113 to 183 of SEQ ID NO:14, or amino acids 112 to 186 of SEQ ID NO:15.

Still further, the invention provides a method of increasing yield and/or increasing tolerance of a plant to abiotic stress, the method comprising:

(a) stably transforming a plant cell with an isolated nucleic acid comprising a nucleotide sequence selected from the group consisting of:

(i) the nucleotide sequence of SEQ ID NO:2;

(ii) a nucleotide sequence comprising at least 100 consecutive nucleotides of the nucleotide sequence of SEQ ID NO:2;

(iii) a nucleotide sequence having at least 95% sequence identity to the nucleotide sequence of (i) or (ii);

(iv) a nucleotide sequence that hybridizes to the complete complement of the nucleotide sequence of (i) or (ii) under stringent hybridization conditions; and (v) a nucleotide sequence that differs from the nucleotide sequence of any of (i) to (iv) due to the degeneracy of the genetic code.

(b) regenerating a stably transformed plant from the stably transformed plant cell of (a); and (c) expressing the nucleotide sequence in the plant.

In additional embodiments, the invention provides a method of increasing yield and/or increasing tolerance of a plant to abiotic stress, the method comprising:

(a) stably transforming a plant cell with an isolated nucleic acid comprising a nucleotide sequence selected from the group consisting of:

(i) the nucleotide sequence of SEQ ID NO:9;

(ii) a nucleotide sequence having at least 96% sequence identity to the nucleotide sequence of (i);

(iii) a nucleotide sequence that differs from the nucleotide sequence of any of (i) to (ii) due to the degeneracy of the genetic code.

(b) regenerating a stably transformed plant from the stably transformed plant cell of (a); and (c) expressing the nucleotide sequence in the plant.

As another aspect, the invention provides an isolated nucleic acid comprising a nucleotide sequence selected from the group consisting of:

(a) the nucleotide sequence of SEQ ID NO:5 or SEQ ID NO:6;

(b) a nucleotide sequence comprising at least 100 consecutive nucleotides of the nucleotide sequence of SEQ ID NO:5 or SEQ ID NO:16;
(c) a nucleotide sequence that hybridizes to the complete complement of the nucleotide sequence of (a) or (b) under stringent hybridization conditions; and
(d) a nucleotide sequence having at least 95% sequence identity to the nucleotide sequences of any of (a) to (c).

In another embodiment, the invention provides an isolated nucleic acid comprising a nucleotide sequence selected from the group consisting of:
(a) the nucleotide sequence of SEQ ID NO:16;
(b) a nucleotide sequence comprising at least 25 consecutive nucleotides of the nucleotide sequence of nucleotides 1 to 800 of SEQ ID NO:16;
(c) a nucleotide sequence that hybridizes to the complete complement of nucleotides 1-200, 200-400, 400-600 and/or 600-800 of SEQ ID NO:16 under stringent hybridization conditions; and
(d) a nucleotide sequence having at least 95% sequence identity to the nucleotide sequences of any of (a) to (e).

In another embodiment, the invention provides an isolated nucleic acid comprising a nucleotide sequence selected from the group consisting of:
(a) the nucleotide sequence of SEQ ID NO:16;
(b) a nucleotide sequence comprising at least 100 consecutive nucleotides of nucleotides 1 to 800 of SEQ ID NO:16;
(c) a nucleotide sequence that hybridizes to the complete complement of the nucleotide sequence of (b) under stringent hybridization conditions; and
(d) a nucleotide sequence having at least 95% sequence identity to the nucleotide sequences of any of (a) to (c). In some embodiments, the isolated nucleic acid comprises the nucleotide sequence of SEQ ID NO:9.

Also provided are expression cassettes, vectors, cells, plants and plant parts comprising the isolated nucleic acids of the invention operably associated with a nucleotide sequence of interest.

In some embodiments, the invention encompasses and expression cassette comprising an isolated HaHB11 nucleic acid operably associated with a nucleotide sequence of interest. In further embodiments, the nucleotide sequence of interest is selected from the group consisting of: (a) the nucleotide sequence of SEQ ID NO:2; (b) the nucleotide sequence of SEQ ID NO:9; (c) a nucleotide sequence comprising at least 100 consecutive nucleotides of the nucleotide sequence of (a) or (b); (d) a nucleotide sequence having at least 95% sequence identity to the nucleotide sequence of (a) or (b); (e) a nucleotide sequence that hybridizes to the complete complement of the nucleotide sequence of (a) or (b) under stringent hybridization conditions; and (f) a nucleotide sequence that differs from the nucleotide sequence of any of (a) to (e) due to the degeneracy of the genetic code. In additional embodiments, the nucleotide sequence of interest encodes a polypeptide selected from the group consisting of: (a) a HAHB11 polypeptide of SEQ ID NO:3; (b) a HAHB11 polypeptide of SEQ ID NO:10; (c) a polypeptide comprising at least 100 consecutive amino acids of (a) or (b); and (d) a polypeptide sequence having at least 95% sequence identity to the sequence of (a) or (b). In some embodiments the isolated nucleic acid is operably associated with a heterologous nucleotide sequence of interest. In other embodiments, the expression cassette contains a sequence that encodes a selectable marker. Cells, plants and plant parts transformed with these nucleic acids, vectors, and expression cassettes are also encompassed by the invention. In particular embodiments, the transformed plants are monocots. In other embodiments, the transformed plants are dicots. In particular embodiments, the cells, plants and/or plant parts correspond to sunflower, wheat, maize, soybean, rice, alfalfa or *Arabidopsis*.

As an additional aspect, the invention also encompasses products harvested from the plants of the invention and processed products produced therefrom.

The invention also provides seed produced from the plants of the invention and seed comprising the isolated nucleic acids and expression cassettes of the invention.

As still a further aspect, the invention provides a method of introducing a nucleic acid into a plant, plant part or plant cell, the method comprising transforming the plant, plant part or plant cell with an isolated nucleic acid, expression cassette or vector of the invention.

As yet another aspect, the invention provides a method of stably expressing a nucleotide sequence of interest in a plant, the method comprising:
(a) stably transforming a plant cell with an expression cassette or vector of the invention;
(b) regenerating a stably transformed plant from the stably transformed plant cell of (a); and
(c) expressing the nucleotide sequence of interest in the plant.

These and other aspects of the invention are set forth in more detail in the description of the invention below.

BRIEF DESCRIPTION OF THE DRAWINGS

FIG. 1A is a schematic representation of the sunflower HaHB11 gene. The promoter region is shown as crosshatched, and the coding region as stippled. Putative cis acting elements are signaled in the promoter as well as the conserved. HD Zip domain in the coding sequence.

FIG. 2A. Polynucleotide sequence alignment of HaHB11.1 (SEQ. ID NO:2) and HaHB11.2 (SEQ ID NO:9) sequence variants.

FIG. 2B. Protein sequence alignment of HaHB11.1 (SEQ. ID NO:3) and HaHB11.2 (SEQ ID NO:10) sequence variants FIG. 2C. Protein sequence alignment of Asteraceae family HaHB11 orthologs/variants from *Helianthus annuus* (Hann; SEQ ID NO:3 and SEQ ID NO:10), *Helianthus tuberoses*, (Htub; SEQ ID NO:11, SEQ ID NO:14 and SEQ ID NO:15), *Helianthus argophyllus* (Harg; SEQ ID NO:12) and *Helianthus ciliaris* (Heil; SEQ ID NO:13).

Figure 27A:
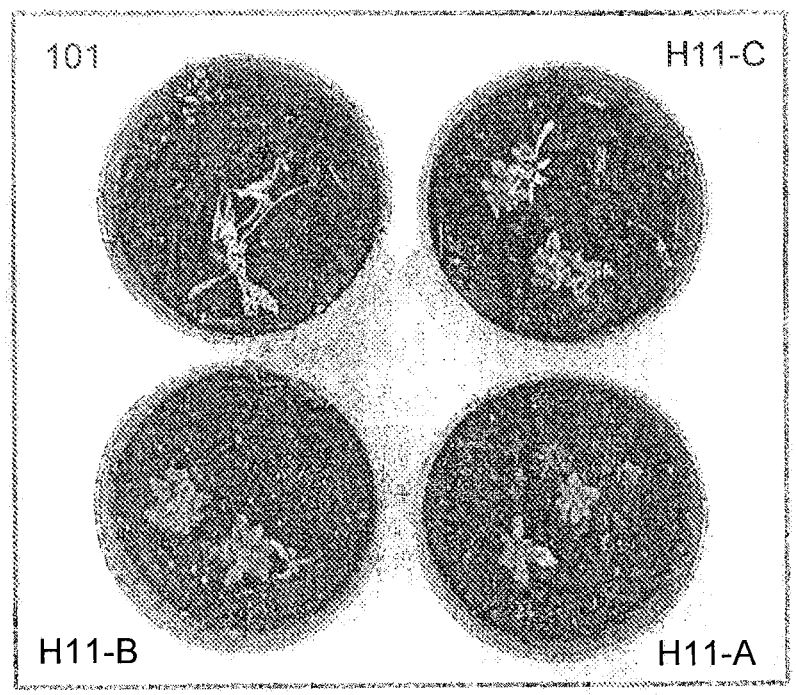
FIG. 27A-B: A—35S:HaHB11 plants tolerated submergence better than their controls. 21-day-old 35S:HaHB11 and WT (101) plants grown on soil and submerged during six days. The photograph was taken six days after recovery under standard conditions. B—chlorophyll content of the same plants.
Figure 27B:
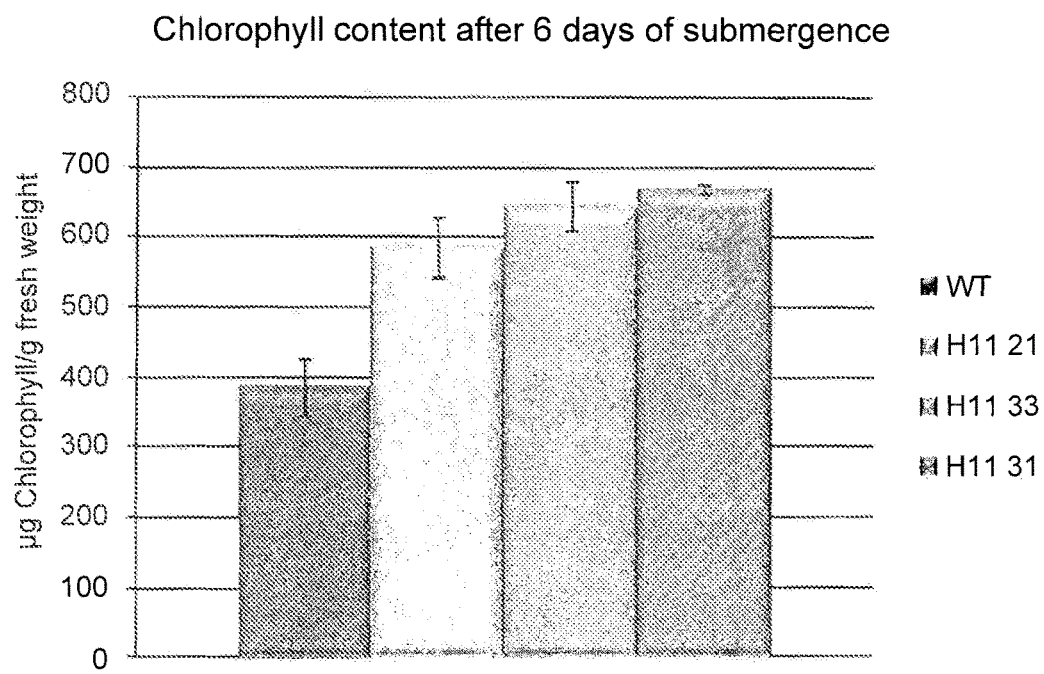
Figure 27C:
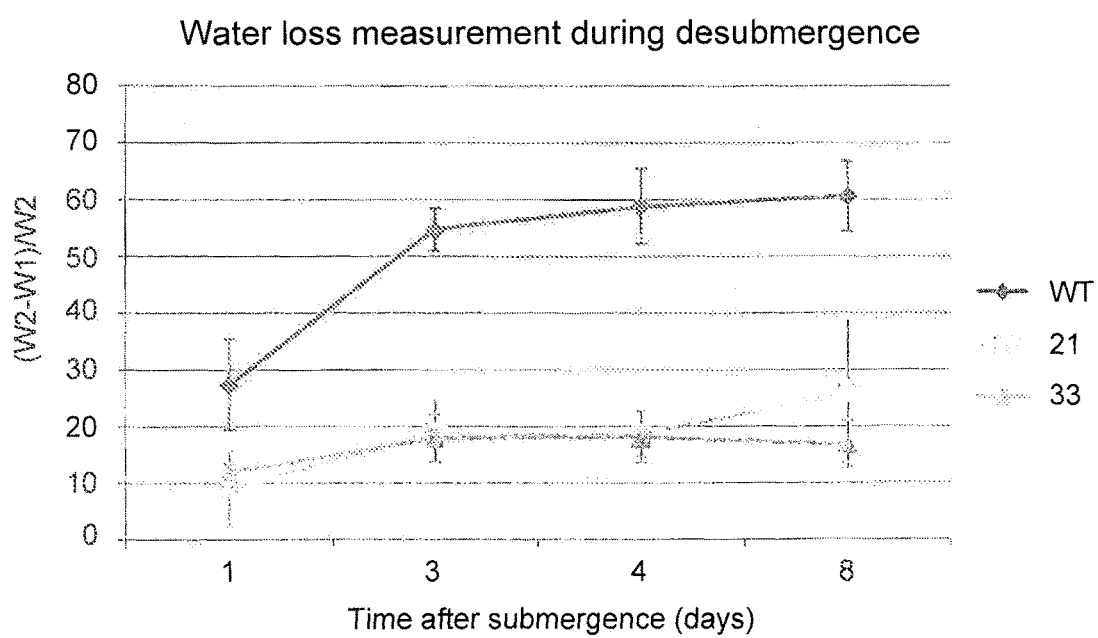

FIG. 27C. Water content quantified in plants subjected for six days to a submergence treatment and then, desubmerged. The x axis indicates days after the end of the submergence treatment.

Figure 28:
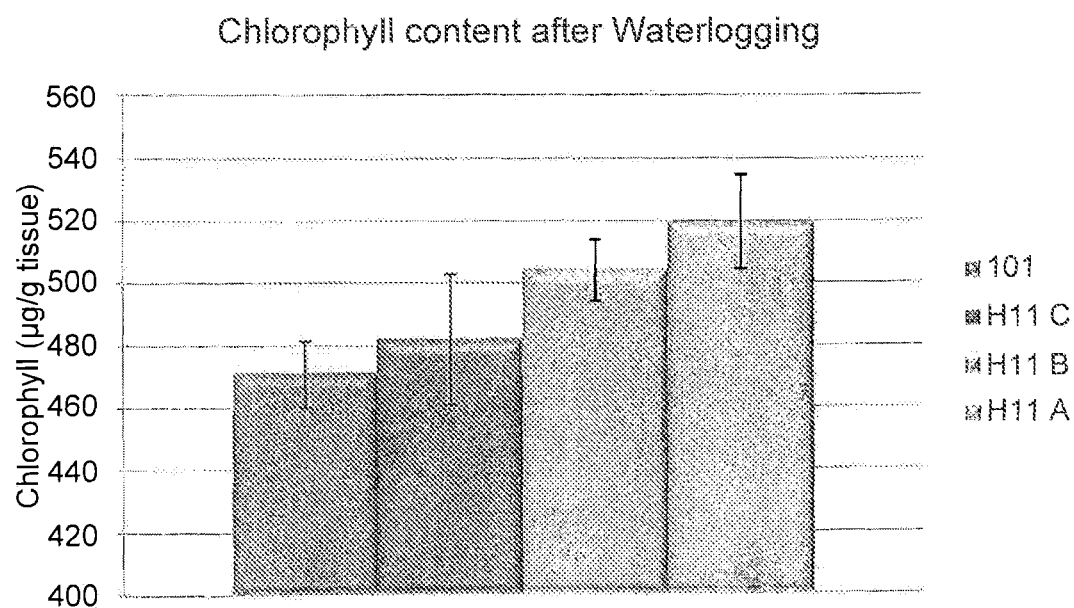

FIG. 28: Chlorophyll content after 6 days of waterlogging. 21-day-old 35S:HaHB11 and WT plants grown on soil with their roots submerged for six days. Chlorophyll content was measured after the treatment.

Figure 29:
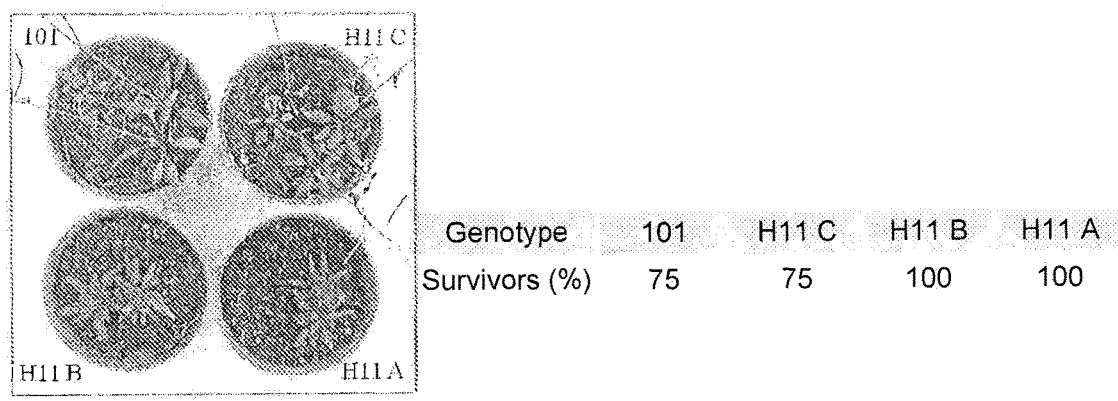

FIG. 29: Tolerance to waterlogging. 21-day-old 35S: HaHB11, and WT plants grown on soil with their roots submerged for six days. Photograph was taken and percentage of survivors was calculated 6 days after recovery.

Figure 30:
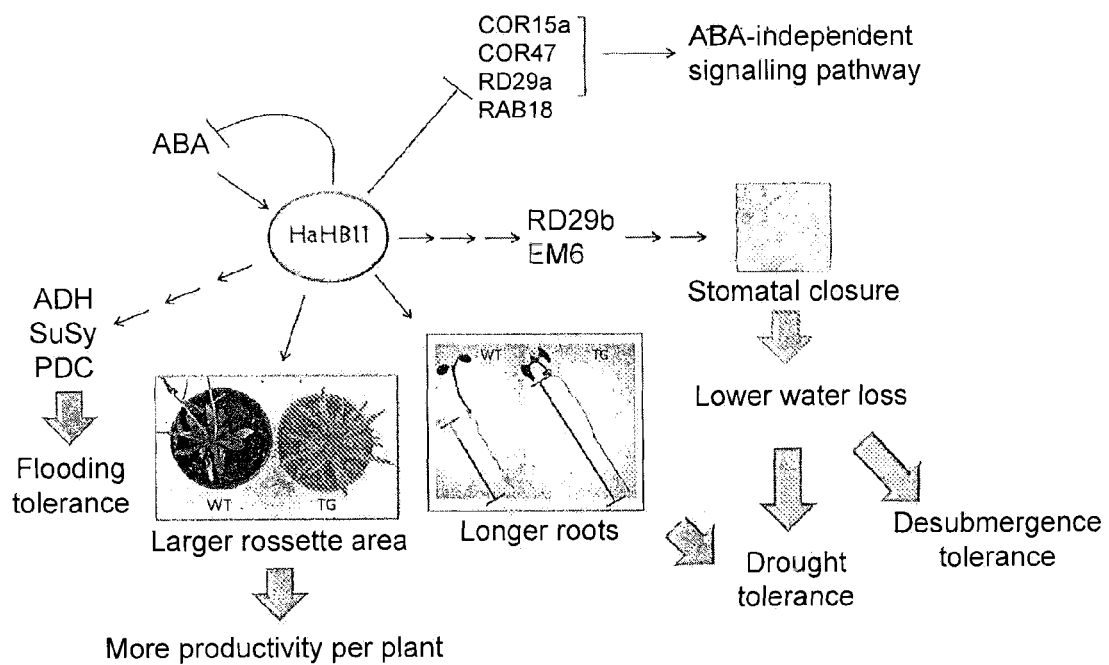

FIG. 30: Hypothetical model of HaHB11 function in plants.

Figure 31:
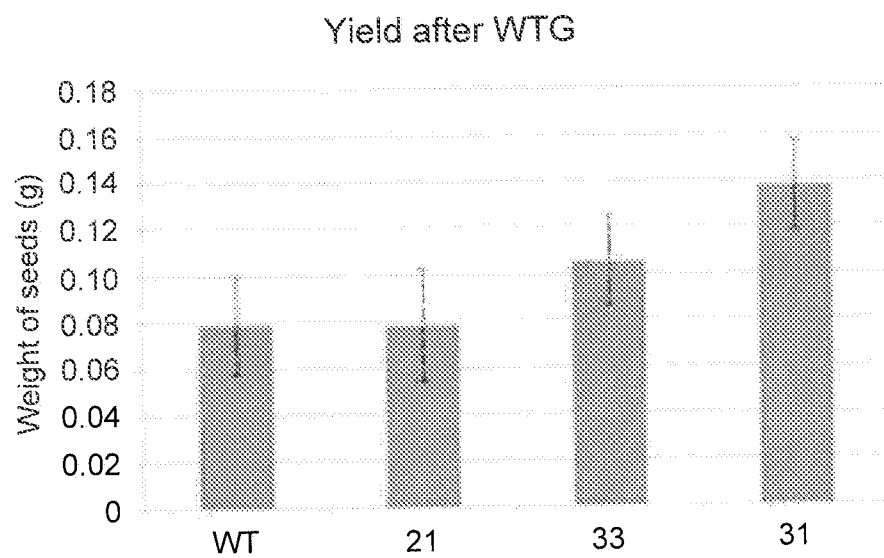

FIG. 31: Weight of seeds (g/plant) was obtained after harvesting of 35S:HaHB11 overexpressing and WT plants grown in under normal conditions or subjected to a mild stress (3 days of waterlogging) as described in the Experimental procedures. Seed weight obtained for HaHB11 and WT plants subjected to a moderate waterlogging stress. HaHB11 plants exhibit approximately twice the yield of WT plants.

FIG. 32 A-B: A—depicts a qualitative assay for starch using a lugol staining technique. B—presents a quantitation of the accumulated starch during the day. Starch quantification was performed at the end of the day. As depicted, transgenic plants exhibited more starch than WT under the tested conditions.

Figure 33:
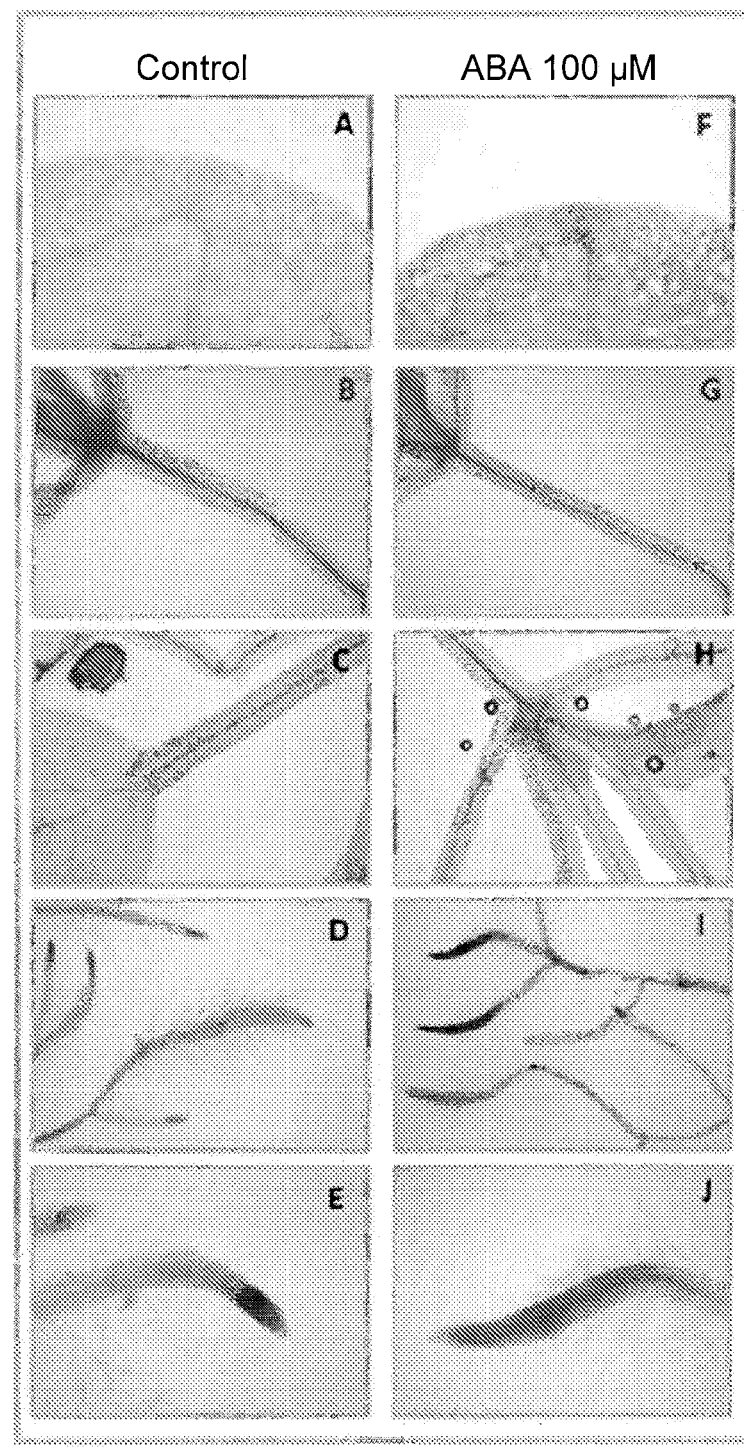

FIG. 33 A-J: Histochemical detection of GUS enzymatic activity in transgenic plants containing the long HaHB11 promoter (ProH11 long; SEQ ID NO:16) ProH11 long:GUS plants. 25-day-old plants were grown on MS medium at normal conditions or in presence of the fitohormone ABA for 1.5 hours. The figure demonstrate that the location of the expression did not change after ABA treatment. However, the intensity of the signal significantly increased in all the tissues, indicating an up-regulation of this promoter by ABA. Cotyledons (A and F), hypocotyls (B and G), petioles (C and H) and roots (D-J).

Figure 34:
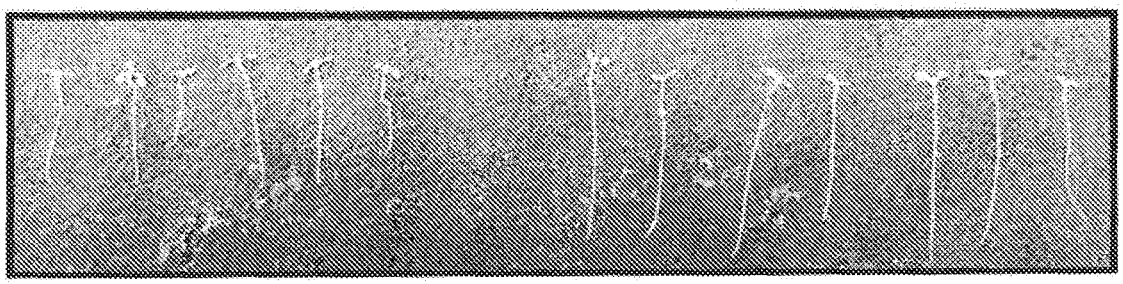

FIG. 34: Transgenic plants bearing the construct HaHB11 long promoter construct (SEQ IN NO:17) PromH11 long: HaHB11 exhibited significantly longer roots compared to the WT plants (transgenic for 35S::GUS).

Figure 35:
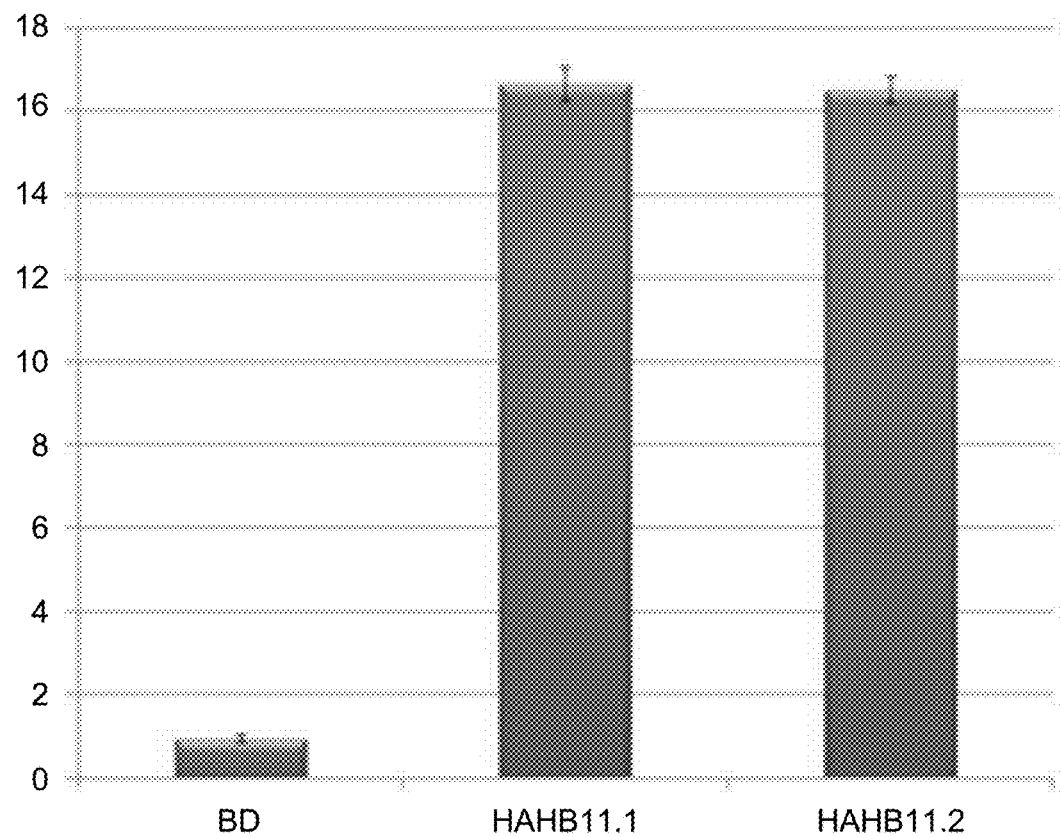

FIG. 35: depicts the results of a transcription activation assay in which *Sacharomyces cerevisiae*, strain Y187, was transformed with constructs encoding HaHB11.1 (SEQ ID NO:3) and HaHB11.2 (SEQ ID NO:10)). The activation assay was performed as described in the methods. The results indicate that HaHB11 acts as an activator, at least in the yeast system, and that both HaHB11.1 (SEQ ID NO:3) and HaB11.2 do not appear to differ significantly in this ability in the assay.

DETAILED DESCRIPTION OF THE INVENTION

The present invention is based, in part, on the discovery of new transcription factor in *Helianthus annuus*, designated as HaHB11. HaHB11 transgenic plants display longer roots than wild type plants (FIG. 34). Plants over-expressing HaHB11 exhibit increased tolerance to abiotic stress (including drought, salinity, waterlogging, submergence and desubmergence [post-water submergence] stress). In addition, HaHB11 over-expressers are taller and demonstrate an increased yield of seed under non-stressed conditions (e.g., normal cultivation conditions).

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have, the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

I. DEFINITIONS

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461,463 (CCPA 1976) (emphasis in the original); see also MPEP §2111.03. Thus, the term "consisting essentially of" when used in a claim or the description of this invention is not intended to be interpreted to be equivalent to "comprising."

An "abiotic stress" is a stressor from one or more outside, non-living factors that adversely affects the productivity and/or the survival of the organism. Abiotic stressors include, but are not limited to: drought, flooding, stress (e.g., due to waterlogging and/or submergence), stress following the removal of a flooding stressor (e.g., dehydration in the period following removal of a flooding stress such as desubmergence stress), salt stress (e.g., high or excessive salt conditions), high winds, heat or high temperature, cold temperature, freezing, fire, high light intensity, low light intensity, ozone, poor pH (too alkaline and/or too acidic), soil compaction and/or high radiation. Those skilled in the art will appreciate that an abiotic stress will depend on the preferred conditions for that organism, and may well vary due to the presence of other biotic and/or abiotic stressors.

Parameters for abiotic stress factors are species specific and even variety specific and therefore vary widely according to the species/variety exposed to the abiotic stress. Thus, while one species may be severely impacted by a salinity level of 4.0 dS m$^{-1}$, another species may not be affected until at least a salinity level of 6.0 dS m$^{-1}$ or even 10.0 dS m$^{-1}$. See, for example, Blaylock, A. D. ("Soil salinity, salt tolerance, and growth potential of horticultural and landscape plants," Univ. Wyoming, Cooperative Extension Service, Bulletin B-988, February 1994) in which different plants are categorized as sensitive, moderately sensitive, moderately tolerant and tolerant depending on the level of soil salinity required to affect plant growth. Thus, for example, the level of salinity that is excessive or high for a sensitive plant species or variety is not the same level of salinity that is excessive or high for a moderately sensitive plant or a tolerant plant. The same is true for other types of abiotic stress such as drought, waterlogging and submergence stress. Thus, a level of drought that can be tolerated by a sensitive plant species/variety is different from the level of drought that can be tolerated by a plant species/variety that is more drought tolerant. Likewise, the level of flooding (e.g., at the roots and/or the aerial parts of the plant) that can be tolerated by a sensitive plant species/variety is different from that for a plant that is more tolerant to excessive water (e.g., wet roots and/or submergence).

"Severe" abiotic stress results in death in control plants (e.g., plants not expressing an HaHB11 polypeptide of the invention), for example, at least about 10%, 20%, 30%, 40%, 50% or even more control plants die, whereas the plants of the invention (e.g., expressing an HaHB11 polypeptide of the invention) exhibit an increased survival, or even no plant death, and/or are less severely affected as compared with controls.

"Mild" abiotic stress is defined herein as conditions in which control plants do not die but their production is very low (e.g., reduced by at least about 30%, 40%, 50% or more), whereas the plants of the invention (e.g., expressing an HaHB1 polypeptide of the invention) exhibit increased production as compared with and/or are less severely affected, as compared with controls. For example, mild drought stress can be achieved by providing about 50% of the water needed to achieve maximum yield.

"Normal" growth conditions are conditions in which the plants are not exposed to significant biotic, abiotic, toxicologic or nutritional stress, e.g., conditions in which the plants are well irrigated and exposed to normal salt conditions. In particular embodiments, "normal" growth conditions are conditions in which plants are exposed to no detectable (e.g., measurable) biotic, abiotic, toxicologic or nutritional stress.

Thus, an "increased tolerance to abiotic stress" (and similar terms) as used herein refers to the ability of a plant or part thereof exposed to abiotic stress and transformed with an isolated or recombinant nucleic acid of the invention (e.g., encoding an HaHB11 polypeptide of the invention) to withstand a given abiotic stress better than a control plant or part thereof (e.g., a plant or part thereof that has been exposed to the same abiotic stress but has not been transformed with an isolated or recombinant nucleic acid molecule of the invention). Increased tolerance to abiotic stress can be measured using a variety of parameters including, but not limited to, the size and/or number of plants or parts thereof (e.g., leaf number and/or size), productivity or yield (e.g., of seed), relative water content, electrolyte leakage, stomata conductance, photosynthetic rate, internal $CO_2$ concentration, transpiration rate, chlorophyll fluorescence. Thus, in some embodiments of the invention, a transformed plant or part thereof comprising an isolated or recombinant nucleic acid molecule of the invention, thereby having increased tolerance to the abiotic stress, would have, for example, greater growth (e.g., plant height) and/or survival and/or yield as compared with a plant or part thereof exposed to the same stress but not having been transformed with an isolated or recombinant nucleic acid molecule of the invention.

As used herein, "flooding stress" includes any stress induced by excess water and encompasses both waterlogging stress and submergence stress.

The term "waterlogging stress," as used herein, includes the stress induced by water covering the roots and soil, but the aerial portion of the plant is not necessarily covered by water. For example, waterlogging stress can be induced under conditions in which the soil surrounding the roots is saturated with water. In embodiments of the invention, less than about 50% or 25% of the aerial portion of the plant is submerged under water. In embodiments of the invention, essentially none of the aerial portion of the plant is submerged (e.g., less than about 5% or 10%).

The term "submergence stress," as used herein, includes the stress induced when the aerial portion of the plant is substantially under water. In embodiments of the invention, at least about 15%, 20%, 25%, 30%, 40%, 50%, 75%, 85%, 90% or 95% of the aerial portions of the plant are submerged under water. In embodiments of the invention, the entire aerial portion of the plant is submerged under water.

An "increased yield" (and similar terms) as used herein refers to an enhanced or elevated production of a commercially and/or agriculturally important plant, plant biomass, plant part (e.g., roots, tubers, seed, leaves, fruit), plant material (e.g., an extract) and/or other product produced by the plant (e.g., a recombinant polypeptide) by a plant or part thereof exposed to abiotic stress and transformed with an isolated or recombinant nucleic acid of the invention (e.g., encoding an HaHB11 polypeptide of the invention) as compared with a control plant or part thereof (e.g., a plant or part thereof that has been exposed to the same abiotic stress but has not been transformed with an isolated or recombinant nucleic acid molecule of the invention).

The term "modulate" (and grammatical variations) refers to an increase or decrease.

As used herein, the terms "increase," "increases," "increased," "increasing" and similar terms indicate an elevation of at least about 25%, 50%, 75%, 100%, 150%, 200%, 300%, 400%, 500% or more.

As used herein, the terms "reduce," "reduces," "reduced," "reduction" and similar terms mean a decrease of at least about 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or amount.

As used herein, the term "heterologous" means foreign, exogenous, non-native and/or non-naturally occurring.

As used here, "homologous" means native. For example, a homologous nucleotide sequence or amino acid sequence is a nucleotide sequence or amino acid sequence naturally associated with a host cell into which it is introduced, a homologous promoter sequence is the promoter sequence that is naturally associated with a coding sequence, and the like.

As used herein a "chimeric nucleic acid," "chimeric nucleotide sequence" or "chimeric polynucleotide" comprises a promoter operably linked to a nucleotide sequence of interest that is heterologous to the promoter (or vice versa). In particular embodiments, the "chimeric nucleic acid," "chimeric nucleotide sequence" or "chimeric polynucleotide" comprises a HaHB11 promoter element operably associated with a heterologous nucleotide sequence of interest to be transcribed. In other representative embodiments, the "chimeric nucleic acid," "chimeric nucleotide sequence" or "chimeric polynucleotide" comprises a HaHB11 coding sequence operably associated with a heterologous promoter.

A "promoter" is a nucleotide sequence that controls or regulates the transcription of a nucleotide sequence (i.e., a coding sequence) that is operatively associated with the promoter. The coding sequence may encode a polypeptide and/or a functional RNA Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach et al., Annu. Rev. Biochem. 50:349 (1981)). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). The promoter region, including all the ancillary regulatory elements, typically contain between about 100 and 1000 nucleotides, but can be as long as 2 kb, 3 kb, 4 kb or longer in length. Promoters according to the present invention can function as constitutive and/or inducible regulatory elements.

A "functional" RNA includes any untranslated RNA that has a biological function in a cell, e.g., regulation of gene expression. Such functional RNAs include but are not limited to siRNA, shRNA, miRNA, antisense RNA, ribozymes, and the like.

By "operably linked" or "operably associated" as used herein, it is meant that the indicated elements are functionally related to each other, and are also generally physically related. For example, a promoter is operatively linked or operably associated to a coding sequence (e.g., nucleotide sequence of interest) if it controls the transcription of the sequence. Thus, the term "operatively linked" or "operably associated" as used herein, refers to nucleotide sequences on a single nucleic acid molecule that are functionally associated. Those skilled in the art will appreciate that the control sequences (e.g., promoter) need not be contiguous with the coding sequence, as long as they functions to direct the expression thereof. Thus, for example, intervening untranslated, yet transcribed, sequences can be present between a promoter and a coding sequence, and the promoter sequence can still be considered "operably linked" to the coding sequence.

"Nucleotide sequence of interest" refers to any nucleotide sequence which, when introduced into a plant, confers upon the plant a desired characteristic such as antibiotic resistance, virus resistance, insect resistance, disease resistance, or resistance to other pests, herbicide tolerance, abiotic stress resistance (e.g., drought tolerance, salt tolerance, tolerance to waterlogging and/or submergence stress, and the like), improved nutritional value, improved performance in an industrial process or altered reproductive capability. The "nucleotide sequence of interest" can encode a polypeptide or functional RNA (e.g., a regulatory RNA). For example, the "nucleotide sequence of interest" may be one that is transferred to plants for the production of a polypeptide (e.g., an enzyme, hormone, growth factor or antibody) for commercial production.

A "heterologous nucleotide sequence" or "heterologous nucleotide sequence of interest" as used herein is a coding sequence that is heterologous to the HaHB11 promoter of the invention (i.e., is not the native HaHB11 sequence). The heterologous nucleotide sequence can encode a polypeptide or a functional RNA. A "heterologous promoter" is a promoter that is heterologous to the nucleotide sequence with which it is operatively associated. For example, according to the present invention, the HaHB11 coding sequence can be operatively associated with a heterologous promoter (e.g., a promoter that is not the native HaHB11 promoter sequence with which the HaHB11 coding sequence is associated in its naturally occurring state).

By the term "express," "expressing" or "expression" (or other grammatical variants) of a nucleic acid coding sequence, it is meant that the sequence is transcribed. In particular embodiments, the terms "express," "expressing" or "expression" (or other grammatical variants) can refer to both transcription and translation to produce an encoded polypeptide.

"Wild-type" nucleotide sequence or amino acid sequence refers to a naturally occurring ("native") or endogenous nucleotide sequence (including a cDNA corresponding thereto) or amino acid sequence.

The terms "nucleic acid," "polynucleotide" and "nucleotide sequence" can be used interchangeably herein unless the context indicates otherwise. These terms encompass both RNA and DNA, including cDNA, genomic DNA, partially or completely synthetic (e.g., chemically synthesized) RNA and DNA, and chimeras of RNA and DNA. The nucleic acid, polynucleotide or nucleotide sequence may be double-stranded or single-stranded, and further may be synthesized using nucleotide analogs or derivatives (e.g., inosine or phosphorothioate nucleotides). Such nucleotides can be used, for example, to prepare nucleic acids, polynucleotides and nucleotide sequences that have altered base-pairing abilities or increased resistance to nucleases. The present invention further provides a nucleic acid, polynucleotide or nucleotide sequence that is the complement (which can be either a full complement or a partial complement) of a nucleic acid, polynucleotide or nucleotide sequence of the invention (e.g., encodes a nucleic acid, polynucleotide or nucleotide sequence comprising, consisting essentially of, or consisting of a HaHB11 promoter element and/or is the complement of a HaHB11 coding sequence of the invention). Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

The nucleic acids and polynucleotides of the invention are optionally isolated. An "isolated" nucleic acid molecule or polynucleotide is a nucleic acid molecule or polynucleotide that, by the hand of man, exists apart from its native environment and is therefore not a product of nature. An isolated nucleic acid molecule or isolated polynucleotide may exist in a purified form or may exist in a non-native environment such as, for example, a recombinant host cell. Thus, for example, the term "isolated" means that it is separated from the chromosome and/or cell in which it naturally occurs. A nucleic acid or polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and polynucleotides of the invention can be considered to be "isolated."

Further, an "isolated" nucleic acid or polynucleotide is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. The "isolated" nucleic acid or polynucleotide can exist in a cell (e.g., a plant cell), optionally stably incorporated into the genome. According to this embodiment, the "isolated" nucleic acid or polynucleotide can be foreign to the cell/organism into which it is introduced, or it can be native to an the cell/organism (e.g., *Helianthus annuus*), but exist in a recombinant form (e.g., as a chimeric nucleic acid or polynucleotide) and/or can be an additional copy of an endogenous nucleic acid or polynucleotide. Thus, an "isolated nucleic acid molecule" or "isolated polynucleotide" can also include a nucleotide sequence derived from and inserted into the same natural, original cell type, but which is present in a non-natural state, e.g., present in a different copy number, in a different genetic context and/or under the control of different regulatory sequences than that found in the native state of the nucleic acid molecule or polynucleotide.

In representative embodiments, the "isolated" nucleic acid or polynucleotide is substantially free of cellular material (including naturally associated proteins such as histones, transcription factors, and the like), viral material, and/or culture medium (when produced by recombinant DNA techniques), or chemical precursors or other chemicals (when chemically synthesized). Optionally, in representative embodiments, the isolated nucleic acid or polynucleotide is at least about 10%, 20%, 30%, 40%, 50%, 60%, 70%, 80%, 90%, 95% or more pure.

As used herein, the term "recombinant" nucleic acid, polynucleotide or nucleotide sequence refers to a nucleic acid, polynucleotide or nucleotide sequence that has been constructed, altered, rearranged and/or modified by genetic engineering techniques. The term "recombinant" does not refer to alterations that result from naturally occurring events, such as spontaneous mutations, or from non-spontaneous mutagenesis.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in the cell, i.e., capable of nucleic acid replication under its own control. The term "vector" includes both viral and nonviral (e.g., plasmid) nucleic acid molecules for introducing a nucleic acid into a cell in vitro, ex vivo, and/or in vivo, and is optionally an expression vector. A large number of vectors known in the art may be used to manipulate, deliver and express polynucleotides. Vectors may be engineered to contain sequences encoding selectable markers that provide for the selection of cells that contain the vector and/or have integrated some or all of the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (e.g., transgenes), e.g., two, three, four, five or more heterologous nucleotide sequences.

Viral vectors have been used in a wide variety of gene delivery applications in cells, as well as living animal subjects. Plant viral vectors that can be used include, but are not limited to, *Agrobacterium tumefaciens*, *Agrobacterium rhizogenes* and geminivirus vectors. Non-viral vectors include, but are not limited to, plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (e.g., delivery to specific tissues, duration of expression, etc.).

The term "fragment," as applied to a nucleic acid or polynucleotide, will be understood to mean a nucleotide sequence of reduced length relative to the reference or full-length nucleotide sequence and comprising, consisting essentially of and/or consisting of contiguous nucleotides from the reference or full-length nucleotide sequence. Such a fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 16, 17, 18, 19, 20, 25, 30, 35, 40, 45, 50, 75, 100, 125, 150, 175, 200, 225, 250, 275, 300, 325, 350, 375, 400, 405, 410, 425, 450, 455, 460, 475, 500, 505, 510, 515 or 520 nucleotides (optionally, contiguous nucleotides) or more from the reference or full-length nucleotide sequence, as long as the fragment is shorter than the reference or full-length nucleotide sequence. In representative embodiments, the fragment is a biologically active nucleotide sequence, as that term is described herein.

A "biologically active" nucleotide sequence is one that substantially retains at least one biological activity normally associated with the wild-type nucleotide sequence, for example, the ability to drive transcription of an operatively associated coding sequence. In particular embodiments, the "biologically active" nucleotide sequence substantially retains all of the biological activities possessed by the unmodified sequence. By "substantially retains" biological activity, it is meant that the nucleotide sequence retains at least about 50%, 60%, 75%, 85%, 90%, 95%, 97%, 98%, 99%, or more, of the biological activity of the native nucleotide sequence (and can even have a higher level of activity than the native nucleotide sequence). For example, a biologically active promoter element is able to control, regulate and/or enhance the expression of a nucleotide sequence operably associated with the promoter. Methods of measuring expression of a nucleotide sequence are well known in the art and include Northern blots, RNA run-on assays and methods of measuring the presence of an encoded polypeptide (e.g., antibody based methods or visual inspection in the case of a reporter polypeptide).

Two nucleotide sequences are said to be "substantially identical" to each other when they share at least about 60%, 70%, 75%, 80%, 85%, 90%, 95%, 97%, 98%, 99% or even 100% sequence identity.

Two amino acid sequences are said to be "substantially identical" or "substantially similar" to each other when they share at least about 60%, 70%, 75%, 80%, 85%, 90%, 95%, 97%, 98%, 99% or even 100% sequence identity or similarity, respectively.

As used herein "sequence identity" refers to the extent to which two optimally aligned polynucleotide or polypeptide sequences are invariant throughout a window of alignment of components, e.g., nucleotides or amino acids.

As used herein "sequence similarity" is similar to sequence identity (as described herein), but permits the substitution of conserved amino acids (e.g., amino acids whose side chains have similar structural and/or biochemical properties), which are well-known in the art.

As is known in the art, a number of different programs can be used to identify whether a nucleic acid has sequence identity or an amino acid sequence has sequence identity or similarity to a known sequence. Sequence identity or similarity may be determined using standard techniques known in the art, including, but not limited to, the local sequence identity algorithm of Smith & Waterman, Adv. Appl. Math. 2, 482 (1981), by the sequence identity alignment algorithm of Needleman et al., J. Mol. Biol. 48,443 (1970), by the search for similarity method of Pearson & Lipman, PNAS 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng et al., J. Mol. Evol. 35:351-360 (1987); the method is similar to that described by Higgins et al., CABIOS 5:151-153 (1989).

Another example of a useful algorithm is the BLAST algorithm, described in Altschul et al., J. Mol. Biol. 215: 403-410, (1990) and Karlin et al., PNAS 90:5873-5787 (1993). A particularly useful BLAST program is the WU-BLAST-2 program which was obtained from Altschul et al., Methods in Enzymology, 266, 460-480 (1996); at blast.wustl/edu/blastl READMEhtml. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucleic Acids Res. 25:3389-3402 (1997).

The CLUSTAL program can also be used to determine sequence similarity. This algorithm is described by Higgins et al., Gene 73:237 (1988); Higgins et al., CABIOS 5:151-153 (1989); Corpet et al., Nucleic Acids Res. 16:10881-90 (1988); Huang et al., CABIOS 8:155-65 (1992); and Pearson et al., Meth. Mol. Biol. 24:307-331 (1994).

The alignment may include the introduction of gaps in the sequences to be aligned. In addition, for sequences which contain either more or fewer nucleotides than the nucleic acids disclosed herein, it is understood that in one embodiment, the percentage of sequence identity will be determined based on the number of identical nucleotides acids in relation to the total number of nucleotide bases. Thus, for example, sequence identity of sequences shorter than a sequence specifically disclosed herein, will be determined using the number of nucleotide bases in the shorter sequence, in one embodiment. In percent identity calculations relative weight is not assigned to various manifestations of sequence variation, such as, insertions, deletions, substitutions, etc.

Two nucleotide sequences can also be considered to be substantially identical when the two sequences hybridize to each other under stringent conditions. A nonlimiting example of "stringent" hybridization conditions include conditions represented by a wash stringency of 50% Formamide with 5×Denhardt's solution, 0.5% SDS and 1×SSPE at 42° C. "Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen Laboratory Techniques in Biochemistry and Molecular Biology-Hybridization with Nucleic Acid Probes part I chapter 2 "Overview of principles of hybridization and the strategy of nucleic acid probe assays" Elsevier, New York (1993). In some representative embodiments, two nucleotide sequences considered to be substantially identical hybridize to each other under highly stringent conditions. Generally, highly stringent hybridization and wash conditions are selected to be about 5° C. lower than the thermal melting point (Tm) for the specific sequence at a defined ionic strength and pH.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

The polypeptides of the invention are optionally "isolated." An "isolated" polypeptide is a polypeptide that, by the hand of man, exists apart from its native environment and is therefore not a product of nature. An isolated polypeptide may exist in a purified form or may exist in a non-native environment such as, for example, a recombinant host cell. The recombinant polypeptides of the invention can be considered to be "isolated."

In representative embodiments, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material. In representative embodiments, the isolated polypeptide is a recombinant polypeptide produced using recombinant nucleic acid techniques. In embodiments of the invention, the polypeptide is a fusion protein.

The term "fragment," as applied to a polypeptide, will be understood to mean an amino acid of reduced length relative to a reference polypeptide or the full-length polypeptide (e.g., HaHB11) and comprising, consisting essentially of, and/or consisting of a sequence of contiguous amino acids from the reference or full-length polypeptide. Such a fragment according to the invention may be, where appropriate, included as part of a fusion protein of which it is a constituent. In some embodiments, such fragments can comprise, consist essentially of, and/or consist of polypeptides having a length of at least about 50, 75, 100, 125, 150, 160, 165, 170, 171, 172, 173 or 174 amino acids (optionally, contiguous amino acids) from the reference or full-length polypeptide, as long as the fragment is shorter than the reference or full-length polypeptide. In representative embodiments, the fragment is biologically active, as that term is defined herein.

A "biologically active" polypeptide is one that substantially retains at least one biological activity normally associated with the wild-type polypeptide, for example, the ability to increase tolerance to abiotic stress and/or increase yield. In another embodiment, a biologically active polypeptide is capable of: binding the sequence CAAT(A/T)ATTG (SEQ ID NO:7) under physiological conditions in vitro, binding one or more different endogenous host plant proteins under physiological conditions in vitro, and/or activating transcription in a yeast two-hybrid system such as, described herein. In particular embodiments, the "biologically active" polypeptide substantially retains all of the biological activities possessed by the unmodified (wild-type) sequence. By "substantially retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). Methods of measuring yield and tolerance to abiotic stress are known in the art, with non-limiting and exemplary methods are described in the working Examples herein.

"Introducing" in the context of a plant cell, plant tissue, plant part and/or plant means contacting a nucleic acid molecule with the plant cell, plant tissue, plant part, and/or plant in such a manner that the nucleic acid molecule gains access to the interior of the plant cell or a cell of the plant tissue, plant part or plant. Where more than one nucleic acid molecule is to be introduced, these nucleic acid molecules can be assembled as pan of a single polynucleotide or nucleic acid construct, or as separate polynucleotide or nucleic acid constructs, and can be located on the same or different nucleic acid constructs. Accordingly, these nucleic acid molecules can be introduced into plant cells in a single transformation event, in separate transformation events, or, e.g., as part of a breeding protocol.

The term "transformation" as used herein refers to the introduction of a heterologous nucleic acid into a cell. Transformation of a cell may be stable or transient. Thus, a transgenic plant cell, plant tissue, plant part and/or plant of the invention can be stably transformed or transiently transformed.

"Transient transformation" in the context of a polynucleotide means that a polynucleotide is introduced into the cell and does not integrate into the genome of the cell.

As used herein, "stably introducing," "stably introduced," "stable transformation" or "stably transformed" (and similar terms) in the context of a polynucleotide introduced into a cell, means that the introduced polynucleotide is stably integrated into the genome of the cell (e.g., into a chromosome or as a stable-extra-chromosomal element). As such, the integrated polynucleotide is capable of being inherited by progeny cells and plants.

"Genome" as used herein includes the nuclear and/or plastid genome, and therefore includes integration of a polynucleotide into, for example, the chloroplast genome. Stable transformation as used herein can also refer to a polynucleotide that is maintained extrachromosomally, for example, as a minichromosome.

As used herein, the terms "transformed" and "transgenic" refer to any plant, plant cell, plant tissue (including callus), or plant part that contains all or part of at least one recombinant or isolated nucleic acid, polynucleotide or nucleotide sequence. In representative embodiments, the recombinant or isolated nucleic acid, polynucleotide or nucleotide sequence is stably integrated into the genome of the plant (e.g., into a chromosome or as a stable extra-chromosomal element), so that it is passed on to subsequent generations of the cell or plant.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "Plant part" also includes plant cells including plant cells that are intact in plants and/or parts of plants, plant protoplasts, plant tissues, plant organs plant cell tissue cultures, plant calli, plant clumps, and the like. As used herein, "shoot" refers to the above ground parts including the leaves and stems.

The term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. Any plant (or groupings of plants, for example, into a genus or higher order classification) can be employed in practicing the present invention including angiosperms or gymnosperms, monocots or dicots.

Exemplary transgenic plants of the invention include, but are not limited to, corn (*Zea mays*), canola (*Brassica napus, Brassica rapa* ssp.), alfalfa (*Medicago saliva*), rice (*Oryza sativa*), rape (*Brassica napus*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tobacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia*

*integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna*), oats, barley, vegetables, ornamentals, conifers, and turfgrasses (e.g., for ornamental, recreational or forage purposes), and biomass grasses (e.g., switchgrass and *miscanthus*).

Exemplary transgenic vegetables of the invention include, but are not limited to, *Solanaceous* species (e.g., tomatoes; *Lycopersicon esculentum*), lettuce (e.g., *Lactuea sativa*), carrots (*Caucus carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschata*), Zucchini (*C. pepo*), Crookneck squash (*C. crookneck*), *C. argyrosperma*, *C. argyrosperma* ssp *sororia*, *C. digitata*, *C. ecuadorensis*, *C. foetidissima*, *C. lundelliana*, and *C. martinezii*, and members of the genus *Cucumis* such as cucumber (*Cucumis sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosa-sanensis*), roses (*Rosa* spp.), tulips (*Tulipa* spp.), daffodils (*Narcissus* spp.), petunias (*Petunia hybrida*), carnation (*dianthus caryophyllus*), poinsettia (*Euphorbia pulcherima*), and chrysanthemum.

Conifers, which may be employed in practicing the present invention, include, for example pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass which may be employed in practicing the present invention, include but are not limited to zoysiagrasses, bentgrasses, fescue grasses, bluegrasses, St. Augustinegrasses, bermudagrasses, bufallograsses, ryegrasses, and orchardgrasses.

In particular embodiments, the transgenic plants of the invention are a member selected from wheat (*Tritium aestivum*), corn (*Zea mays*) and rice (*Oryza sativa*). In an additional embodiment, the transgenic plants are alfalfa or sunflower. In a particular embodiment, the transgenic plants are soybean (*Glycine max*).

Also included as transgenic plants of the invention are plants that serve primarily as laboratory models, e.g., *Arabidopsis*.

II. HAHB11 POLYPEPTIDES, HAHB11 CODING SEQUENCES AND PROMOTER SEQUENCES

As one aspect, the present invention provides HaHB11 polypeptides. The term "HaHB11 polypeptide" is intended to encompass the HaHB11 polypeptides specifically described herein (e.g., SEQ ID NO:3 and SEQ ID NO:10) as well as equivalents thereof, e.g., that have substantially identical or similar amino acid sequences (as described herein) to the HaHB11 polypeptides specifically described herein, optionally biologically active equivalents that have one or more of the biological activities of the HaHB11 polypeptides specifically described herein. The term "HaHB11 polypeptide" also encompasses fragments of the full-length HaHB11 polypeptides specifically disclosed herein, optionally biologically active fragments, and biologically active equivalents thereof that have substantially identical or similar amino acid sequences to a fragment of a full-length HaHB11 polypeptide specifically disclosed herein. Further, the term "HaHB11 polypeptide" includes sequences from *Helianthus annuus* or can be an ortholog from any other suitable plant species and also includes naturally occurring allelic variations, isoforms, splice variants and the like. Exemplary HaHB11 polypeptides of the invention include, but are not limited to, a protein having the amino acid sequence of: SEQ ID NO:11, SEQ ID NO:12; SEQ ID NO:13, SEQ ID NO:14 or SEQ ID NO:15. The HaHB11 polypeptide sequences can further be wholly or partially synthetic.

Biological activities associated with expression of HaHB11 in a plant include but are not limited to, increased tolerance to abiotic stress (e.g., drought, submergence, desubmergence, waterlogging and/or salt stress), delayed development, greater or reduced plant height, and/or increased yield (e.g., under normal conditions and/or conditions of mild and/or severe abiotic stress). Additional biological activities associated with expression of HaHB11 in a plant include increased root length. Methods of assessing tolerance to abiotic stress, development, and yield are well known in the art (see the Examples for exemplary methods).

In particular embodiments, the HaHB11 polypeptide comprises, consists essentially of, or consists of an isolated HaHB11 polypeptide of SEQ ID NO:3 or an equivalent thereof (including fragments and equivalents thereof).

In additional particular embodiments, the HaHB11 polypeptide comprises, consists essentially of, or consists of an isolated HaHB11 polypeptide of SEQ ID NO:10 or an equivalent thereof (including fragments and equivalents thereof).

In some embodiments, the HaHB11 polypeptide comprises, consists essentially of, or consists of an the N terminal region, homeodomain, leucine zipper or C-terminal region of a HaHB11 polypeptide disclosed herein.

In particular embodiments, the HaHB11 polypeptide comprises, consists essentially of, or consists of an N terminal region of a HaHB11 polypeptide disclosed herein. In some embodiments, the HaHB11 polypeptide comprises, consists essentially of, or consists of an N terminal region having the amino acid sequence of amino acids 1 to 14 of SEQ ID NO:3. In some embodiments, the HaHB11 polypeptide comprises, consists essentially of, or consists of an N terminal region having an amino acid sequence selected from: amino acids 1 to 14 of SEQ ID NO:12, amino acids 1 to 14 of SEQ ID NO:14; and amino acids 1 to 14 of SEQ ID NO:15.

In additional embodiments, the HaHB11 polypeptide comprises, consists essentially of, or consists of a homeodomain of a HaHB11 polypeptide disclosed herein. In some embodiments, the HaHB11 polypeptide comprises, consists essentially of, or consists of a homeodomain having the amino acid sequence of amino acids 15 to 74 of SEQ ID NO:3. In some embodiments, the HaHB11 polypeptide comprises, consists essentially of, or consists of a homeodomain having the amino acid sequence of amino acids 15 to 77 of SEQ ID NO:10. In some embodiments, the HaHB11 polypeptide comprises, consists essentially of, or consists of a homeodomain having an amino acid sequence of amino acids 15 to 74 of SEQ ID NO:12 or amino acids 15 to 74 of SEQ ID NO:13.

In additional embodiments, the HaHB11 polypeptide comprises, consists essentially of, or consists of a leucine zipper of a HaHB11 polypeptide disclosed herein. In some embodiments, the HaHB11 polypeptide comprises, consists essentially of, or consists of a leucine zipper having the amino acid sequence of amino acids 75-110 of SEQ ID NO:3. In some embodiments, the HaHB11 polypeptide comprises, consists essentially of, or consists of a leucine zipper having the amino acid sequence of amino acids 78-113 of SEQ ID NO:11. In some embodiments, the HaHB11 polypeptide comprises, consists essentially of, or consists of a leucine zipper having an amino acid sequence selected from: amino acids 77 to 112 of SEQ ID NO:14 or amino acids 76 to 111 of SEQ ID NO:15.

In additional embodiments, the HaHB11 polypeptide comprises, consists essentially of, or consists of a C-terminal region of a HaHB11 polypeptide disclosed herein. In some embodiments, the HaHB11 polypeptide comprises, consists essentially of, or consists of a leucine zipper having the amino acid sequence of amino acids 111-175 of SEQ ID NO:3. In some embodiments, the HaHB11 polypeptide comprises, consists essentially of, or consists of a leucine zipper having the amino acid sequence of amino acids 114-181 of SEQ ID NO:10. In some embodiments, the HaHB11 polypeptide comprises, consists essentially of, or consists of a C-terminal region having an amino acid sequence selected from: amino acids 114 to 180 of SEQ ID NO:11, amino acids 111 to 179 of SEQ ID NO:12; amino acids 111 to 177 of SEQ ID NO:13, amino acids 113 to 183 of SEQ ID NO:14 and amino acids 112 to 186 of SEQ ID NO:15.

Equivalents of the HaHB11 polypeptides of the invention encompass those that have substantial amino acid sequence identity or similarity, for example, at least about 60%, 70%, 75%, 80%, 85%, 90%, 95%, 97%, 98%, 99% or more amino acid sequence identity or similarity with the amino acid sequences specifically disclosed herein (e.g., SEQ ID NO:3) or a fragment thereof, optionally a biologically active fragment. Additional equivalents of the HaHB11 polypeptides of the invention encompass those that have substantial amino acid sequence identity or similarity, for example, at least about 96%, 97%, 98%, 99% or more amino acid sequence identity or similarity with the amino acid sequence of SEQ ID NO:10 or a fragment thereof, optionally a biologically active fragment.

Figure 1B:
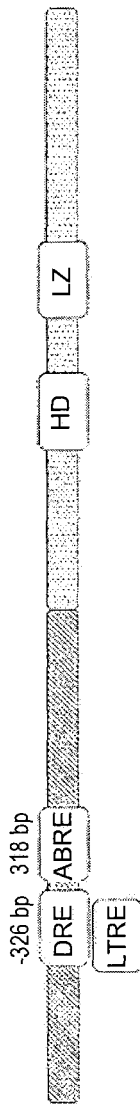
FIG. 1B is a schematic representation of the sunflower HaHB11 protein (SEQ ID NO: 3). The homeodomain (HD) is shown in bold. The leucine zipper (Zip) is underlined; each leucine (L) is also shown in bold. The amino terminal domain is shown in italics. The carboxyl-terminus is shown in double underlining. Putative casein-phosphorylation sites are shown in black shadowing with white letters. A putative transactivation site is shown in black shadowing with gray letters. A putative protein kinase phosphorylation site is shown in gray letters.

In representative embodiments, the HaHB11 polypeptide comprises the homeodomain, leucine zipper, the transactivation site, and/or the putative protein-kinase phosphorylation site domains (see, schematic in FIG. 1B), and optionally any sequence variability occurs outside of this region(s). In representative embodiments, the HaHB11 polypeptide comprises the first, second, third and/or fourth casein-phosphorylation site (numbering with respect to the N-terminus; FIG. 1B), and optionally any variability occurs outside this domain. In representative embodiments, the HaHB11 polypeptide comprises the N-terminal region (see FIG. 1B) and, optionally, any sequence variation occurs outside this domain. In additional representative embodiments, the HaHB11 polypeptide comprises the C-terminal domain (FIG. 1B) and; optionally, any sequence variability occurs outside of this region. In representative embodiments, the homeodomain, leucine zipper, transactivation site, protein kinase phosphorylation site, casein phosphorylation sites, N-terminal domain and/or C-terminal domain have the sequence(s) as shown in FIG. 1B. In additional embodiments, the sequence is an equivalent of the sequence as shown in FIG. 1B (e.g., substantially similar or identical). In representative embodiments, the HaHB11 polypeptide does not comprise the N-terminal domain, the homeodomain and/or the leucine zipper domain (the location of these domains is shown in FIG. 1B). In embodiments, the HaHB11 polypeptide binds in vitro and/or in vivo to the pseudopalindromic sequence CAAT(A/T)ATTG (SEQ ID NO:7).

In representative embodiments, the HaHB11 polypeptide comprises the homeodomain, leucine zipper, the transactivation site, and/or putative protein-kinase phosphorylation site domains (see, schematic in FIG. 1B), Unless indicated otherwise, the HaHB11 polypeptide can be a fusion protein. For example, it may be useful to express the HaHB11 polypeptides as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the protein may be produced, e.g., fusion proteins comprising maltose binding protein (MBP) or glutathione-S-transferase. As another alternative, the fusion protein can comprise a reporter molecule. HaHB11 is a transcription factor and HaHB11 fusion proteins can also be generated for use in yeast two-hybrid systems (e.g., GAL4-HaHB11 fusions), as is known in the art.

It will further be understood that the HaHB11 polypeptides specifically disclosed herein will typically tolerate substitutions in the amino acid sequence and substantially retain biological activity. To routinely identify biologically active HaHB11 polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding the HaHB11 polypeptide.

In making amino acid substitutions, the hydropathic index of amino acids can be considered. The importance of the hydropathic amino acid index in conferring interactive biologic function on a protein is generally understood in the art (see, Kyte et al., J. Mol. Biol. 157:105 (1982)). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte et al., Id.), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

The HaHB11 polypeptides of the present invention also encompass HaHB11 polypeptide fragments (optionally, biologically active HaHB11 fragments), and equivalents thereof (optionally, biologically active equivalents). The length of the HaHB11 fragment is not critical. Illustrative functional HaHB11 protein fragments comprise at least about 50, 75, 100, 125, 150, 160, 165, 170, 171, 172, 173 or 174 amino acids (optionally, contiguous amino acids) of a HaHB11 polypeptide. In representative embodiments, the HaHB11 polypeptide comprises the homeodomain, leucine zipper, the transactivation site, and/or the putative protein-kinase phosphorylation site domains (see, schematic in FIG. 1B), and optionally any sequence variability occurs outside of this region(s). In representative embodiments, the HaHB11 comprises the first, second, third and/or fourth casein-phosphorylation site (numbering with respect to the N-terminus; FIG. 1B), and optionally any variability occurs outside this domain. In representative embodiments, the HaHB11 polypeptide comprises the N-terminal region (see FIG. 1B) and, optionally, any sequence variation occurs outside this domain. In additional representative embodiments, the HaHB11 polypeptide comprises the C-terminal domain (FIG. 1B) and; optionally, any sequence variability occurs outside of this region. In representative embodiments, the homeodomain, leucine zipper, transactivation site, protein kinase phosphorylation site, casein phosphorylation sites, N-terminal domain and/or C-terminal domain have the sequence(s) as shown in FIG. 1B. In additional embodiments, the sequence is an equivalent of the sequence as shown in FIG. 1B (e.g., substantially similar or identical). In representative embodiments, the HaHB11 polypeptide does not comprise the N-terminal domain, the homeodomain and/or the leucine zipper domain (location of these domains shown in FIG. 1B). In embodiments, the HaHB11 polypeptide binds in vitro and/or in vivo to the pseudopalindromic sequence CAAT(A/T)ATTG (SEQ ID NO:7).

In representative embodiments, equivalents of the HaHB11 polypeptides (including variants and fragments) retain one, two, three, four or all five of the leucines in the leucine zipper region of SEQ ID NO:3 (see, FIG. 1B).

In representative embodiments, equivalents of the HaHB11 polypeptides (including variants and fragments) retain one, two, three, four or all five of the leucines in the leucine zipper region of SEQ ID NO:10 (amino acid residues 111-175 of SEQ ID NO:10).

In representative embodiments, the invention provides an isolated HaHB11 polypeptide comprising, consisting essentially of, or consisting of an amino acid sequence selected from the group consisting of: (a) the amino acid sequence of SEQ ID NO:3; (b) an amino acid sequence having at least about 60%, 70%, 75%, 80%, 85%, 90%, 95%, 97%, 98%, 99% or more amino acid sequence identity or similarity with the amino acid sequence of SEQ ID NO:3, optionally wherein the HaHB11 polypeptide is biologically active; and (c) a fragment of at least about 50, 60, 70, 80, 90, 100, 110, 120, 130, 140, 150, 155, 160, 171, 172, 173 or 174 amino acids of the amino acid sequence of (a) or (b) above, optionally wherein the fragment is biologically active.

In representative embodiments, the invention provides an isolated HaHB11 polypeptide comprising, consisting essentially of, or consisting of an amino acid sequence selected from the group consisting of: (a) the amino acid sequence of SEQ ID NO:10; (b) an amino acid sequence having at least about 96%, 97%, 98%, 99% or more amino acid sequence identity or similarity with the amino acid sequence of SEQ ID NO:10, optionally wherein the HaHB11 polypeptide is biologically active; and (c) a fragment comprising amino acids 15 to 30, or 145 to 160 of SEQ ID NO:10 that is at least about 50, 60, 70, 80, 90, 100, 110, 120, 130, 140, 150, 155, 160, 171, 172, 173 or 174 amino acids of the amino acid sequence of (a) or (b) above, optionally wherein the fragment is biologically active.

In representative embodiments, the invention provides an isolated HaHB11 polypeptide comprising, consisting essentially of, or consisting of an amino acid sequence selected from the group consisting of: (a) the amino acid sequence of SEQ ID NO:11, SEQ ID NO:12; SEQ ID NO:13, SEQ ID NO:14, or SEQ ID NO:15; (b) an amino acid sequence having at least about 96%, 97%, 98%, 99% or more amino acid sequence identity or similarity with the amino acid sequence of SEQ ID NO:11, SEQ ID NO:12; SEQ ID NO:13, SEQ ID NO:14, or SEQ ID NO:15, optionally wherein the HaHB11 polypeptide is biologically active; and (c) a fragment comprising amino acids 140 to 155 of SEQ ID NO:11, amino acids 140 to 155 of SEQ ID NO:12, amino acids 150 to 165 of SEQ ID NO:13, amino acids 80 to 95 of SEQ ID NO:14, amino acids 150 to 165 of SEQ ID NO:14, amino acids 125 to 140 of SEQ ID NO:15, or amino acids 150 to 165 of SEQ ID NO:15 that is at least about at least about 50, 60, 70, 80, 90, 100, 110, 120, 130, 140, 150, 155, 160, 171, 172, 173 or 174 amino acids of the amino acid sequence of (a) or (b) above, optionally wherein the fragment is biologically active.

The invention further provides antibodies and antibody fragments that specifically bind to the HaHB11 polypeptides of the invention.

The term "antibody" or "antibodies" as used herein refers to all types of immunoglobulins, including IgG, IgM, IgA, IgD, and IgE. The antibody can be monoclonal or polyclonal and can be of any species of origin, including for example mouse, rat, rabbit, horse, goat, sheep or human, or can be a chimeric, humanized or human antibody. See, e.g., Walker et al., Molec. Immunol. 26:403-411 (1989). The antibodies can be recombinant monoclonal antibodies produced according to the methods disclosed in U.S. Pat. No. 4,474,893 or 4,816,567. The antibodies can also be chemically constructed according to the method disclosed in U.S. Pat. No. 4,676,980.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., Science 254:1275-1281 (1989)).

Monoclonal antibodies according to the present invention can be produced in a hybridoma cell line according to the technique of Kohler et al., Nature 265:495-97 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, Science 246:1275-1281 (1989).

Antibodies specific to a target polypeptide can also be obtained by phage display techniques known in the art.

The invention also provides nucleic acids encoding the HaHB11 polypeptides of the invention, optionally a biologically active HaHB11 polypeptide. The nucleic acid can be from any plant species of origin (e.g., *Helianthus annuus*) or can be partially or completely synthetic. In representative embodiments, the nucleic acid encoding the HaHB11 polypeptide is an isolated nucleic acid.

HaHB11 orthologs from other organisms, in particular other plants, can be routinely identified using methods known in the art (e.g., orthologs from species belonging to the Asteraceae family [also known as the Compositae family], such as a species of lettuce). For example, PCR and other amplification techniques and hybridization techniques can be used to identify such orthologs based on their sequence similarity to the sequences set forth herein.

In representative embodiments, the invention encompasses polynucleotides encoding the HaHB11 polypeptides of the invention having substantial nucleotide sequence identity with the polynucleotides specifically disclosed herein encoding HaHB11 (e.g., SEQ ID NO:1, nucleotides 7-944 of SEQ ID NO:1, and SEQ ID NO:2), or fragments thereof, and which encode a HaHB11 polypeptide (including fragments), optionally a biologically active HaHB11 polypeptide. In some embodiments, the polynucleotides encoding the HaHB11 polypeptides have substantial nucleotide sequence identity with the polynucleotides of SEQ ID NO:9, or fragments thereof, and which encode a HaHB11 polypeptide (including fragments), optionally a biologically active HaHB11 polypeptide.

The invention also provides polynucleotides encoding the HaHB11 polypeptides of the invention, wherein the polynucleotide hybridizes to the complete complement of the HaHB11 nucleic acid sequences specifically disclosed herein (e.g., SEQ ID NO:1, nucleotides 7-944 of SEQ ID NO:1, and SEQ ID NO:2), or fragments thereof, under stringent hybridization conditions as known by those skilled in the art and encode a HaHB11 polypeptide (including fragments), optionally a biologically active HaHB11 polypeptide. In some embodiments, the polynucleotide hybridizes to nucleotides 50 to 70, 430 to 450, 600 to 620, or 731 to 751 of SEQ ID NO:9, or fragments thereof, under stringent hybridization conditions and encode a HaHB11 polypeptide (including fragments), optionally a biologically active HaHB11 polypeptide. Further, it will be appreciated by those skilled in the art that there can be variability in the polynucleotides that encode the HaHB11 polypeptides of the present invention due to the degeneracy of the genetic code. The degeneracy of the genetic code, which allows different nucleotide sequences to code for the same protein, is well known in the art. Moreover, plant or species-preferred codons can be used in the polynucleotides encoding the HaHB11 polypeptides of the invention, as is also well-known in the art.

The invention also provides polynucleotides encoding fragments of a full-length HaHB11 polypeptide, optionally biologically active fragments. Exemplary polynucleotides encoding HaHB11 fragments comprise at least about at least about 50, 75, 100, 125, 150, 175, 200, 225, 250, 275, 300, 325, 350, 375, 400, 425, 450, 475, 500, 505, 510, 515 or 520 or more nucleotide bases (optionally, contiguous bases) of a polynucleotide encoding a full-length HaHB11 polypeptide.

In exemplary, but non-limiting, embodiments, the invention provides a nucleic acid (e.g., recombinant or isolated) comprising, consisting essentially of, or consisting of a nucleotide sequence encoding a HaHB11 polypeptide, the nucleotide sequence selected from the group consisting of: (a) a nucleotide sequence comprising the nucleotide sequence of SEQ ID NO:1, nucleotides 7-944 of SEQ ID NO:1, or SEQ ID NO:2; (b) a nucleotide sequence comprising at least about 50, 75, 100, 125, 150, 175, 200, 225, 250, 275, 300, 325, 350, 375, 400, 425, 450, 475, 500, 505, 510, 515 or 520 or more consecutive nucleotides of the nucleotide sequence of SEQ ID NO:1, nucleotides 7-944 of SEQ ID NO:1, or SEQ ID NO:2 (e.g., encoding a fragment, optionally a functional fragment of SEQ ID NO:3); (c) a nucleotide sequence having at least about 60%, 70%, 75%, 80%, 85%, 90%, 95%, 97%, 98%, 99% or more sequence identity to the nucleotide sequence of (a) or (b); (d) a nucleotide sequence that hybridizes to the complete complement of the nucleotide sequence of (a) or (b) under stringent hybridization conditions; and (e) a nucleotide sequence that differs from the nucleotide sequence of any of (a) to (d) due to the degeneracy of the genetic code. In representative embodiments, the nucleotide sequence encodes a biologically active HaHB11 polypeptide (including biologically active fragments of a full-length HaHB11 polypeptide).

In additional exemplary, but non-limiting, embodiments, the invention provides a nucleic acid (e.g., recombinant or isolated) comprising, consisting essentially of, or consisting of a nucleotide sequence encoding a HaHB11 polypeptide, the nucleotide sequence selected from the group consisting of: (a) a nucleotide sequence comprising the nucleotide sequence of SEQ ID NO:9 or nucleotides 174 to 190, 550 to 575, 725 to 740, or 830 to 860 of SEQ ID NO:9; (b) a nucleotide sequence comprising at least about 50, 75, 100, 125, 150, 175, 200, 225, 250, 275, 300, 325, 350, 375, 400, 425, 450, 475, 500, 505, 510, 515 or 520 or more consecutive nucleotides of the nucleotide sequence of SEQ ID NO:9 that include at least one sequence selected from nucleotides 50 to 70, 430 to 450, 600 to 620 or 731 to 751 of SEQ ID NO:9 (e.g., encoding a fragment, optionally a functional fragment of SEQ ID NO:9); (c) a nucleotide sequence having at least about 90%, 95%, 96%, 97%, 98%, 99% or more sequence identity to the nucleotide sequence of (a) or (b); and (d) a nucleotide sequence that differs from the nucleotide sequence of any of (a) to (c) due to the degeneracy of the genetic code. In representative embodiments, the nucleotide sequence encodes a biologically active HaHB11 polypeptide (including biologically active fragments of a full-length HaHB11 polypeptide).

In representative embodiments, the nucleotide sequence encodes the polypeptide of SEQ ID NO:3, or an equivalent polypeptide having substantial amino acid sequence identity or similarity with SEQ ID NO:3 (optionally, a biologically active equivalent). In representative embodiments, the nucleotide sequence encodes an equivalent (optionally, a biologically active equivalent) of the polypeptide of SEQ ID NO:3 and hybridizes to the complete complement of nucleotide sequence of SEQ ID NO:1, nucleotides 7-944 of SEQ ID NO:1, or SEQ ID NO:2 under stringent hybridization conditions.

In additional representative embodiments, the nucleotide sequence encodes the polypeptide of SEQ ID NO:10, or an equivalent polypeptide having substantial amino acid sequence identity or similarity with SEQ ID NO:10 (optionally, a biologically active equivalent). In representative embodiments, the nucleotide sequence encodes an equivalent (optionally, a biologically active equivalent) of the polypeptide of SEQ ID NO:10 and hybridizes to the complete complement of nucleotide sequence of nucleotides 50 to 70, 430 to 450, 600 to 620, or 731 to 751 of SEQ ID NO:9, under stringent hybridization conditions.

In representative embodiments, the nucleotide sequence encodes the polypeptide of SEQ ID NO:3. According to this embodiment, the nucleotide sequence can comprise, consist essentially of, or consist of SEQ ID NO:1, nucleotides 7-944 of SEQ ID NO:1, or SEQ ID NO:2. Also according to this embodiment, the nucleotide sequence can comprise, consist essentially of, or consist of a sequence that is distinct from that of SEQ ID NO:2, but encodes the polypeptide of SEQ ID NO:3 due to the degeneracy of the genetic code. In representative embodiments, the nucleotide sequence encodes a biologically active HaHB11 polypeptide In other representative embodiments, the nucleotide sequence encodes the polypeptide of SEQ ID NO:10. Also according to this embodiment, the nucleotide sequence can comprise, consist essentially of, or consist of a sequence that is distinct from that of SEQ ID NO:9, but encodes the polypeptide of SEQ ID NO:10 due to the degeneracy of the genetic code. In other representative embodiments, the nucleotide sequence encodes the polypeptide of SEQ ID NO:11, SEQ ID NO:12, SEQ ID NO:13, SEQ ID NO:14 or SEQ ID NO:15.

Those skilled in the art will appreciate that both the homeodomain and leucine zipper motifs (HD-Zip) are functionally conserved and interchangeable among HD-Zip I proteins. Accordingly, in representative embodiments, the HaHB11 polypeptide comprises (i) a HD-Zip domain (e.g., from an HD-Zip protein) that optionally binds CAAT(A/T)ATTG (SEQ ID NO:7) and (ii) amino acids 111 to 175 of SEQ ID NO:3 or an amino acid sequence that is substantially similar or identical thereto. In embodiments of the invention, one, two three, four or all five of the leucines in the leucine zipper region of SEQ ID NO:3 (see, FIG. 1B) are conserved. Optionally, the HaHB11 polypeptide further comprises amino acids 1 to 14 of SEQ ID NO:3 or an amino acid sequence that is substantially similar or identical thereto. In embodiments of the invention, the HaHB11 polypeptide is biologically active.

In additional representative embodiments, the HaHB11 polypeptide comprises (i) a HD-Zip domain (e.g., from an HD-Zip protein) that optionally binds CAAT(A/T)ATTG (SEQ ID NO:7) and (ii) amino acids 114 to 181 of SEQ ID NO:10 or an amino acid sequence that is substantially similar or identical thereto. In embodiments of the invention, one, two three, four or all five of the leucines in the leucine zipper region of SEQ ID NO:10 are conserved. Optionally, the HaHB11 polypeptide further comprises amino acids 1 to 14 of SEQ ID NO:10 or an amino acid sequence that is substantially similar or identical thereto. In embodiments of the invention, the HaHB11 polypeptide is biologically active.

In additional representative embodiments, the HaHB11 polypeptide comprises (i) a HD-Zip domain (e.g., from an HD-Zip protein) that optionally binds CAAT(A/T)ATTG (SEQ ID NO:7) and (ii) amino acids amino acids 114 to 180 of SEQ ID NO:11, amino acids 111 to 179 of SEQ ID NO:12; amino acids 111 to 177 of SEQ ID NO:13, amino acids 113 to 183 of SEQ ID NO:14, amino acids 112 to 186 of SEQ ID NO:15, or an amino acid sequence that is substantially similar or identical thereto. In embodiments of the invention, one, two three, four or all five of the leucines in the leucine zipper region of SEQ ID NO:11, SEQ ID NO:12, SEQ ID NO:13, SEQ ID NO:14 or SEQ ID NO:15, respectively, are conserved. Optionally, the HaHB11 polypeptide further comprises amino acids 1 to 14 of SEQ ID NO:12, amino acids 1 to 14 of SEQ ID NO:14 or amino acids 1 to 14 of SEQ ID NO:15 or an amino acid sequence that is substantially similar or identical thereto. In embodiments of the invention, the HaHB11 polypeptide is biologically active.

In further representative embodiments, the HaHB11 polypeptide comprises (i) a HD-Zip domain having an amino acid sequence selected from: amino acids amino acids 15 to 110 of SEQ ID NO:3, 15 to 113 of SEQ ID NO:10, 15 to 113 of SEQ ID NO:11, amino acids 15 to 110 of SEQ ID NO:12; amino acids 15 to 110 of SEQ ID NO:13, amino acids 15 to 112 of SEQ ID NO:14 and amino acids 15 to 111 of SEQ ID NO:15, or an amino acid sequence that is substantially similar or identical thereto.

In other representative embodiments, the homeodomain of the HaHB11 protein (e.g., amino acids 15 to 74 or SEQ ID NO:3 or an equivalent thereof) is replaced with a heterologous homeodomain. For example, the HaHB11 polypeptide can comprise (i) a HD domain (e.g., from an HD-Zip protein); and (ii) amino acids 75 to 175 of SEQ ID NO:3 or an amino acid sequence that is substantially similar or identical to amino acids 75 to 175 of SEQ ID NO:3, wherein the HaHB11 polypeptide optionally binds CAAT (A/T)ATTG (SEQ ID NO:7). In another example, the HaHB11 polypeptide can comprise (i) a HD domain (e.g., from an HD-Zip protein); and (ii) amino acids 78 to 181 of SEQ ID NO:10 or an amino acid sequence that is substantially similar or identical to amino acids 78 to 181 of SEQ ID NO:10, wherein the HaHB11 polypeptide optionally binds CAAT(A/T)ATTG (SEQ ID NO:7). In another example, the HaHB11 polypeptide can comprise (i) a HD domain (e.g., from an HD-Zip protein); and (ii) amino acids 78 to 181 of SEQ ID NO:11, amino acids 75 to 179 of SEQ ID NO:12, amino acids 75 to 177 of SEQ ID NO:13, amino acids 76 to 186 of SEQ ID NO:15, or an amino acid sequence that is substantially similar or identical thereto, wherein the HaHB11 polypeptide optionally binds CAAT (A/T)ATTG (SEQ ID NO:7) In embodiments of the invention, one, two three, four or all five of the leucines in the leucine zipper region are conserved. Optionally, the HaHB11 polypeptide further comprises amino acids 1 to 14 of SEQ ID NO:3 or an amino acid sequence that is substantially similar or identical thereto. Alternatively, the HaHB11 polypeptides optionally further comprises amino acids 1 to 14 of SEQ ID NO:14 or SEQ ID NO:15, or an amino acid sequence that is substantially similar or identical thereto. In embodiments of the invention, the HaHB11 polypeptide is biologically active.

In other representative embodiments, the leucine zipper region (e.g., amino acids 76 to 110 of SEQ ID NO:3 or an equivalent thereof) is replaced with a heterologous leucine zipper. For example, the HaHB11 polypeptide can comprise (i) amino acids 15 to 74 of SEQ ID NO:3 or an amino acid sequence that is substantially similar or identical thereto; (ii) a leucine zipper domain (e.g., from an HD-Zip protein); and (iii) amino acids 111 to 175 of SEQ ID NO:3 or an amino acid sequence that is substantially similar or identical thereto, wherein the HaHB11 polypeptide optionally binds CAAT(A/T)ATTG (SEQ ID NO:7). In another example, the HaHB11 polypeptide can comprise (i) amino acids 15 to 77 of SEQ ID NO:10 or an amino acid sequence that is substantially similar or identical thereto; (ii) a leucine zipper domain (e.g., from an HD-Zip protein); and (iii) amino acids 116 to 180 of SEQ ID NO:10 or an amino acid sequence that is substantially similar or identical thereto, wherein the HaHB11 polypeptide optionally binds CAAT(A/T)ATTG (SEQ ID NO:7). Optionally, the HaHB11 polypeptide further comprises amino acids 1 to 14 of SEQ ID NO:3 or an amino acid sequence that is substantially similar or identical thereto. In embodiments of the invention, the HaHB11 polypeptide is biologically active.

In other representative embodiments, the leucine zipper region of proteins having the amino acid sequence of SEQ ID NO:11, SEQ ID NO:12, SEQ ID NO:13, SEQ ID NO:14 or SEQ ID NO:15 (i.e., amino acids 78-113 of SEQ ID NO:11, amino acids 75-110 of SEQ ID NO:12, amino acids 75-110 of SEQ ID NO:13, amino acids 77 to 112 of SEQ ID NO:14 or amino acids 76 to 111 of SEQ ID NO:15 or an equivalent thereof) is replaced with a heterologous leucine zipper.

In additional embodiments, the N-terminal region (e.g., amino acids 1 to 14 of SEQ ID NO:3 or an equivalent thereof) is replaced with a heterologous N-terminal region from a HD-Zip protein. For example, the HaHB11 polypeptide can comprise (i) an N-terminal domain from an HD-Zip protein; and (ii) amino acids 15 to 175 of SEQ ID NO:3 or an amino acid sequence that is substantially similar or identical thereto, wherein the HaHB11 polypeptide optionally binds CAAT(A/T)ATTG (SEQ ID NO:7). In another example, the HaHB11 polypeptide can comprise (i) an N-terminal domain from an HD-Zip protein; and (ii) amino acids 15 to 77 of SEQ ID NO:10 or an amino acid sequence that is substantially similar or identical thereto, wherein the HaHB11 polypeptide optionally binds CAAT(A/T)ATTG (SEQ ID NO:7). In another example, the HaHB11 polypeptide can comprise (i) an N-terminal domain from an HD-Zip protein; and (ii) amino acids 15 to 74 of SEQ ID NO:12 or amino acids 15 to 74 of SEQ ID NO:13, or an amino acid sequence that is substantially similar or identical thereto, wherein the HaHB11 polypeptide optionally binds CAAT(A/T)ATTG (SEQ ID NO:7). In embodiments of the invention, the HaHB11 polypeptide is biologically active.

In embodiments of the invention, the C-terminal region (e.g., amino acids 111 to 175 of SEQ ID NO:3 or an equivalent thereof) is replaced with a heterologous C-terminal region from a HD-Zip protein. For example, the HaHB11 polypeptide can comprise: (i) amino acids 1 to 110 of SEQ ID NO:3 or an amino acid sequence that is substantially similar or identical thereto; and (ii) a C-terminal domain from an HD-Zip protein, wherein the HaHB11 polypeptide optionally binds CAAT(A/T)ATTG (SEQ ID NO:7). In another example, the HaHB11 polypeptide can comprise: (i) amino acids 1 to 113 of SEQ ID NO:10 or an amino acid sequence that is substantially similar or identical thereto; and (ii) a C-terminal domain from an HD-Zip protein, wherein the HaHB11 polypeptide optionally binds CAAT(A/T)ATTG (SEQ ID NO:7). In another example, the HaHB11 polypeptide can comprise: (i) amino acids 1 to 113 of SEQ ID NO:11, 1 to 110 of SEQ ID NO:12; 1 to 110 of SEQ ID NO:13, 1 to 112 of SEQ ID NO:14, 1 to 111 of SEQ ID NO:15, or an amino acid sequence that is substantially similar or identical thereto; and (ii) a C-terminal domain from an HD-Zip protein, wherein the HaHB11 polypeptide optionally binds CAAT(A/T)ATTG (SEQ ID NO:7). In embodiments of the invention, the HaHB11 polypeptide is biologically active.

The invention also provides nucleic acids comprising one or more HaHB11 expression control elements. In representative embodiments, the nucleic acid comprises, consists essentially of, or consists of a HaHB11 promoter of the invention (including fragments thereof). The term "HaHB11 promoter" is intended to encompass a full-length promoter, and equivalents thereof (optionally, a biologically active equivalent) that have substantially identical nucleotide sequences to the HaHB11 promoter sequences specifically disclosed herein, as well as fragments of a full-length HaHB11 promoter (optionally, a biologically active fragment) and equivalents thereof (optionally, a biologically active equivalent) that have substantially identical nucleotide sequences to a fragment of HaHB11 promoter sequences specifically disclosed herein. The term "HaHB11 promoter" includes sequences from *Helianthus annuus* as well as orthologs from other plant species, including naturally occurring allelic variants, isoforms, splice variants, and the like, or can be partially or completely synthetic.

Orthologs from other organisms, in particular other plants, can be routinely identified using methods known in the art. For example, PCR and other amplification techniques and hybridization techniques can be used to identify such orthologs based on their sequence similarity to the sequences set forth herein.

Biological activities associated with the HaHB11 promoter include, without limitation, the ability to control or regulate transcription of an operably associated coding sequence. Another non-limiting biological activity includes the ability to bind one or more transcription factors and/or RNA polymerase II. Other biological activities include the ability to be induced in the same manner as a wild-type HaHB11 promoter, e.g., the ability to be induced by abiotic stress and/or ABA.

Thus, in exemplary embodiments, the isolated nucleic acid comprises, consists essentially of, or consists of the nucleotide sequence of SEQ ID NO:4, SEQ ID NO:5, SEQ ID NO:6 or an equivalent of any of the foregoing (optionally, a biologically active equivalent).

In other exemplary embodiments, the isolated nucleic acid comprises, consists essentially of, or consists of the nucleotide sequence of SEQ ID NO:16 or an equivalent of any of the foregoing (optionally, a biologically active equivalent). In a particular embodiment, the isolated nucleic acid consists of the nucleotide sequence of SEQ ID NO:16.

Equivalents of the HaHB11 promoters of the invention encompass polynucleotides having substantial nucleotide sequence identity with the HaHB11 promoter sequences specifically disclosed herein (e.g., SEQ ID NO:4, SEQ ID NO:5 or SEQ ID NO:6) or fragments thereof, for example at least about 60%, 70%, 75%, 80%, 85%, 90%, 95%, 97%, 98% or 99% or more, and are optionally biologically active. In representative embodiments, there is no sequence variability in the TATA box, CAAT box, LTRE element, DRE element and/or ABRE element (see, e.g., the schematic in FIG. 1A), i.e., these sequences are conserved and any sequence variability falls outside these regions.

The HaHB11 promoters of the invention also include polynucleotides that hybridize to the complete complement of the HaHB11 promoter sequences specifically disclosed herein (e.g., SEQ ID NO:4, SEQ ID NO:5 or SEQ ID NO:6) or fragments thereof under stringent hybridization conditions as known by those skilled in the art and are optionally biologically active.

In exemplary embodiments, the isolated nucleic acid comprises, consists essentially of, or consists of the nucleotide sequence of SEQ ID NO:4, SEQ ID NO:5, SEQ ID NO:6

In other embodiments, the HaHB11 promoters of the invention encompass portions of the endogenous HaHB11 promoter having substantial nucleotide sequence identity with the HaHB11 promoter having the sequence of SEQ ID NO:16, fragments thereof, for example at least about 60%, 70%, 75%, 80%, 85%, 90%, 95%, 97%, 98% or 99% or more, and are optionally biologically active. In specific embodiments the HaHB11 promoters of the invention encompass polynucleotides having substantial nucleotide sequence identity with nucleotides 1 to 800 or 1 to 500 of the HaHB11 long promoter (SEQ ID NO:16), or fragments thereof of at least 50, 100 or 150 nucleotides in length, for example at least about 60%, 70%, 75%, 80%, 85%, 90%, 95%, 97%, 98% or 99% or more, and are optionally biologically active. In representative embodiments, there is no sequence variability in the LTRE element, DRE element and/or ABRE element.

The HaHB11 promoters of the invention also include portions of the endogenous HaHB11 promoter that hybridize to the complete complement of nucleotides 1 to 800 or 1 to 500 of the HaHB11 long promoter (SEQ ID NO:16). The HaHB11 promoters of the invention also include portions of the endogenous HaHB11 promoter that hybridize to the complete complement of fragments of the HaHB11 long promoter (SEQ ID NO:16) of at least 50, 100 or 150 nucleotides in length under stringent hybridization conditions. In particular embodiments, the HaHB11 promoters of the invention hybridize to nucleotides 250 to 280 of SEQ ID NO:16 under stringent hybridization conditions.

The HaHB11 promoter sequences encompass fragments (optionally, active fragments) of the HaHB11 promoter sequences specifically disclosed herein (e.g., SEQ ID NO:4, SEQ ID NO:5 or SEQ ID NO:6) and equivalents thereof. Illustrative fragments comprise at least about 50, 60, 75, 100, 125, 150, 175, 200, 225, 250, 275, 300, 325, 350, 375, 400 or more nucleotides (optionally, contiguous nucleotides) of the fall-length sequence.

The HaHB11 promoter sequences encompass fragments (optionally, biologically active fragments) of the HaHB11 long promoter sequence disclosed herein (SEQ ID NO:16) and equivalents thereof. Illustrative fragments comprise at least about 50, 60, 75, 100, 125, 150, 175, 200, 225, 250, 275, 300, 325, 350, 375, 400 or more nucleotides (optionally, contiguous nucleotides) of nucleotides 1 to 800 of SEQ ID NO:16). In particular embodiments, the promoter sequences encompass nucleotides 1 to 200, 200 to 400, 400 to 600, or 600 to 800 of SEQ ID NO:16 and comprise at least about 225, 250, 275, 300, 325, 350, 375, 400, 500, 700, 1,000, 1,250 or more nucleotides (optionally, contiguous nucleotides) of the sequence of SEQ ID NO:16.

In representative embodiments, the HaHB11 promoter sequence comprises the TATA box sequence, the CAAT box sequence, the LTRE (Low Temperature Responsive Element; located at position 259 of SEQ ID NO:4 (−290 bp from the Transcription initiation Site (−strand)), the DRE (Dehydration Responsive Element; located at position 259 of SEQ ID NO:4 (−strand), and/or the ABRE (ABA Responsive Element; located at −266 of SEQ ID NO:4 (−strand).

In representative embodiments, the HaHB11 promoter sequence comprises the LTRE sequence at position 1158 of SEQ ID NO:16, the ABRE-like sequence at position 1165 bp of SEQ ID NO:16; the ABRE-related sequences at positions 864 and 1164 of SEQ ID NO:16; the DRE core at position 1158 of SEQ ID NO:16, and/or the ANAERO2CONSENSUS at position 243 of SEQ ID NO:16).

In embodiments of the invention, the nucleic acid comprising the HaHB11 promoter does not include any of the HaHB11 coding sequence.

Accordingly, in representative embodiments, the invention provides a nucleic acid (e.g., a recombinant or isolated nucleic acid) comprising, consisting essentially of, or consisting of a nucleotide sequence selected from the group consisting of: (a) SEQ ID NO:4, SEQ ID NO:5 or SEQ ID NO:6; (b) a nucleotide sequence comprising at least about 50, 60, 75, 100, 125, 150, 175, 200, 225, 250, 275, 300, 325, 350, 375, 400 or more nucleotides (optionally, contiguous nucleotides) of SEQ ID NO:4, SEQ ID NO:5 of SEQ ID NO:6; (c) a nucleotide sequence that hybridizes to the complete complement of the nucleotide sequence of (a) or (b) under stringent hybridization conditions; and (d) a nucleotide sequence having at least about 60%, 70%, 75%, 80%, 85%, 90%, 95%, 97%, 98%, 99% sequence identity to the nucleotide sequences of any of (a) to (c). In representative embodiments, the nucleotide sequence is a biologically active promoter sequence (e.g., has promoter activity) and is optionally induced by abiotic stress.

Accordingly, in representative embodiments, the invention provides a nucleic acid (e.g., a recombinant or isolated nucleic acid) comprising, consisting essentially of the nucleotide sequence of: (a) SEQ ID NO:16; (b) nucleotides 1 to 200, 200 to 400, 400 to 600, or 600 to 800 of SEQ ID NO:10 and comprise at least about 225, 250, 275, 300, 325, 350, 375, 400 or more nucleotides (optionally, contiguous nucleotides) of the sequence of SEQ ID NO:16; (c) a nucleotide sequence that hybridizes to the complete complement of the nucleotide sequence of (b) under stringent hybridization conditions; and (d) a nucleotide sequence having at least about 60%, 70%, 75%, 80%, 85%, 90%, 95%, 97%, 98%, 99% sequence identity to the nucleotide sequences of any of (a) to (c). In representative embodiments, the nucleotide sequence is a biologically active promoter sequence (e.g., has promoter activity) and is optionally induced by abiotic stress.

In embodiments of the invention, the nucleotide sequence comprises, consists essentially of, or consists of the nucleotide sequence of SEQ ID NO:4, SEQ ID NO:5 or SEQ ID NO:6.

In embodiments, the HaHB11 promoter sequence of the invention is operably associated with a nucleotide sequence of interest, which is optionally a heterologous nucleotide sequence of interest. According to this embodiment, the HaHB11 controls or regulates expression (e.g., transcription and, optionally, translation) of the nucleotide sequence of interest.

The invention further provides expression cassettes. In general, the expression cassettes of the invention are of two general types.

First, the invention provides an expression cassette comprising a HaHB11 nucleic acid encoding a HaHB11 polypeptide of the invention operably associated with a promoter. In embodiments, the nucleic acid encoding the HaHB11 polypeptide is operably associated with a HaHB11 promoter sequence of the invention. In embodiments, the nucleic acid encoding the HaHB11 polypeptide is operably associated with a heterologous promoter.

The heterologous promoter can be any suitable promoter known in the art (including bacterial, yeast, fungal, insect, mammalian, and plant promoters). In particular embodiments, the promoter is a promoter for expression in plants. The selection of promoters useable with the present invention can be made among many different types of promoters. Thus, the choice of promoter depends upon several factors, including, but not limited to, cell- or tissue-specific expression, desired expression level, efficiency, inducibility and/or selectability. For example, where expression in a specific tissue or organ is desired in addition to inducibility, a tissue-specific promoter can be used (e.g., a root specific promoter). In contrast, where expression in response to a stimulus is desired a promoter inducible by other stimuli or chemicals can be used. Where continuous expression is desired throughout the cells of a plant, a constitutive promoter can be chosen.

Non-limiting examples of constitutive promoters include cestrum virus promoter (cmp) (U.S. Pat. No. 7,166,770), an actin promoter (e.g., the rice actin 1 promoter; Wang et al., Mol. Cell. Biol. 12:3399-3406 (1992); as well as U.S. Pat. No. 5,641,876), Cauliflower Mosaic Virus (CaMV) 35S promoter (Odell et al., Nature 313:810-812 (1985)), CaMV 19S promoter (Lawton et al., Plant Mol. Biol. 9:315-324 (1987)), an opine synthetase promoter (e.g., nos, mas, ocs, etc.; (Ebert et al., PNAS 84:5745-5749 (1987)), Adh promoter (Walker et al., PNAS 84:6624-6629 (1987)), sucrose synthase promoter (Yang & Russell, PNAS 87:4144-4148 (1990)), and a ubiquitin promoter.

In some embodiments, the expression cassettes of the invention can further comprise enhancer elements and/or tissue preferred elements in combination with the promoter. In some embodiments, the expression cassette comprises a constitutive S35 promoter operably associated with a polynucleotide sequence encoding HaHB11 having the amino acid sequence of SEQ ID NO:3. In some embodiments, the expression cassette comprises a constitutive S35 promoter operably associated with a polynucleotide sequence encoding HaHB11 having the amino acid sequence of SEQ ID NO:10. In some embodiments, the expression cassette comprises a constitutive S35 promoter operably associated with a polynucleotide sequence encoding HaHB11 having the amino acid sequence of SEQ ID NO:11, SEQ ID NO:12, SEQ ID NO:13, SEQ ID NO:14 or SEQ ID NO:15.

In some embodiments, the heterologous promoter is a promoter for expression in a monocot plant. In further embodiments the heterologous promoter is selected from: ZmUbi1 (Ubiquitin), Act1 (Actin), OsTubA1, (Tubulin), OsCc1 (Cytochrome c), rubi3 (polyubiquitin), APX (ascorbate peroxidase), SCP1, PGD1 (phosphogluconate dehydrogenase), R1G1B (early drought induced protein) and EIF5 (translation initiation factor).

In some embodiments, the heterologous promoter is a promoter for expression in a dicot plant. In further embodiments the heterologous promoter is a CsVMV (cassava vein mosaic virus) or ScBV (sugarcane *bacilliform badnavirus*) promoter. In other embodiments, the heterologous promoter is an CaMV 35S promoter.

Some non-limiting examples of tissue-specific promoters useable with the present invention include those driving the expression of seed storage proteins (e.g., 13-conglycinin, cruciferin, napin phaseolin, etc.), zein or oil body proteins (such as oleosin), or proteins involved in fatty acid biosynthesis (including acyl carrier protein, stearoyi-ACP desaturase and fatty acid desaturases (fad 2-1)), and other nucleic acids expressed during embryo development (such as Bce4, see, e.g., Kridl et al., Seed Sci. Res. 1:209-219 (1991); as well as EP Patent No. 255378). Thus, the promoters associated with these tissue-specific nucleic acids can be used in the present invention.

Additional examples of tissue-specific promoters usable with the present invention include, but are not limited to, the root-specific promoters RCc3 (Jeong et al., Plant Physiol. 153:185-197 (2010)) and RB7 (U.S. Pat. No. 5,459,252), the lectin promoter (Lindstrom et al., Der. Genet. 11:160-167 (1990); and Vodkin et al., Prog. Clin. Biol. Res. 138:87-98 (1983)), corn alcohol dehydrogenase 1 promoter (Dennis et al., Nucleic Acids Res. 12:3983-4000 (1984)), S-adenosyi-L-methionine synthetase (SAMS) (Vander Mijnsbrugge et al., Plant and Cell Physiology, 37(8):1108-1115 (1996)), corn light harvesting complex promoter (Bansal et al., PNAS 89:3654-3658 (1992)), corn heat shock protein promoter (O'Dell et al., EMBO J. 5:451-458 (1985); and Rochester et al., EMBO J. 5:451-458 (1986)), pea small subunit RuBP carboxylase promoter (Cashmore, "Nuclear genes encoding the small subunit of ribulose-1,5-bisphosphate carboxylase" pp. 29-39 In: Genetic Engineering of Plants, Hollaender ed., Plenum Press 1983; and Poulsen et al., Mol. Gen. Genet. 205:193-200 (1986)), Ti plasmid mannopine synthase promoter (Langridge et al., PNAS 86:3219-3223 (1989)), Ti plasmid nopaline synthase promoter (Langridge et al., (1989), supra), *petunia* chalcone isomerase promoter (van Tunen et al., EMBO 3.7:1257-1263 (1988)), bean glycine rich protein 1 promoter (Keller et al., Genes Dev. 3:1639-1646 (1989)), truncated CaMV 35S promoter (O'Dell et al., Nature 313: 810-812 (1985)), potato patatin promoter (Wenzler et al., Plant Mol. Biol. 13:347-354 (1989)), root cell promoter (Yamamoto et al., Nucleic Acids Res. 18:7449 (1990)), maize zein promoter (Kriz et al., Mol. Gen. Genet. 207:90-98 (1987); Langridge et al., Cell 34:1015-1022 (1983); Reina et al., Nucleic Acids Res. 18:6425 (1990); Reina et al., Nucleic Acids Res. 18:7449 (1990); and Wandelt et al., Nucleic Acids Res. 17:2354 (1989)), globulin-1 promoter (Belanger et al., Genetics 129:863-872 (1991)), a-tubulin cab promoter (Sullivan et al., Mol. Gen. Genet. 215:431-440 (1989)), PEP-Case promoter (Hudspeth et al., Plant Mol. Biol. 12:579-589 (1989)), R gene complex-associated promoters (Chandler et al., Plant Cell 1:1175-1183 (1989)), and chalcone synthase promoters (Franken et al., EMBO J. 10:2605-2612 (1991)). Particularly useful for seed-specific expression is the pea vicilin promoter (Czako et al., Mol. Gen. Genet. 235:33-40 (1992); as well as U.S. Pat. No. 5,625,136). Other useful promoters for expression in mature leaves are those that are switched on at the onset of senescence, such as the SAG promoter from *Arabidopsis* (Gan et al., Science 270:1986-1988 (1995).

In addition, promoters functional in plastids can be used. Non-limiting examples of such promoters include the bacteriophage T3 gene 9 5' UTR and other promoters disclosed in U.S. Pat. No. 7,579,516. Other promoters useful with the present invention include but are not limited to the S-E9 small subunit RuBP carboxylase promoter and the Kunitz trypsin inhibitor gene promoter (Kti3).

In some embodiments, inducible promoters can be used with the present invention. Examples of inducible promoters useable with the present invention include, but are not limited to, tetracycline repressor system promoters, Lac repressor system promoters, copper-inducible system promoters, salicylate-inducible system promoters (e.g., the PR1a system), glucocorticoid-inducible promoters (Aoyama et al., Plant J. 11:605-612 (1997)), and ecdysone-inducible system promoters. Other non-limiting examples of inducible promoters include ABA- and turgor-inducible promoters, the auxin-binding protein gene promoter (Schwab et al., Plant J. 4:423-432 (1993)), the UDF glucose flavonoid glycosyl-transferase promoter (Ralston et al., Genetics 119: 185-197 (1988)), the IVIPI proteinase inhibitor promoter (Cordero et al., Plant J. 6:141-150 (1994)), the glyceraldehyde-3-phosphate dehydrogenase promoter (Kohler et al., Plant Mol. Biol. 29:1293-1298 (1995); Martinez et al., J.

Mol. Biol. 208:551-565 (1989); and Quigley et al., J. Mol. Evol. 29:412-421 (1989)) the benzene sulphonamide-inducible promoters (U.S. Pat. No. 5,364,780) and the glutathione S-transferase promoters. Likewise, one can use any appropriate inducible promoter described in Gatz et al., Current Opinion Biotechnol. 7:168-172 (1996) and Gatz et al., Annu. Rev. Plant Physiol, Plant Mol. Biol. 48:89-108 (1997).

Other suitable promoters include promoters from viruses that infect the host plant including, but not limited to, promoters isolated from Dasheen mosaic virus, Chlorella virus (e.g., the Chlorella virus adenine methyltransferase promoter; Mitra et al., Plant Molecular Biology 26:85 (1994)), tomato spotted wilt virus, tobacco rattle virus, tobacco necrosis virus, tobacco ring spot virus, tomato ring spot virus, cucumber mosaic virus, peanut stump virus, alfalfa mosaic virus, and the like.

The invention also provides an expression cassette comprising a HaHB11 promoter sequence of the invention, optionally in operable association with a nucleotide sequence of interest. The expression cassette can further have a plurality of restriction sites for insertion of a nucleotide sequence of interest to be operably linked to the regulatory regions. In embodiments, the HaHB11 promoter is operably associated with a nucleic acid encoding a HaHB11 polypeptide of the invention. In embodiments, the HaHB11 promoter is operably associated with a heterologous nucleotide sequence of interest. In embodiments, the HaHB11 promoter is operably associated with a heterologous nucleotide sequence of interest. In embodiments, the HaHB11 promoter consists of the polynucleotide ProH11 short sequence of SEQ ID NO:5. In further embodiments, the ProH11 short promoter (SEQ ID NO:5) is operably associated with a polynucleotide sequence encoding HaHB11.1 (SEQ ID NO:3) or HaHB11.1 (SEQ NO:10). In embodiments, the HaHB11 promoter consists of the polynucleotide ProH11 long sequence of SEQ ID NO:16. In additional embodiments, the ProH11 long promoter (SEQ ID NO:16) is Operably associated with a polynucleotide sequence encoding HaHB11.1 (SEQ ID NO:3) or HaHB11.1 (SEQ ID NO:10). In particular embodiments, the expression cassette comprises more than one (e.g., two, three, four or more) heterologous nucleotide sequences.

The expression cassettes of the invention may further comprise a transcriptional termination sequence. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also, Guerineau et al., Mol. Gen. Genet. 262:141 (1991); Proudfoot, Cell 64:671 (1991); Sanfacon et al., Genes Dev. 5:141 (1991); Mogen et al., Plant Cell 2:1261 (1990); Munroe et al., Gene 91:151 (1990); Ballas et al., Nucleic Acids Res. 17:7891 (1989); and Joshi et al., Nucleic Acids Res. 15:9627 (1987). Additional exemplary termination sequences are the pea RubP carboxylase small subunit termination sequence and the Cauliflower Mosaic Virus 35S termination sequence. Other suitable termination sequences will be apparent to those skilled in the art.

Further, in particular embodiments, the nucleotide sequence of interest (e.g., heterologous nucleotide sequence of interest) is operably associated with a translational start site. The translational start site can be derived from the HaHB11 coding sequence or, alternatively, can be the native translational start site associated with a heterologous nucleotide sequence of interest, or any other suitable translational start codon.

In illustrative embodiments, the expression cassette includes in the 5' to 3' direction of transcription, a promoter, a nucleotide sequence of interest (e.g., a heterologous nucleotide sequence of interest), and a transcriptional and translational termination region functional in plants.

Those skilled in the art will understand that the expression cassettes of the invention can further comprise enhancer elements and/or tissue preferred elements in combination with the promoter. In some embodiments, the expression cassette comprises a promoter sequence operably associated with the first intron of the *Arabidopsis* Cox5c2 (SEQ ID NO: 17). In some embodiments, the Cox5c2 is operably associated with the long HaHB11 promoter (proH11 long; SEQ ID NO: 16). In embodiments, the Cox5c2 is operably associated with the short HaHB11 promoter (proH11 short; SEQ ID NO: 5). In further embodiments, the proH11 short promoter and Cox5c2 sequence are operably associated with a polynucleotide sequence encoding HaHB11 having the amino acid sequence of SEQ ID NO:3 or SEQ ID NO:10. In some embodiments, the Cox5c2 is operably associated with the long HaHB11 promoter (proH11 long; SEQ ID NO: 16).). In further embodiments, the proH11 long promoter and Cox5c2 sequence are operably associated with a polynucleotide sequence encoding HaHB11 having the amino acid sequence of SEQ ID NO:3 or SEQ ID NO:10.

Further, in some embodiments, it is advantageous for the expression cassette to comprise a selectable marker gene for the selection of transformed cells.

Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al., EMBO J. 6:2513 (1987); DeBlock et al., Plant Physiol. 91:691 (1989); Fromm et al., BioTechnology 8:833 (1990); Gordon-Kamm et al., Plant Cell 2:603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

Selectable marker genes that can be used according to the present invention further include, but are not limited to, genes encoding: neomycin phosphotransferase II (Fraley et al., CRC Critical Reviews in Plant Science 4:1 (1986)); cyanamide hydratase (Maier-Greiner et al., PNAS 88:4250 (1991)); aspartate kinase; dihydrodipicolinate synthase (Peri et al., BioTechnology 11:715 (1993)); the bar gene (Toki et al., Plant Physiol. 100:1503 (1992); Meagher et al., Crop Sci. 36:1367 (1996)); tryptophane decarboxylase (Goddijn et al., Plant Mol. Biol. 22:907 (1992)); neomycin phosphotransferase (NEO; Southern et al., J. Mol. Appl. Gen. 1:327 (1982)); hygromycin phosphotransferase (HPT or HYG; Shimizu et al., Mol. Cell. Biol. 6:1074 (1986)); dihydrofolate reductase (DHFR; Kwok et al., PNAS 83:4552 (1986)); phosphinothricin acetyltransferase (DeBlock et al., EMBO J. 6:2513 (1987)); 2,2-dichloropropionic acid dehalogenase (Buchanan-Wollatron et al., J. Cell. Biochem. 13D, 330 (1989)); acetohydroxyacid synthase (U.S. Pat. No. 4,761,373 to Anderson et al.; Haughn et al., Mol. Gen. Genet. 221:266 (1988)); 5-enolpyravyl-shikimate-phosphate synthase (aroA; Comai et al., Nature 317:741 (1985)); haloarylnitrilase (WO 87/04181 to Stalker et al.); acetyl-coenzyme A carboxylase (Parker et al., Plant Physiol. 92:1220 (1990)); dihydropteroate synthase (sul1; Guerineau et al., Plant Mol. Biol. 15:127 (1990)); and 32 kDa photosystem II polypeptide (psbA; Hirschberg et al., Science 222:1346 (1983)).

Also included are genes encoding resistance to: chloramphenicol (Herrera-Estrella et al., EMBO J. 2:987 (1983)); methotrexate (Herrera-Estrella et al., Nature 303:209 (1983); Meijer et al., Plant Mol. Biol. 16:807 (1991)); hygromycin (Waldron et al., Plant Mol. Biol. 5:103 (1985); Zhijian et al., Plant Science 108:219 (1995); Meijer et al., Plant Mol. Bio. 16:807 (1991)); streptomycin (Jones et al., Mol. Gen. Genet. 210:86 (1987)); and spectinomycin (Bretagne-Sagnard et al., Transgenic Res. 5:131 (1996)); bleomycin (Hille et al., Plant Mol. Biol. 7:171 (1986)); sulfonamide (Guerineau et al., Plant Mol. Bio. 15:127 (1990); bromoxynil (Stalker et al., Science 242:419 (1988)); 2,4-D (Streber et al., Bio/Technology 7:811 (1989)); phosphinothricin (DeBlock et al., EMBO J. 6:2513 (1987)); spectinomycin (Bretagne-Sagnard et al., Transgenic Research 5:131 (1996)).

Other selectable marker genes include the pat gene (for bialaphos and phosphinothricin resistance), the ALS gene for imidazolinone resistance, the HPH or HYG gene for hygromycin resistance, the Hm1 gene for resistance to the He-toxin, and other selective agents used routinely and known to one of ordinary skill in the art. See generally, Yarranton, Curr. Opin. Biotech. 3:506 (1992); Chistopherson et al., PNAS 89: 6314 (1992); Yao et al., Cell 71:63 (1992); Reznikoff, Mol. Microbial. 6:2419 (1992); Barkley et al., THE OPERON 177-220 (1980); Hu et al., Cell 48:555 (1987); Brown et al., Cell 49:603 (1987); Figge et al., Cell 52:713 (1988); Deuschle et al., PNAS 86:5400 (1989); Fuerst et al., PNAS 86:2549 (1989); Deuschle et al., Science 248:480 (1990); Labow et al., Mol. Cell. Biol. 10:3343 (1990); Zambretti et al., PNAS 89:3952 (1992); Bairn et al., PNAS 88:5072 (1991); Wyborski et al., Nuc. Acids Res. 19:4647 (1991); Hillenand-Wissman, Topics in Mol. and Struct. Biol. 10:143 (1989); Degenkolb et al., Antimicrob. Agents Chemother. 35:1591 (1991); Kleinschnidt et al., Biochemistry 27:1094 (1988); Gatz et al., Plant J. 2:397 (1992); Gossen et al., PNAS 89:5547 (1992); Oliva et al., Antimicrob. Agents Chemother. 36:913 (1992); HLAVKA AL., HANDBOOK OF EXPERIMENTAL PHARMACOLOGY 78 (1985); and Gill et al., Nature 334:721 (1988).

The nucleotide sequence of interest can additionally be operably linked to a sequence that encodes a transit peptide that directs expression of an encoded polypeptide of interest to a particular cellular compartment. Transit peptides that target protein accumulation in higher plant cells to the chloroplast, mitochondrion, vacuole, nucleus, and the endoplasmic reticulum (for secretion outside of the cell) are known in the art. Transit peptides that target proteins to the endoplasmic reticulum are desirable for correct processing of secreted proteins. Targeting protein expression to the chloroplast (for example, using the transit peptide from the RubP carboxylase small subunit gene) has been shown to result in the accumulation of very high concentrations of recombinant protein in this organelle. The pea RubP carboxylase small subunit transit peptide sequence has been used to express and target mammalian genes in plants (U.S. Pat. Nos. 5,717,084 and 5,728,925 to Herrera-Estrella et al.).

Alternatively, mammalian transit peptides can be used to target recombinant protein expression, for example, to the mitochondrion and endoplasmic reticulum. It has been demonstrated that plant cells recognize mammalian transit peptides that target endoplasmic reticulum (U.S. Pat. Nos. 5,202,422 and 5,639,947 to Hiatt et al.).

Further, the expression cassette can comprise a 5' leader sequence that acts to enhance expression (transcription, post-transcriptional processing and/or translation) of an operably associated nucleotide sequence of interest. Leader sequences are known in the art and include sequences from: picornavirus leaders, e.g., EMCV leader (Encephalomyocarditis 5' noncoding region; Elroy-Stein et al., PNASUSA, 86:6126 (1989)); potyvirus leaders, e.g., TEV leader (Tobacco Etch Virus; Allison et al., Virology, 154:9 (1986)); human immunoglobulin heavy-chain binding protein (BiP; Macajak and Sarnow, Nature 353:90 (1991)); untranslated leader from the coat protein mRNA of alfalfa mosaic virus (AMV RNA 4; Jobling and Gehrke, Nature 325: 622 (1987)); tobacco mosaic virus leader (TMV; Gallie, MOLECULAR BIOLOGY OF RNA, 237-56 (1989)); and maize chlorotic mottle viras leader (MCMV; Lommel et al., Virology 81:382 (1991)). See also, Della-Cioppa et al., Plant Physiology 84:965 (1987).

The heterologous nucleotide sequence(s) in the expression cassette can be any nucleotide sequence(s) of interest and can be obtained from prokaryotes or eukaryotes (e.g., bacteria, fungi, yeast, viruses, plants, mammals) or the heterologous nucleotide sequence can be synthesized in whole or in part. Further, the heterologous nucleotide sequence can encode a polypeptide or can be transcribed to produce a functional RNA. In particular embodiments, the functional RNA can be expressed to improve an agronomic trait in the plant (e.g., drought resistance, heat resistance, salt resistance, disease resistance, insect and other pest resistance [e.g., a *Bacillus thuringiensis* endotoxin], herbicide resistance, and the like), to confer male sterility, to improve fertility and/or enhance nutritional quality (e.g., enzymes that enhance nutritional quality). The nucleotide sequence may further be used in the sense orientation to achieve suppression of endogenous plant genes, as is known by those skilled in the art (see, e.g., U.S. Pat. Nos. 5,283,184; and 5,034,323).

The heterologous nucleotide sequence can encode a polypeptide that imparts a desirable agronomic trait to the plant (as described above), confers male sterility, improves fertility and/or improves nutritional quality. Other suitable polypeptides include enzymes that can degrade organic pollutants or remove heavy metals. Such plants, and the enzymes that can be isolated therefrom, are useful in methods of environmental protection and remediation. Alternatively, the heterologous nucleotide sequence can encode a therapeutically or pharmaceutically useful polypeptide or an industrial polypeptide (e.g., an industrial enzyme). Such polypeptides include, but are not limited to antibodies and antibody fragments, cytokines, hormones, growth factors, receptors, enzymes and the like.

Heterologous nucleotide sequences suitable to confer tolerance to the herbicide glyphosate include, but are not limited to the *Agrobacterium* strain CP4 glyphosate resistant EPSPS gene (aroA:CP4) as described in U.S. Pat. No. 5,633,435 or the glyphosate oxidoreductase gene (GOX) as described in U.S. Pat. No. 5,463,175. Other heterologous nucleotide sequences include genes conferring resistance to herbicides that act to inhibit the action of acetolactate synthase (ALS), in particular the sulfonylurea-type herbicides (e.g. mutant forms of the acetolactate synthase (ALS)

gene that lead to such resistance, in particular the S4 and/or Hra mutations), genes coding for resistance to herbicides that act to inhibit the action of glutamine synthase, such as phosphinothricin or basta (e.g., the bar gene). The bar gene encodes resistance to the herbicide basta, the nptII gene encodes resistance to the antibiotics kanamycin and geneticin, and the ALS gene encodes resistance to the herbicide chlorsulfuron.

Suitable heterologous nucleotide sequences that confer insect tolerance include those which provide resistance to pests such as rootworm, cutworm, European Corn Borer, and the like. Exemplary nucleotide sequences include, but are not limited to, a *Bacillus* insect control protein gene (see, e.g., WO 99/31248; U.S. Pat. Nos. 5,689,052; 5,500,365; 5,880,275); *Bacillus thuringiensis* toxic protein genes (see, e.g., U.S. Pat. Nos. 5,366,892; 5,747,450; 5,737,514; 5,723,756; 5,593,881; 6,555,655; 6,541,448; and 6,538,109; Geiser, et al., Gene 48:109 (1986)); and lectins (Van Damme et al., Plant Mol. Biol. 24:825 (1994)).

Alternatively, the heterologous nucleotide sequence can encode a reporter polypeptide (e.g., an enzyme), including but not limited to Green Fluorescent Protein, beta-galactosidase, luciferase, alkaline phosphatase, the GUS gene encoding beta-glucuronidase, and chloramphenicol acetyltransferase.

Where appropriate, the heterologous nucleic acids may be optimized for increased expression in a transformed plant, e.g., by using plant preferred codons. Methods for synthetic optimization of nucleic acid sequences are available in the art. The nucleotide sequence can be optimized for expression in a particular host plant or alternatively can be modified for optimal expression in monocots. See, e.g., EP 0 359 472, EP 0 385 962, WO 91/16432; Perlak et al., PNAS 88, 3324 (1991), and Murray et al., Nucl. Acids Res. 17:477 (1989), and the like. Plant preferred codons can be determined from the codons of highest frequency in the proteins expressed in that plant. Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The invention further provides vectors comprising the nucleic acids and expression cassettes of the invention, including expression vectors, transformation vectors and vectors for replicating and/or manipulating the nucleotide sequences in the laboratory. The vector can be a plant vector, animal (e.g., insect or mammalian) vector, bacterial vector, yeast vector or fungal vector. Generally, according to the present invention, the vector is a plant vector, a bacterial vector, or a shuttle vector that can replicate in either host under appropriate conditions. Bacterial and plant vectors are well-known in the art. Exemplary plant vectors include plasmids (e.g., pUC or the Ti plasmid), cosmids, phage, bacterial artificial chromosomes (BACs), yeast artificial chromosomes (YACs) and plant viruses.

III. TRANSGENIC PLANTS, PLANT PARTS AND PLANT CELLS

The invention also provides transgenic plants, plant parts and plant cells comprising the nucleic acids, expression cassettes and vectors of the invention.

Accordingly, as one aspect the invention provides a cell comprising a nucleic acid, expression cassette, or vector of the invention. The cell can be transiently or stably transformed with the nucleic acid, expression cassette or vector. Further, the cell can be a cultured cell, a cell obtained from a plant, plant part, or plant tissue, or a cell in situ in a plant, plant part or plant tissue. Cells can be from any suitable species, including plant (e.g., *Helianthus annuus*), bacterial, yeast, insect and/or mammalian cells. In representative embodiments, the cell is a plant cell or bacterial cell.

The invention also provides a plant part (including a plant tissue culture) comprising a nucleic acid, expression cassette, or vector of the invention. The plant part can be transiently or stably transformed with the nucleic acid, expression cassette or vector. Further, the plant part can be in culture, can be a plant part obtained from a plant, or a plant part in situ. In representative embodiments, the plant part comprises a cell of the invention, as described in the preceding paragraph.

Seed comprising the nucleic acid, expression cassette, or vector of the invention are also provided. Optionally, the nucleic acid, expression cassette or vector is stably incorporated into the genome of the seed.

The invention also contemplates a transgenic plant comprising a nucleic acid, expression cassette, or vector of the invention. The plant can be transiently or stably transformed with the nucleic acid, expression cassette or vector. In representative embodiments, the plant comprises a cell or plant part of the invention, as described in the preceding paragraphs. In representative embodiments, wherein the nucleic acid, expression cassette or vector encodes a HaHB11 polypeptide of the invention, the transgenic plant has increased tolerance to an abiotic stress, increased yield (e.g., under normal cultivation conditions and/or conditions of mild and/or severe abiotic stress), increased mature height and/or delayed development and/or a prolonged life span. In representative embodiments, wherein the nucleic acid, expression cassette or vector comprises a HaHB11 promoter of the invention, the plant expresses a nucleotide sequence of interest (e.g., a heterologous nucleotide sequence of interest) operably associated with the HaHB11 promoter, where expression is optionally induced by an abiotic stress.

In a representative embodiment, a transgenic plant is stably transformed with an isolated nucleic acid encoding a polypeptide selected from the group consisting of: (a) a polypeptide comprising (i) a HD-Zip domain that binds CAAT(A/T)ATTG (SEQ ID NO:7) and (ii) amino acids 15 to 113 of SEQ ID NO:10; and (b) a polypeptide comprising (i) a HD-Zip domain that binds CAAT(A/T)ATTG (SEQ ID NO:7) and (ii) an amino acid sequence that is at least about 96% identical to amino acids 15 to 181 of SEQ ID NO:10. In some embodiments, the transgenic plant is stably transformed with an isolated nucleic acid encoding the HAHB11 polypeptide of SEQ ID NO:3. In some embodiments, the transgenic plant is stably transformed with an isolated nucleic acid encoding the HAHB11 polypeptide of SEQ ID NO:10.

In further embodiments, the plant is stably transformed with a nucleic acid sequence comprising the nucleotide sequence of SEQ ID NO:9. In some embodiments the transgenic plant is stably transformed with an expression cassette comprising the isolated nucleic acid operably associated with a promoter. In further embodiments, the expression cassette comprises a promoter containing the nucleotide sequence of SEQ ID NO:5 or SEQ ID NO:16. In additional embodiments, the expression cassette comprises a heterologous promoter. In additional embodiments, the expression cassette comprises a selectable marker.

Still further, the invention encompasses a crop comprising a plurality of the transgenic plants of the invention, as described herein. Nonlimiting examples of the types of crops comprising a plurality of transgenic plants of the invention include an agricultural field, a golf course, a residential lawn or garden, a public lawn or garden, a road side planting, an orchard, and/or a recreational field (e.g., a cultivated area comprising a plurality of the transgenic plants of the invention).

Products harvested from the plants of the invention are also provided. Nonlimiting examples of a harvested product include a seed (e.g., sunflower seeds), a leaf, a stem, a shoot, a fruit, flower, root, biomass (e.g., for biofuel production) and/or extract.

In some embodiments, a processed product produced from the harvested product is provided. Nonlimiting examples of a processed product include a protein (e.g., a recombinant protein), an extract, a medicinal product (e.g., artemicin as an antimalarial agent), a fiber or woven textile, a fragrance, dried fruit, a biofuel (e.g., ethanol), a tobacco product (e.g., cured tobacco, cigarettes, chewing tobacco, cigars, and the like), an oil (e.g., sunflower oil, corn oil, canola oil, and the like), a nut butter, a seed butter (e.g., sunflower butter), a flour or meal (e.g., wheat flour, corn meal) and/or any other animal feed (e.g., soy, maize, barley, rice, alfalfa) and/or human food product (e.g., a processed wheat, maize, rice or soy food product). Further, processed product can be cut, dried, cooked, canned, frozen, dehydrated, powdered, ground and/or mixed with other ingredients.

IV. METHODS OF INTRODUCING NUCLEIC ACIDS

The invention also provides methods of delivering a nucleic acid, expression cassette or vector of the invention to a target plant or plant cell (including callus cells or protoplasts), plant parts, seed, plant tissue (including callus), and the like. The invention further comprises host plants, cells, plant parts, seeds, tissue culture (including callus) transiently or stably transformed with the nucleic acids, expression cassettes or vectors of the invention.

The invention further provides a method of expressing a HaHB11 polypeptide in a plant, plant part or plant cell. In representative embodiments, the method comprises transforming the plant, plant part or plant cell with a nucleic acid, expression cassette, or vector of the invention encoding the HaHB11 polypeptide. The plant can be transiently or stably transformed. This method finds use, for example, in methods of evaluating the structure and/or function of HaHB11.

The invention also encompasses a method of increasing tolerance of a plant to abiotic stress, the method comprising: (a) stably transforming a plant cell with a nucleic acid, expression cassette, or vector encoding an HaHB11 polypeptide of the invention; (b) regenerating a stably transformed plant from the stably transformed plant cell of (a); and (c) expressing the nucleotide sequence in the plant (e.g., in an amount effective to increase the tolerance of the plant to an abiotic stress). The method optionally includes the further step of exposing the plant to the abiotic stress (e.g., growing the plant under the abiotic stress conditions).

The invention further provides a method of increasing the yield from a plant, the method comprising: (a) stably transforming a plant cell with a nucleic acid, expression cassette, or vector encoding an HaHB11 polypeptide of the invention; (b) regenerating a stably transformed plant from the stably transformed plant cell of (a); and (c) expressing the nucleotide sequence in the plant (e.g., in an amount effective to increase the yield from the plant). According to this embodiment, the yield of the plant can be increased under normal growth conditions (e.g., normal irrigation and salt conditions) and/or conditions of mild abiotic stress and/or severe abiotic stress. Still further, the invention provides a method of the prolonging (e.g., increasing) the life span and/or delaying development of a plant, the method comprising: (a) stably transforming a plant cell with a nucleic acid, expression cassette, or vector encoding an HaHB11 polypeptide of the invention; (b) regenerating a stably transformed plant from the stably transformed plant cell of (a); and (c) expressing the nucleotide sequence in the plant (e.g., in an amount effective to prolong the life span and/or delay the development of a plant). Without wishing to be bound by any theory of the invention, it appears that the increase in yield seen upon ectopic expression of HaHB11 may result, at least in part, from the delayed development and prolonged life span of the transgenic plant. In representative embodiments, the plant is a turfgrass (including a forage grass or ornamental grass), a biomass grass, or an ornamental plant.

Abiotic stress is as described elsewhere herein. In representative embodiments of the foregoing methods, the abiotic stress comprises drought, salt stress, submergence stress and/or waterlogging stress, and/or stress after removal of a submergence stressor (e.g., desubmergence stress).

In some embodiments, the methods of the invention can be used to invention increase yield and/or increasing tolerance of a plant to abiotic stress. In further embodiments, the abiotic stress comprises drought, salt stress, waterlogging stress, submergence stress, and/or desubmergence stress. Thus, in some embodiments, the transgenic plants of the invention are grown under the abiotic stress conditions. Alternatively, in additional embodiments, the transgenic plants are grown under normal cultivation conditions.

In one embodiment, the invention provides a method of increasing yield and/or increasing tolerance of a plant to abiotic stress, the method comprising: (a) stably transforming a plant cell with an isolated nucleic acid encoding a polypeptide selected from the group consisting of: (i) a polypeptide comprising (i) a HD-Zip domain that binds CAAT(A/T)ATTG (SEQ ID NO:7) and (ii) amino acids 15 to 113 of SEQ ID NO:10; and (ii) a polypeptide comprising (i) a HD-Zip domain that binds CAAT(A/T)ATTG (SEQ ID NO:7) and (ii) an amino acid sequence that is at least about 96% identical to amino acids 15 to 181 of SEQ ID NO:10. In a further embodiment, the invention further includes regenerating a stably transformed plant from the stably transformed plant cell; and expressing the nucleotide sequence in the plant. In some embodiments, the method includes stably transforming a plant cell with an isolated nucleic acid encoding the HAHB11 polypeptide of SEQ ID NO:3 or SEQ ID NO:10.

The invention also provides methods of introducing a nucleic acid into a plant, plant part or plant cell. In representative embodiments, the method comprises transforming the plant, plant part or plant cell with a nucleic acid, expression cassette, or vector comprising an HaHB11 promoter of the invention, optionally, in operable association with a nucleotide sequence of interest (e.g., a heterologous nucleotide sequence of interest). In embodiments, the nucleotide sequence of interest encodes an HaHB11 polypeptide of the invention (e.g., SEQ ID NO:1, nucleotides 7-944 of SEQ ID NO:1, SEQ ID NO:2). In embodiments, the nucleotide sequence of interest encodes an HaHB11 polypeptide having the amino acid sequence of SEQ ID NO:10 (e.g., SEQ ID NO:9). In embodiments, the nucleotide sequence of interest encodes an HaHB11 polypeptide having the amino acid sequence of SEQ ID NO:11, SEQ ID NO:12, SEQ ID NO:13, SEQ ID NO:14 or SEQ ID NO:15. In embodiments of the invention the promoter is operably associated with a nucleotide sequence of interest that is heterologous to the promoter. The plant can be transiently or stably transformed. This method finds use, for example, in methods of evaluating the structure and/or function of the HaHB11 promoter.

As another aspect, the invention provides a method of stably expressing a nucleotide sequence of interest in a plant. According to representative embodiments, the method comprises: (a) stably transforming a plant cell with an expression cassette or vector comprising an HaHB11 promoter of the invention operably associated with a nucleotide sequence of interest (e.g., a heterologous nucleotide sequence of interest); (b) regenerating a stably transformed plant from the stably transformed plant cell of (a); and (c) expressing the nucleotide sequence of interest in the plant. In embodiments, the nucleotide sequence of interest encodes an HaHB11 polypeptide of the invention (e.g., SEQ ID NO:1, nucleotides 7-944 of SEQ ID NO:1, SEQ ID NO:2). In embodiments, the nucleotide sequence of interest encodes an HaHB11 polypeptide having the amino acid sequence of SEQ ID NO:10 (e.g., SEQ ID NO:9). In embodiments, the nucleotide sequence of interest encodes an HaHB11 polypeptide having the amino acid sequence of SEQ ID NO:11, SEQ ID NO:12, SEQ ID NO:13, SEQ ID NO:14 or SEQ ID NO:15. In embodiments of the invention the promoter is operably associated with a nucleotide sequence of interest that is heterologous to the promoter, which may optionally encode a polypeptide (e.g., as described in more detail elsewhere herein). The method can further comprise the step of collecting the polypeptide. Alternatively, in some embodiments, the heterologous nucleotide sequence of interest can be transcribed to produce a functional RNA.

Also contemplated by the present invention is a method of producing a polypeptide in a plant, plant tissue culture or plant cell, wherein the plant, plant tissue culture, or plant cell comprises an expression cassette or vector comprising an HaHB11 promoter of the invention operably associated with a nucleotide sequence of interest (e.g., a heterologous nucleotide sequence of interest, wherein the nucleotide sequence of interest encodes a polypeptide. In embodiments, the nucleotide sequence of interest encodes an HaHB11 polypeptide of the invention (e.g., SEQ ID NO:1, nucleotides 7-944 of SEQ ID NO:1, SEQ ID NO:2). In embodiments, the nucleotide sequence of interest encodes an HaHB11 polypeptide having the amino acid sequence of SEQ ID NO:10 (e.g., SEQ ID NO:9). In embodiments, the nucleotide sequence of interest encodes an HaHB11 polypeptide having the amino acid sequence of SEQ ID NO:11, SEQ ID NO:12, SEQ ID NO:13, SEQ ID NO:14 or SEQ ID NO:15. In embodiments of the invention the promoter is operably associated with a nucleotide sequence of interest that is heterologous to the promoter. In representative embodiments, the method comprises growing the plant or culturing the tissue culture or plant cell under conditions sufficient for the production of the polypeptide in the plant, plant tissue culture or plant cell and, optionally, collecting the polypeptide. According to this embodiment, the polypeptide can be a secreted polypeptide.

The invention also encompasses transgenic plants, plant parts, and plant cells produced by the methods of the invention.

Also provided by the invention are seed produced from the inventive transgenic plants. Optionally, the seed comprise a nucleic acid, expression cassette or vector of the invention stably incorporated into the genome.

Methods of introducing nucleic acids, transiently or stably, into plants, plant tissues, cells, protoplasts, seed, callus and the like are known in the art. Stably transformed nucleic acids can be incorporated into the genome. Exemplary transformation methods include biological methods using viruses and *Agrobacterium*, physicochemical methods such as electroporation, floral dip methods, polyethylene glycol, ballistic bombardment, microinjection, and the like. Other transformation technology includes the whiskers technology that is based on mineral fibers (see •e.g., U.S. Pat. Nos. 5,302,523 and 5,464,765) and pollen tube transformation. In one form of direct transformation, the vector is microinjected directly into plant cells by use of micropipettes to mechanically transfer the recombinant DNA (Crossway, Mol. Gen. Genetics 202:179 (1985)).

In another protocol, the genetic material is transferred into the plant cell using polyethylene glycol (Krens et al., Nature 296:72 (1982)).

In still another method, protoplasts are fused with minicells, cells, lysosomes, or other fusible lipid-surfaced bodies that contain the nucleotide sequence to be transferred to the plant (Fraley et al., PNAS 79:1859 (1982)).

Nucleic acids may also be introduced into the plant cells by electroporation (Fromm et al., PNAS 82:5824 (1985)). In this technique, plant protoplasts are electroporated in the presence of nucleic acids comprising the expression cassette. Electrical impulses of high field strength reversibly permeabilize biomembranes allowing the introduction of the nucleic acid. Electroporated plant protoplasts reform the cell wall, divide and regenerate. One advantage of electroporation is that large pieces of DNA, including artificial chromosomes, can be transformed by this method.

Ballistic transformation typically comprises the steps of: (a) providing a plant material as a target; (b) propelling a microprojectile carrying the heterologous nucleotide sequence at the plant target at a velocity sufficient to pierce the walls of the cells within the target and to deposit the nucleotide sequence within a cell of the target to thereby provide a transformed target. The method can further include the step of culturing the transformed target with a selection agent and, optionally, regeneration of a transformed plant. As noted below, the technique may be carried out with the nucleotide sequence as a precipitate (wet or freeze-dried) alone, in place of the aqueous solution containing the nucleotide sequence.

Any ballistic cell transformation apparatus can be used in practicing the present invention. Exemplary apparatus are disclosed by Sandford et al., Particulate Science and Technology 5:27 (1988)), Klein et al., Nature 327:70 (1987)), and in EP 0 270 356. Such apparatus have been used to transform maize cells (Klein et al., PNAS 85:4305 (1988)), soybean callus (Christou et al., Plant Physiol. 87:671 (1988)), McCabe et al., BioTechnology 6:923 (1988), yeast mitochondria (Johnston et al., Science 240:1538 (1988)), and *Chlamydomonas* chloroplasts (Boynton et al., Science 240: 1534 (1988)).

Alternately, an apparatus configured as described by Klein et al., (Nature 70:327 (1987)) may be utilized. This apparatus comprises a bombardment chamber, which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a borehole formed therein, which is smaller in diameter than the microprojectile. The macroprojectile carries the microprojectile(s), and the macroprojectile is aimed and fired at the borehole. When the macroprojectile is stopped by the stopping plate, the microprojectile(s) is propelled through the borehole. The target is positioned in the bombardment chamber so that a microprojectile(s) propelled through the bore hole penetrates the cell walls of the cells in the target and deposit the nucleotide sequence of interest carried thereon in the cells of the target. The bombardment chamber is partially evacuated prior to use to prevent atmospheric drag from unduly slowing the microprojectiles. The chamber is only partially evacuated so that the target tissue is not desiccated during bombardment. A vacuum of between about 400 to about 800 millimeters of mercury is suitable.

In alternate embodiments, ballistic transformation is achieved without use of microprojectiles. For example, an aqueous solution containing the nucleotide sequence of interest as a precipitate may be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the nucleic acid precipitate itself ("wet" precipitate) or a freeze-dried nucleotide precipitate directly on the plate-contact end of the macroprojectile without a microprojectile. In the absence of a microprojectile, it is believed that the nucleotide sequence must either be propelled at the tissue target at a greater velocity than that needed if carried by a microprojectile, or the nucleotide sequenced caused to travel a shorter distance to the target (or both).

It particular embodiments, the nucleotide sequence fs delivered by a microprojectile. The microprojectile can be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their carrying capacity.

The nucleotide sequence may be immobilized on the particle by precipitation. The precise precipitation parameters employed will vary depending upon factors such as the particle acceleration procedure employed, as is known in the art. The carrier particles may optionally be coated with an encapsulating agents such as polylysine to improve the stability of nucleotide sequences immobilized thereon, as discussed in EP 0 270 356 (column 8).

Alternatively, plants may be transformed using *Agrobacterium tumefaciens* or *Agrobacterium rhizogenes*. *Agrobacterium*-mediated nucleic acid transfer exploits the natural ability of *A. tumefaciens* and *A. rhizogenes* to transfer DNA into plant chromosomes. *Agrobacterium* is a plant pathogen that transfers a set of genes encoded in a region called T-DNA of the Ti and Ri plasmids of *A. tumefaciens* and *A. rhizogenes*, respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be removed by deletion of the genes in the T-DNA without loss of DNA transfer and integration. The DNA to be transferred is attached to border sequences that define the end points of an integrated T-DNA.

Transfer by means of engineered *Agrobacterium* strains has become routine for many dicotyledonous plants. Some difficulty has been experienced, however, in using *Agrobacterium* to transform monocotyledonous plants, in particular, cereal plants. However, *Agrobacterium* mediated transformation has been achieved in several monocot species, including cereal species such as rye, maize (Rhodes et al., Science 240, 204 (1988)), and rice (Hiei et al., (1994) Plant J. 6:271).

While the following discussion will focus on using *A. tumefaciens* to achieve gene transfer in plants, those skilled in the art will appreciate that this discussion also applies to *A. rhizogenes*. Transformation using *A. rhizogenes* has developed analogously to that of *A. tumefaciens* and has been successfully utilized to transform, for example, alfalfa, *Solanum nigrum* L., and poplar (U.S. Pat. No. 5,777,200 to Ryals et al.). As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. rhizogenes* is strain 15834.

In particular protocols, the *Agrobacterium* strain is modified to contain the nucleotide sequences to be transferred to the plant. The nucleotide sequence to be transferred is incorporated into the T-region and is typically flanked by at least one T-DNA border sequence, optionally two T-DNA border sequences. A variety of *Agrobacterium* strains are known in the art particularly, and can be used in the methods of the invention. See, e.g., Hooykaas, Plant Mol. Biol. 13:327 (1989); Smith et al., Crop Science 35:301 (1995); Chilton, PNAS 90, 3119 (1993); Mollony et al., Monograph Theor. Appl. Genet NY 19, 148 (1993); Ishida et al., Nature Biotechnol. 14:745 (1996); and Komari et al., The Plant J. 10:165 (1996).

In addition to the T-region, the Ti (or Ri) plasmid contains a vir region. The vir region is important for efficient transformation, and appears to be species-specific.

Two exemplary classes of recombinant Ti and Ri plasmid vector systems are commonly used in the art. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., EMBO J. 3:1681 (1984), and the non-oncogenic Ti plasmid pGV2850 described by Zambryski et al., EMBOJ 2:2143 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, Nucleic Acids Research 12:8711 (1984), and the non-oncogenic Ti plasmid PAL4404 described by Hoekma, et al., Nature 303:179 (1983).

Binary vector systems have been developed where the manipulated disarmed T-DNA carrying the heterologous nucleotide sequence of interest and the vir functions are present on separate plasmids. In this manner, a modified T-DNA region comprising foreign DNA (the nucleic acid to be transferred) is constructed in a small plasmid that replicates in E. coli. This plasmid is transferred conjugatively in a tri-parental mating or via electroporation into A. tumefaciens that contains a compatible plasmid with virulence gene sequences. The vir functions are supplied in trans to transfer the T-DNA into the plant genome. Such binary vectors are useful in the practice of the present invention.

In particular embodiments of the invention, super-binary vectors are employed. See, e.g., U.S. Pat. No. 5,591,615 and EP 0 604 662. Such a super-binary vector has been constructed containing a DNA region originating from the hypervirulence region of the Ti plasmid pTiBo542 (Jin et al., J. Bacterial. 169:4417 (1987)) contained in a super-virulent A. tumefaciens A281 exhibiting extremely high transformation efficiency (Hood et al. Biotechnol. 2:702 (1984); Hood et al., J. Bacterial. 168:1283 (1986); Komari et al., J. Bacterial. 166:88 (1986); Jin et al., J. Bacterial. 169:4417 (1987); Komari, Plant Science 60:223 (1987); ATCC Accession No. 37394.

Exemplary super-binary vectors known to those skilled in the art include pTOK162 (Japanese patent Appl. (Kokai) No. 4-222527, EP 504,869, EP 604,662, and U.S. Pat. No. 5,591,616) and pTOK233 (Komari, Plant Cell Reports 9:303 (1990); Ishida et al., Nature Biotechnology 14:745 (1996)). Other super-binary vectors may be constructed by the methods set forth in the above references. Super-binary vector pTOK162 is capable of replication in both E. coli and in A. tumefaciens. Additionally, the vector contains the virB, virC and virG genes from the virulence region of pTiBo542. The plasmid also contains an antibiotic resistance gene, a selectable marker gene, and the nucleic acid of interest to be transformed into the plant. The nucleic acid to be inserted into the plant genome is typically located between the two border sequences of the T region. Super-binary vectors of the invention can be constructed having the features described above for pTOK162.

The T-region of the super-binary vectors and other vectors for use in the invention are constructed to have restriction sites for the insertion of the genes to be delivered. Alternatively, the DNA to be transformed can be inserted in the T-DNA region of the vector by utilizing in vivo homologous recombination. See, Herrera-Esterella et al., EMBO J. 2:987 (1983); Horch et al., Science 223:496 (1984). Such homologous recombination relies on the fact that the super-binary vector has a region homologous with a region of bpR322 or other similar plasmids. Thus, when the two plasmids are brought together, a desired gene is inserted into the super-binary vector by genetic recombination via the homologous regions.

In plants stably transformed by Agrobacteria-mediated transformation, the nucleotide sequence of interest is incorporated into the plant nuclear genome, typically flanked by at least one T-DNA border sequence and generally two T-DNA border sequences.

Plant cells may be transformed with Agrobacteria by any means known in the art, e.g., by co-cultivation with cultured isolated protoplasts, or transformation of intact cells or tissues. The first uses an established culture system that allows for culturing protoplasts and subsequent plant regeneration from cultured protoplasts. Identification of transformed cells or plants is generally accomplished by including a selectable marker in the transforming vector, or by obtaining evidence of successful bacterial infection.

Protoplasts, which have been transformed by any method known in the art, can also be regenerated to produce intact plants using known techniques.

Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. II, 1986). Essentially all plant species can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

Alternatively, transgenic plants may be produced using the floral dip method (See, e.g., Clough et al., Plant J. 16:735-743 (1998), which avoids the need for plant tissue culture or regeneration. In one representative protocol, plants are grown in soil until the primary inflorescence is about 10 cm tall. The primary inflorescence is cut to induce the emergence of multiple secondary inflorescences. The inflorescences of these plants are typically dipped in a suspension of Agrobacterium containing the vector of interest, a simple sugar (e.g., sucrose) and surfactant. After the dipping process, the plants are grown to maturity and the seeds are harvested. Transgenic seeds from these treated plants can be selected by germination under selective pressure (e.g., using the chemical bialaphos). Transgenic plants containing the selectable marker survive treatment and can be transplanted to individual pots for subsequent analysis. See, Bechtold, N et al., Methods Mol Biol. 82:259-266 (1998); Chung et al., Transgenic Res 9:471-476 (2000); Clough et al., A. Plant J. 16:735-743 (1998); Mysore et al., Plant J. 21: 9-16 (2000); Tague et al., Transgenic Res. 10:259-267 (2001); Wang et al., Plant Cell Rep 22:274-281 (2003); Ye et al., Plant J., 19:249-257 (1999).

The particular conditions for transformation, selection and regeneration can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine what is an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Having described the present invention, the same will be explained in greater detail in the following examples, which are included herein for illustration purposes only, and which are not intended to be limiting to the invention.

Example 1

Experimental Procedures

Constructs

35SCaMV:HaHB11:

A HaHB11 EST was obtained from Tucson University, Arizona (at genome.arizona.edu; NCBI Accession No. DY923855; SEQ ID NO:1) and amplified with specific oligonucleotides in order to clone it in the pBI121 vector, under the control of the 358 CaMV promoter.

PrH11:GUS:

The promoter region of HaHB11 was isolated from a BAC genomic library using a specific probe. The approximately 125 Kbp BAC insert was restricted with several enzymes, electrophoresed and hybridized in a Southern blot with the same probe. A positive 2000 bp fragment was subcloned in the pUC119 vector and sequenced. The insert presented 525 bp corresponding to the HaHB11 coding sequence plus a 422 bp segment upstream of the +1 position corresponding to a partial fragment of the promoter. This fragment was amplified by PCR with specific oligonucleotides and cloned into the pBI101.3 vector. In this way, the HaHB11 promoter directs the expression of the GUS reporter gene. This construct containing the short 422 bp promoter portion was named PrH11:GUS.

```
HaHB11 cDNA sequence
                                         (SEQ ID NO: 1)
gatgatatatctagtagctagggaggttgaataatagcacacgcca ctagaggccattggctcttagaattatttattttatatatctc gatcaactccc aattggtagttgagaaaatggcagaaaacagtagtagtagtataga gagaaagaagagcaagaagcataacaataggaggttcagcgatgaa caa attaaaatcactggagtcggtgttcaagagggagaacaagctggaa cccaaggaagaaggtggagatggctagagagctgggactgcacccg cgc aggtggctatatggtttcaaaacagaagggctcgctggaagtccaa acaagtggagcaagactactacaatctcaaggccgattacgacacc ttagct caccgcttcgagtccttaaagaaggagaaacatgccttgctccacc aggtaagtcagctaaaagaactggacagtgggtctgaaaacggagg agag ttgaagaatggtaactcaagcagcggaccattagaatacatgcagg gtgataaattagtctcagaagaagaagaagaagaaaggcatgaaaa ccttg acatggctagtcttttgatcagtcatgttcaaactggtgggacat
```

```
ttggtcatcaaactcatgatcgatattatatatagcgtagagaa ttatatatgtata tcttatggggtttgaattgaagtagctagctagctaggatactagt tagatatataggaggagctaattaaggatgtaacggcaaagtggtg agcatgtg gatgggcttgctgtttgtttgcactatgcaagatatgtgtgcaaac tactactactactagtgtgtcttcacgttcaactcaaatctcatgt gattgcaaactc gatccatcttattttttcgttttcttaatgctat ctaactttttgatccaccct
``` cDNA sequence corresponding to the HaHB11 EST. The start codon (atg) is double-underlined and in bold. Underlined are the sequences of the oligonucleotides used to amplify the coding region in order to clone it in the BamHI/SacI sites of the pBI 121 vector.

```
HaHB11 coding sequence
                                         (SEQ ID NO: 2)
atggcagaaaacagtagtagtagtatagagagaaagaagagcaaga agcataacaataggaggncagcgatgaacaaataaaatcactggag tc ggtgacaagagggagaacaagctggaaccaaggaagaaggtggaga tggctagagagctgggactgcacccgcgccaggtggctatatggtt tc aaaacagaagggctcgctggaagtccaaacaagtggagcaagacta ctacaatctcaaggccgattacgacaccttagctcaccgcttcgag tcctt aaagaaggagaaacatgccttgctccaccaggtaagtcagctaaaa gaactggacagtgggtctgaaaacggaggagagttgaagaatggta actc aagcagcggaccattagaatacatgcagggtgataaattagtctca gaagaagaagaagaagaaaggcatgaaaaccttgacatggctagtc tttttg atcagtcatgttcaaactggtgggacatttggtcatcaa actcatga
```

The start codon (atg) is double-underlined and in bold.

```
HaHB11 protein sequence
                                         (SEQ ID NO: 3)
MAENSSSSIERKKSKKHNNRRFSDEQIKSLESVFKRENKLEPRKKVEMAR

ELGLHPRQVAIWF

QNRRARWKSKQVEQDYYNLKADYDTLAHRFESLKKEKHALLHQVSQLKEL

DSGSENGGELK

NGNSSSGPLEYMQGDKLVSEEEEEERHENLDMASLFDQSCSNWWDIWSSN
```

-continued

Genomic fragment containing partial HaHB11
promoter sequence
(SEQ ID NO: 4)
aaaatagaaatattcccatcgatcataaacaattaatatgagtatacata atgaaaactaaccttcaacaccgttgttaatt<u>catttatacgccattcc</u> aagtatgcctaggcggtagagattgttgtctttgaaggagaagatcgatt aggattcaaatcctagcatggggtagattagcatgaatatggtataacta tgggtaggattaatgtaacattcgccgttgcaaaaaaaaaaaaaaatca tttttatcgtcggtgcacgttttaaggttattaattaataacttgtaact aattgtaagcatcaacacatgttatgtcgtaccagattttttgtattatta attattagtctgctcatgtatatttaataattaataataatcggttaggc atattgtcttccaagtgatatgaataaaatagttgtggaaataagaaaag gaaatatgattaatgataatatctagtagctagggaggttgaataatagc acacgccactagaggccattggctcttagaattatttattatttatata tctcgatcaactcccaattggtagttgagaaaATGGCAGAAACAGTAGT

AGTAGTATAGAGAGAAAGAAGAGCAAGAAGCATAACAATAGCAGCAGTAG

GAGGTTCAGCGATGAACAAATAAAAATCACTAGAGTCGGTGTTCAAGAGG

GAGAACAAGCTGGAACCAAGGAAGAAGGTGGAGATGGCTAGAGAGCTGGG

ACTGCACCCGCGCCAGGTGGCTATATGGTTTCAAAACAGAAGGGCTCGCT

GAAGTCCAAACAGGGGAGCAGACTCTCATTCATGCTTT

The promoter sequence is in lower case letters. In bold, the 5' non coding region. Underlined, the oligonucleotide used to clone the promoter in the pBI101.3 vector. In capital letters, the cDNA.

Partial HaHB11 promoter sequence
(SEQ ID NO: 5)
aaaatagaaatattcccatcgatcataaacaattaatatgagtatacat aatgaaaactaaccttcaacaccgttgttaattcatttatacgccatt ccaagtatgcctaggcggtagagattgttgtcatgaaggagaagatcga ttaggattcaaatcctagcatggggtagattagcatgaatatggtataa ctatgggtaggattaatgtaacattcgccgttgcaaaaaaaaaaaaaa atcattttatcgtcggtgcacgttttaaggttattaattaataacttt gtaactaattgtaagcatcaacacatgttatgtcgtaccagattttttgt attattaattattagtctgctcatgtatatttaataattaataataatc ggttaggcatattgtcttccaagt Partial HaHB11 promoter sequence and 5' UTR
(SEQ ID NO: 6)
aaaatagaaatattcccatcgatcataaacaattaatatgagtatacat aatgaaaactaaccttcaacaccgttgttaattcatttatacgccatt ccaagtatgcctaggcggtagagattgttgtattgaaggagaagatcga ttaggattcaaatcctagcatggggtagattagcatgaatatggtataa ctatgggtaggattaatgtaacattcgccgttgcaaaaaaaaaaaaaa atcattttatcgtcggtgcacgttttaaggttattaattaataacttg taactaattgtaagcatcaacacatgttatgtcgtaccagattttttgta ttattaattattagtctgctcatgtatatttaataattaataataatcg gttaggcatattgtcttccaagtgatatgaataaaattagttgtggaaa taagaaaaggaaatatgattaatgataatatctagtagctagggaggt tgaataatagcacacgccactagaggccattggctcttagaattattta tttatttatatatacgatcaactcccaattggtagttgagaaa Plant Material and Growth Conditions

*Arabidopsis thaliana* Heyhn. ecotype Columbia (Col-0) was purchased from Lehle Seeds (Tucson, Ariz.). Plants were grown directly on soil in a growth chamber at 22-24° C. under long-day photoperiods (16 h of illumination with a mixture of cool—white and Grolux fluorescent lamps) at an intensity of approximately 150 uEm$^{-2}$ s$^{-1}$ in 8 cm diameter×7 cm height pots during the periods indicated in the figures. *Helianthus annuus* L (sunflower CF33, from Advanta seeds or HA89 public genotype) seeds were grown on Petri dishes or in soil pots in a culture chamber at 28° C. for variable periods of time depending on the purpose of the experiment as detailed in the figure legends.

Drought Assays

Depending on the experiment and as stated in the figure legends, sunflower seedlings placed on a filter paper or R2 plants grown on soil pots were stressed by cessation of watering during a ten day period. Every two days after this treatment, 1 cm diameter leaf disks were frozen in liquid nitrogen for further RNA analysis. Twenty five-day-old *Arabidopsis* plants were subjected to drought stress by cessation of watering for 16-18 days. After this treatment, the plants were re-watered until saturation. Survivors were counted two days after recovery at normal growth conditions. For water loss evaluation, five leaves from four different plants from each genotype were removed at the times indicated in the figure and weighed (W1). After that, the same leaves were incubated in deionized water for 3 h and weighed again (W2). Water loss was estimated as the difference between W1 and W2.

In the case of drought assays maintaining the same water volume, soil pots were weighed every two-three days and water was added as required to maintain the same amount of water in each soil pot. The weight differences were registered in order to calculate the total water volume added to each pot.

Salinity Stress Assays

Salinity stress was applied on sunflower R2 plants grown on soil pots by irrigating them with NaCl 50 mM, NaCl 150 mM (one week later) and finally, NaCl 200 mM (one more week). After each salt solution addition, 1 cm diameter leaf disks were collected and frozen in liquid nitrogen for further RNA analysis.

*Arabidopsis* 21-day-old plants grown in normal conditions were salt stressed by adding 1.5 liter of 50 mM NaCl to the whole tray. One week after the plants were watered with an additional liter of 150 mM NaCl and one additional week after, another liter of 200 mM NaCl was added. In this way, plants in the reproductive stage were salt stressed.

Hormone Treatments

Sunflower seedlings (7-day-old) growing on wet paper were placed in liquid media containing the different hormones (in the concentrations indicated in the figure legends) and incubated for two hours. The plants were then frozen in liquid nitrogen; total RNA was extracted from each sample and analyzed by real time RT-PCR as described below.

A similar procedure was followed with 21-day-old plants grown on perlite/vermiculite.

*Arabidopsis thaliana* Transformation

Transformed *Agrobacterium tumefaciens* strain LBA4404 was used to obtain transgenic *Arabidopsis* plants by the floral dip procedure (Clough and Bent, Plant J. 16:735-743 (1998)). Transformed plants were selected on the basis of kanamycin resistance and positive PCR which was carried out on genomic DNA with specific oligonucleotides. To assess HaHB11 expression, real-time RT-PCR were performed on T2 transformants, as described below. Five positive independent lines for each construct (arising from at least two different transformation experiments) were used to select homozygous T3 and T4 in order to analyze phenotypes and the expression levels of HaHB11. Plants transformed with pBI101.3 were used as negative controls (referred to as WT in the figures). For the other constructs, selection was similarly carried out and three-five independent lines chosen for the analysis.

Transient Transformation of Sunflower Leaves

Transient transformation of sunflower leaf discs was carried out as described Manavella and Chan (2009). Sunflower leaves were infiltrated with 5 ml of *Agrobacterium tumefaciens* strain LBA4404 and then transformed with 35S:HaHB11 or 35S:GUS, used as control. After infiltration, plants were placed in the growth chamber for an additional 48 hours; 1 cm diameter disks (50 mg each) were excised from the infiltrated leaves and RNA was then extracted with Trizol (see below). For each gene transcript measurement, two disks coming from different plants were analyzed and the experiment was repeated at least twice. In order to test the efficiency of infiltration in these experiments, GUS reporter gene expression was measured by histochemical GUS staining.

Histochemical GUS Staining

In situ assays of GUS activity were performed as described by Jefferson et al., EMBO J. 6:3901-3907 (1987). Whole plants were immersed in a 1 mM 5-bromo-4-chloro-3-indolyl-b-glucuronic acid solution in 100 mM sodium phosphate pH 7.0 and 0.1% Triton X-100 and, after applying vacuum for 5 min, they were incubated at 37° C. overnight. Chlorophyll was cleared from green plant tissues by immersing them in 70% ethanol.

RNA Isolation and Expression Analyses by Real Time RT-PCR

RNA for real-time RT-PCR was prepared with TRIZOL® reagent (Invitrogen™) according to the manufacturer's instructions. RNA (2 ug) was used for the RT reactions using M-MLV reverse transcriptase (Promega), Quantitative PCRs were carried out using a MJ-Chromo4 apparatus in a 20 ul final volume containing 1 ul SyBr green (10×), 8 pmol of each primer, 2 mM $MgCl_2$, 10 ul of a 1/25 dilution of the RT reaction and 0.12 ul Platinum Taq (Invitrogen Inc.). Fluorescence was measured at 78-80° C. during 40 cycles. Sunflower RNA was also prepared with the TRIZOL® (Invitrogen Inc.) technique, but in this case the dilution of the RT reaction was 1/50.

Specific oligonucleotides to amply each gene were designed (data not shown).

Chlorophyll Measurements

Extracts from 100 mg of leaves were prepared after freezing with liquid nitrogen. To each sample, 1.5 ml of 80% acetone were added, and the tubes placed in the darkness during 30 min. During this incubation the sample solids were decanted, and the absorbance at 645 and 663 was measured in the supernatants with a spectrophotometer. Chlorophyll concentration was quantified according to Whatley et al., Nature 10:705-708 (1963).

Stomatal Closure

Stomatal closure was quantified on drought stressed plants grown on MS plates, MS supplemented with 10 uM ABA or soil pots. Controls were performed with plants grown at normal conditions.

An adhesive was glued on the abaxial side of leaves; the adhesive was then carefully detached and glued over a microscope slide in order to take photographs and quantify the open and closed stomata.

Water Loss Treatment

During the drought or desubmergence assay, one leaf from five to six different plants was removed at the time points indicated in the figure legend. Subsequently, leaves were weighed (W1), incubated in demineralized water for 3 h, and weighed again (W2). Water loss rate was calculated as (W2−W1)/W2.

Flooding Stress

To perform submergence assays, 25-day-old plants were completely submerged with 3 cm of water over the aerial part of the plant during 6-8 days. In waterlogging assays, only the roots were submerged by filling the pots with water to a height of 7 cm, the pots being 8 cm height.

Photographs were taken and survival rates were calculated after 6 days of recovery.

Example 2

HaHB11 Expression Pattern

Figure 3:
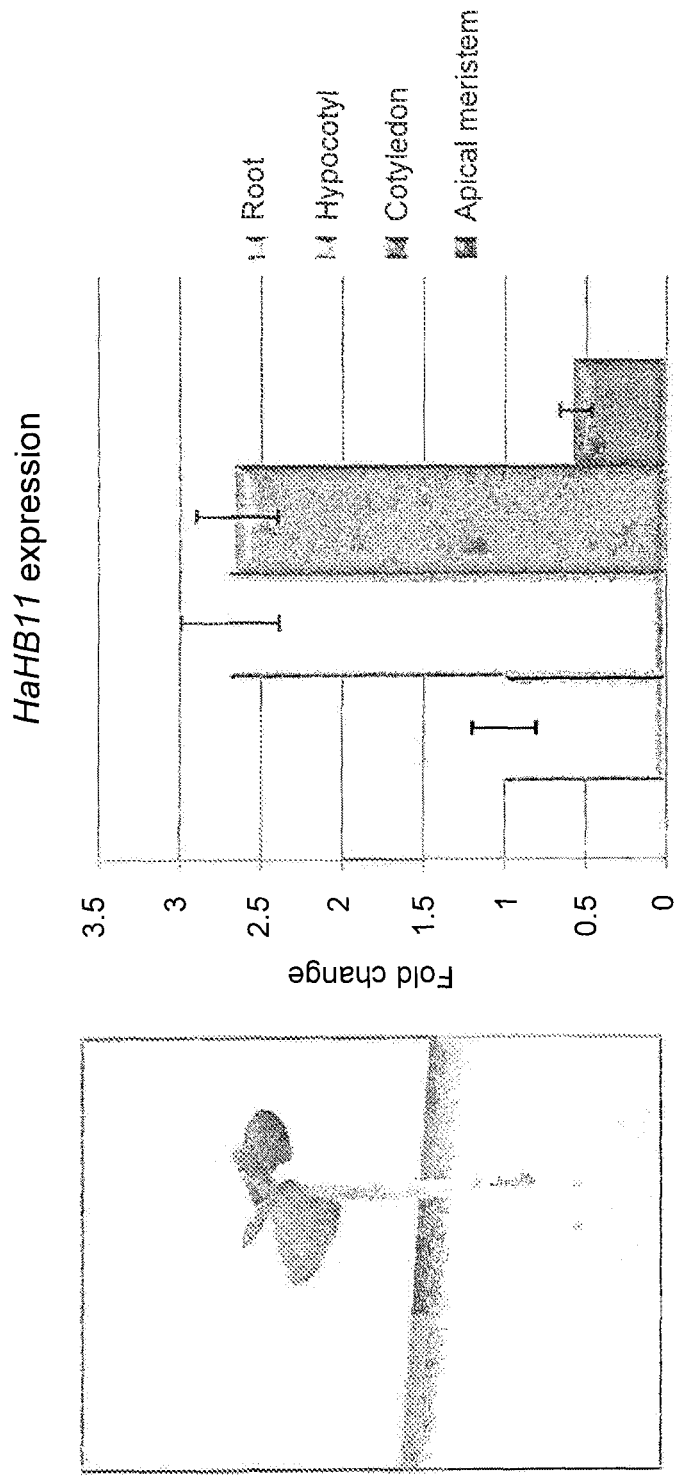
FIG. 3: HaHB11 expression pattern in 7-day-old sunflower seedlings. HaHB11 transcript levels were quantified by qPCR and normalized with housekeeping ACTIN transcripts. The values obtained were normalized with respect to the value measured in the root sample, arbitrarily assigned a value of one. Error bars correspond to SD among three biological replicas.
Figure 4:
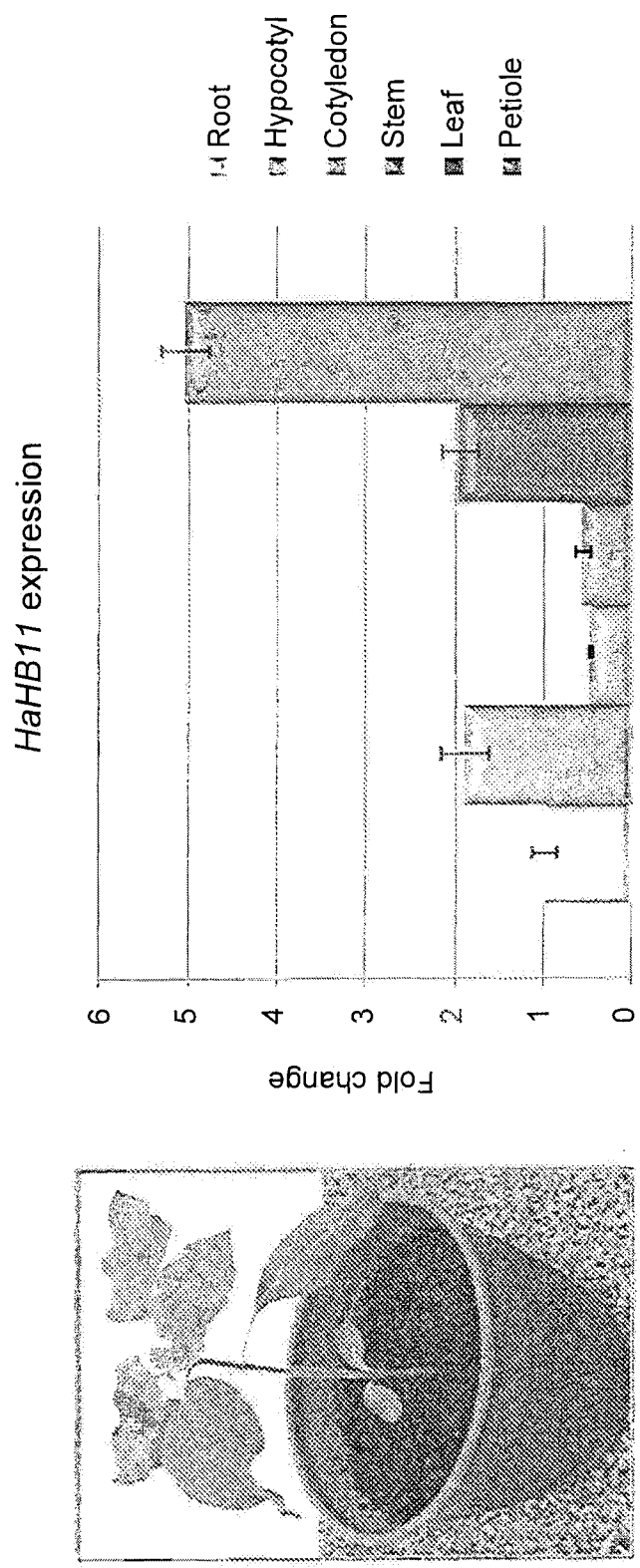
FIG. 4: HaHB11 expression pattern in 21-day-old sunflower plants. HaHB11 transcript levels were quantified by qPCR and normalized with housekeeping ACTIN transcripts. The values obtained were normalized with respect to the value measured in root sample, arbitrarily assigned a value of one. Error bars correspond to SD among three biological replicas.
Figure 5:
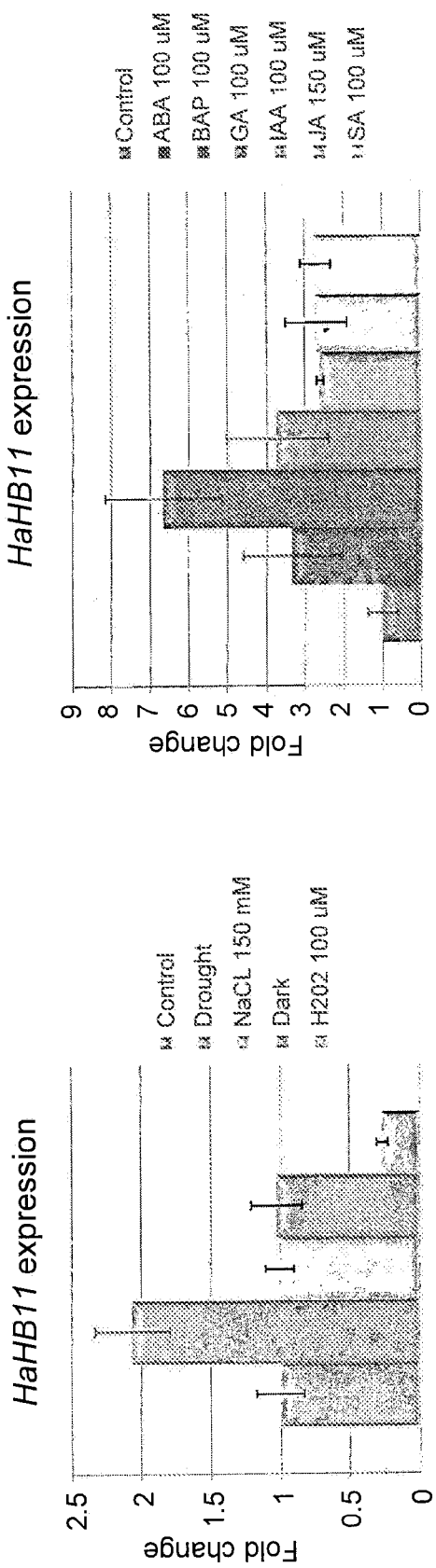
FIG. 5: HaHB11 expression pattern in 7-day-old sunflower seedlings under different treatments. HaHB11 transcript levels were quantified by qPCR and normalized with housekeeping ACTIN transcripts. The values obtained were normalized with respect to the value measured in root sample, arbitrarily assigned a value of one. Error bars correspond to SD among three biological replicas.

The sunflower gene HaHB11 encodes a 175 amino acid protein belonging to the HD-Zip I subfamily of transcription factors (see schematic in FIG. 1A, B; SEQ ID NO:3). In order to characterize HaHB11 gene expression, total RNA was isolated from 7- and 21-day-old sunflower plants and analyzed by qRT-PCR as described in Example 1. FIG. 3 shows that in 7-day-old seedlings, HaHB11 is mainly expressed in hypocotyls and cotyledons as compared with roots and meristems, while 21-day-old plants (FIG. 4) showed high expression in petioles as compared with other tissues/organs.

Figure 6:
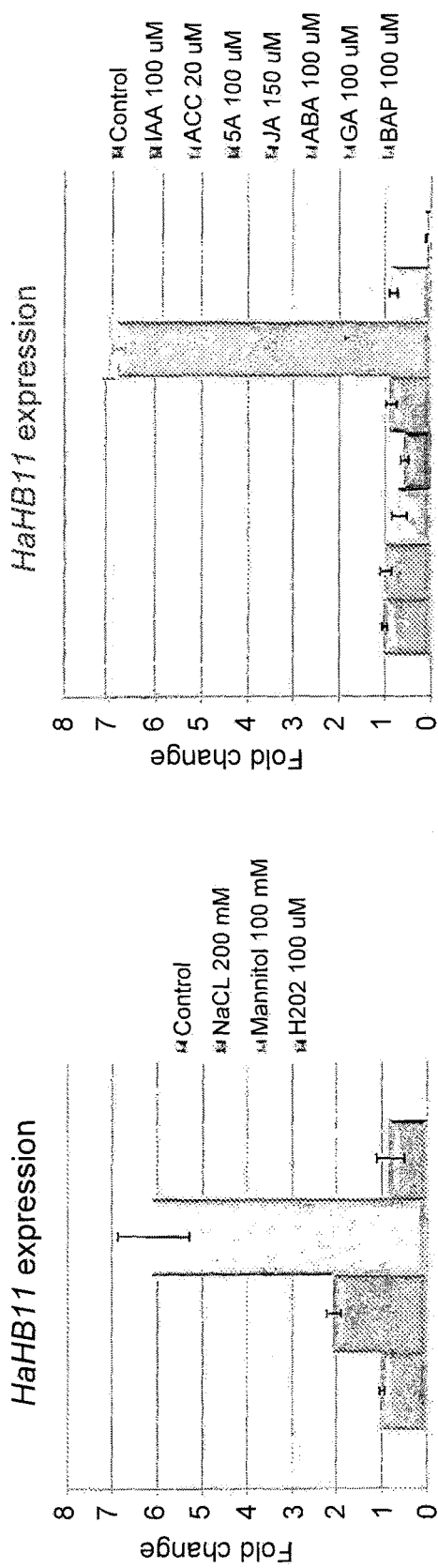
FIG. 6: HaHB11 expression pattern in leaf discs of 21-day-old sunflower plants under different treatments. HaHB11 transcript levels were quantified by qPCR and normalized with housekeeping ACTIN transcripts. The obtained values were normalized with respect to the value measured in root sample, arbitrarily assigned a value of one. Error bars correspond to SD among three biological replicas.
Figure 7:
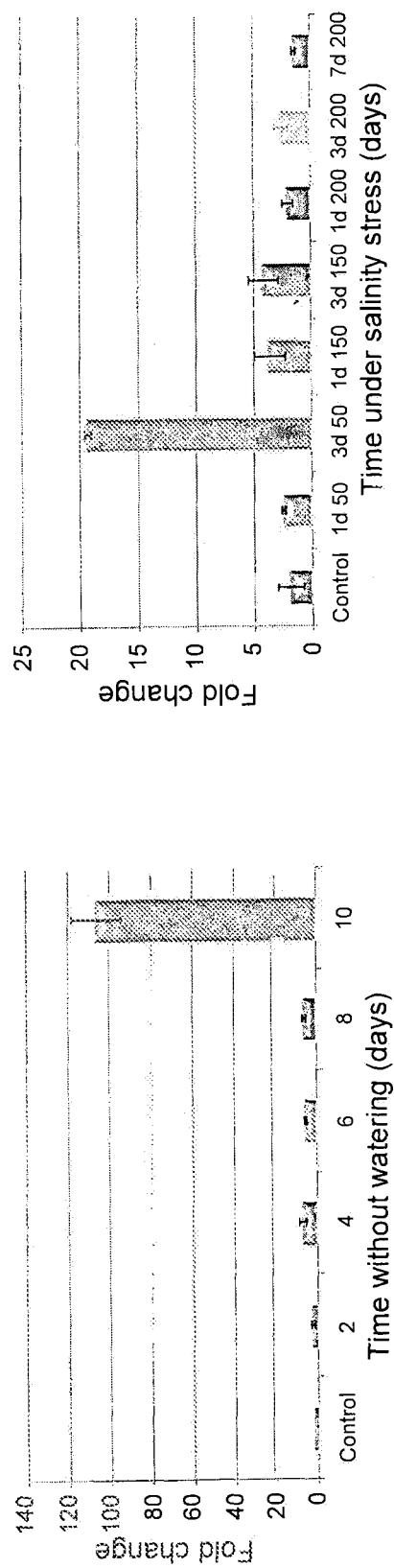
FIG. 7: HaHB11 expression in front of drought and salinity stresses. Sunflower R2 plants were subjected to drought (left panel) or salinity (right panel) stresses as described in the Experimental section. In the right panel, 3d50 means 3 days after 50 mM NaCl addition. Leaf disks were frozen at the times indicated in the figures and HaHB11 transcript levels were quantified by qPCR and normalized with housekeeping ACTIN transcripts. The obtained values were normalized with respect to the value measured in the control sample, arbitrarily assigned a value of one. Error bars correspond to SD among three biological replicas.

We investigated whether abiotic stress factors like drought, salinity and $H_2O_2$ (oxidative stress generator), and some phytohormones related to stress responses regulate the expression of HaHB11. FIG. 6 and FIG. 7 show that in sunflower day-old seedlings, this gene is up-regulated by drought and 6-benzylaminopurine (BAP) and to a lesser extent by abscisic acid (ABA) and gibberellic acid (GA), while in 21-day-old leaves, mannitol (osmotic factor) and ABA seemed to be the major regulators. Other phytohormones tested (indoleacetic acid [IAA]; ethylene (1-amnocyclopropane-1-carboxylic acid [ACC]), salicylic acid [SA], jasmonate [JA] and GA) exhibited either repression, slight induction or no effect on HaHB11 expression.

Altogether, the results indicated that HaHB11 expression is induced by abiotic stress factors, especially by drought and by the hormone related to drought, ABA.

It was observed during these initial studies that drought provoked the highest induction in HaHB11 expression. Because drought stress is usually related to salt stress, we carried out further investigations in order to evaluate the effect of drought and salt stresses on HaHB11 gene expression.

As can be appreciated from FIG. 7, HaHB11 increased its expression until the 101 day after initiation of drought treatment. At this time, the plants were very damaged in appearance, and it was not feasible to continue with RNA analysis. As a control, HaHB4, a well characterized drought responsive gene, was used as a drought marker (data not shown). The expression kinetics of both genes during drought stress were very similar. When a high NaCl concentration (as a salt stress generator) was applied, HaHB11 increased until three days after starting the treatment (see Example 1), and thereafter declined.

Example 3

Obtaining and Characterization of *Arabidopsis* Transgenic Plants Ectopically Expressing HaHB11

Figure 8:
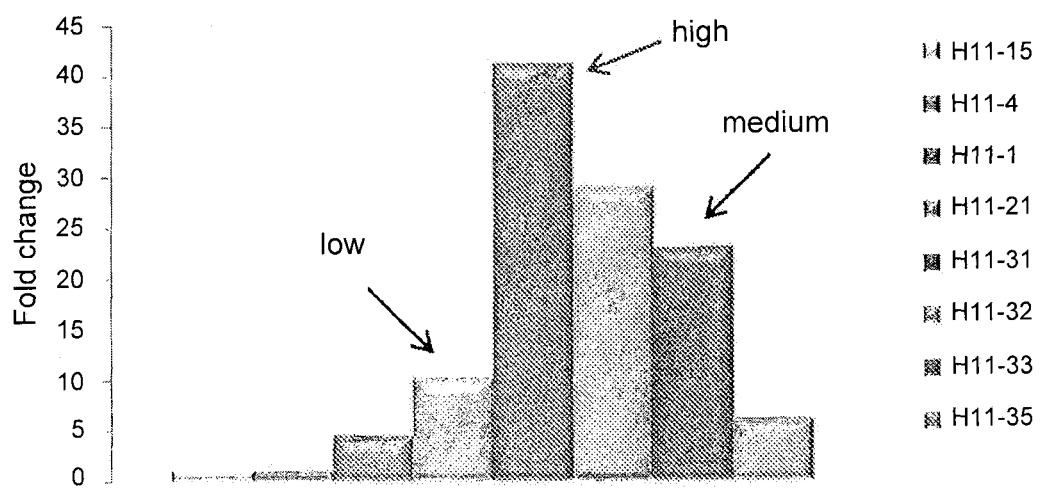
FIG. 8: Relative expression levels of HaHB11 in *Arabidopsis* transgenic plants. RNA was extracted from each genotype (several plants) and transcript levels quantified by qPCR. All the values were normalized with respect to the value measured in line 15, arbitrarily assigned a value of one.

Aiming to analyze HaHB11 function, transgenic (TG) *Arabidopsis* plants expressing this sunflower gene were obtained. The coding region of HaHB11 was fused to the 35S CaMV promoter and this construct was used to transform *Arabidopsis thaliana* plants. Several homozygous lines were recovered and among them, three named thereafter 35S:HaHB11-A, -B, and -C representing high, medium and low expression, respectively, were selected for further analysis (FIG. 8).

Figure 9:
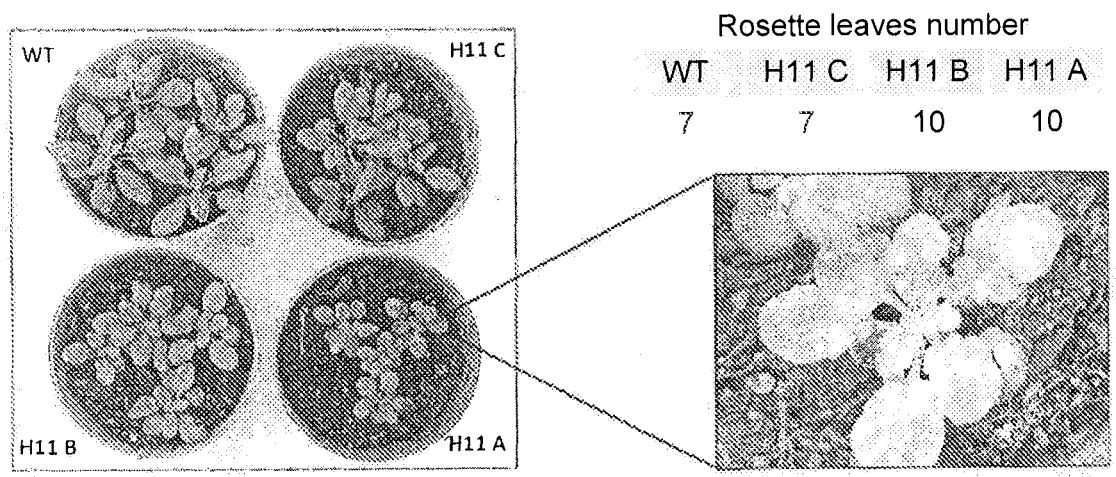
FIG. 9: Phenotype of transgenic plants ectopically expressing HaHB11 compared to WT. Left: 25-day-old plants grown at normal conditions. Right: Number of rosette leaves in the transition from the vegetative to the reproductive stage and an amplification of the photograph of the transgenic leaves.

The transformed plants showed different morphological features when compared with their WT counterparts. Their leaves were more rounded and smaller, the petioles were shorter, and the number of leaves was higher in the transgenic genotypes during the transition from the vegetative to the reproductive phase (FIG. 9).

Figure 10:
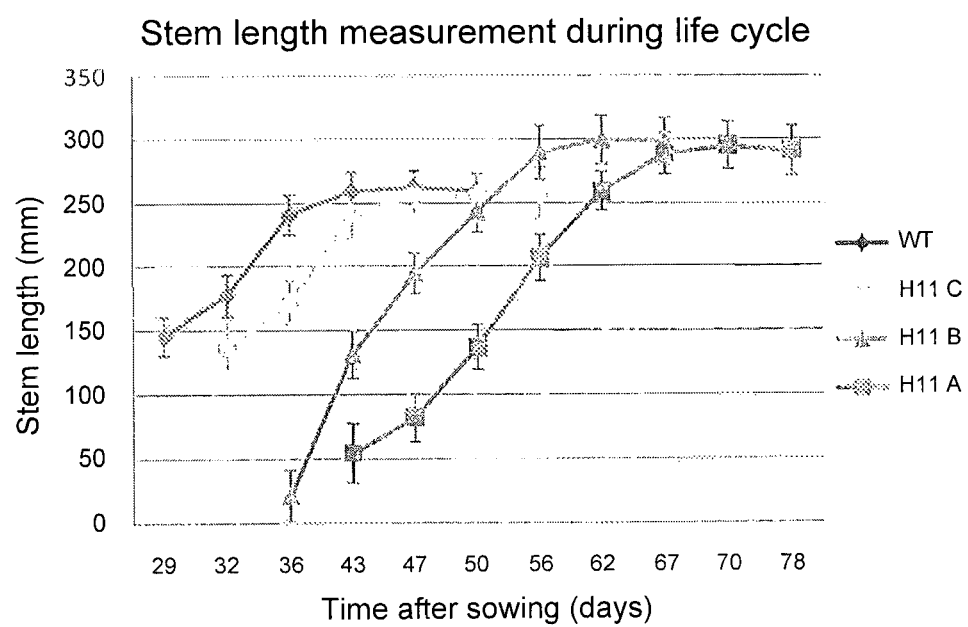
FIG. 10: Stem length measured during the life cycle of 35S:HaHB11 and WT plants. Stem length was measured starting at the transition phase and thereafter every 3-5 days until the end of the life cycle.

Besides the different morphology, transgenic plants exhibited a considerable delay in their life cycle as assessed by stem elongation and flowering time (FIG. 10). At the end of the cycle, transgenic plants were taller than their WT counterparts.

Figure 11:
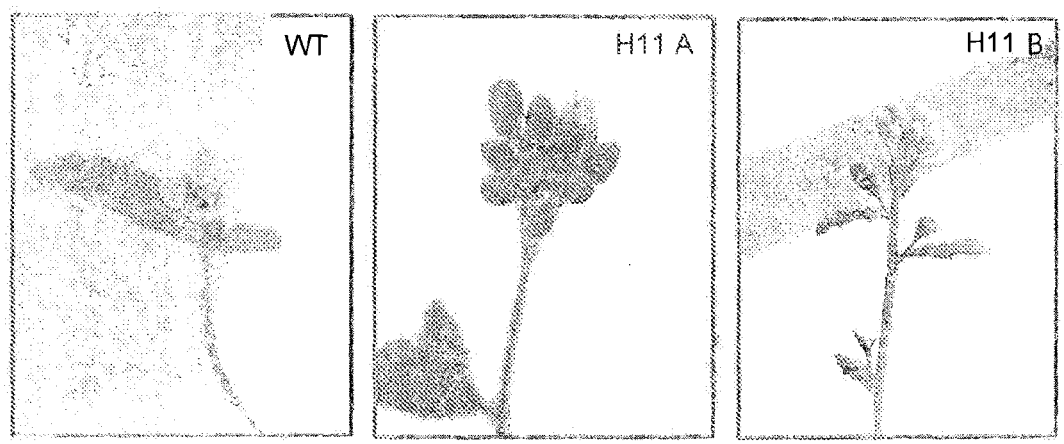
FIG. 11: Inflorescence morphology. Inflorescences of 35-day-old plants grown in standard conditions.

The inflorescence morphology of the transgenic genotypes also presented significant differences (FIG. 11). Transgenic flowers were more compact than in WT plants.

Figure 12:
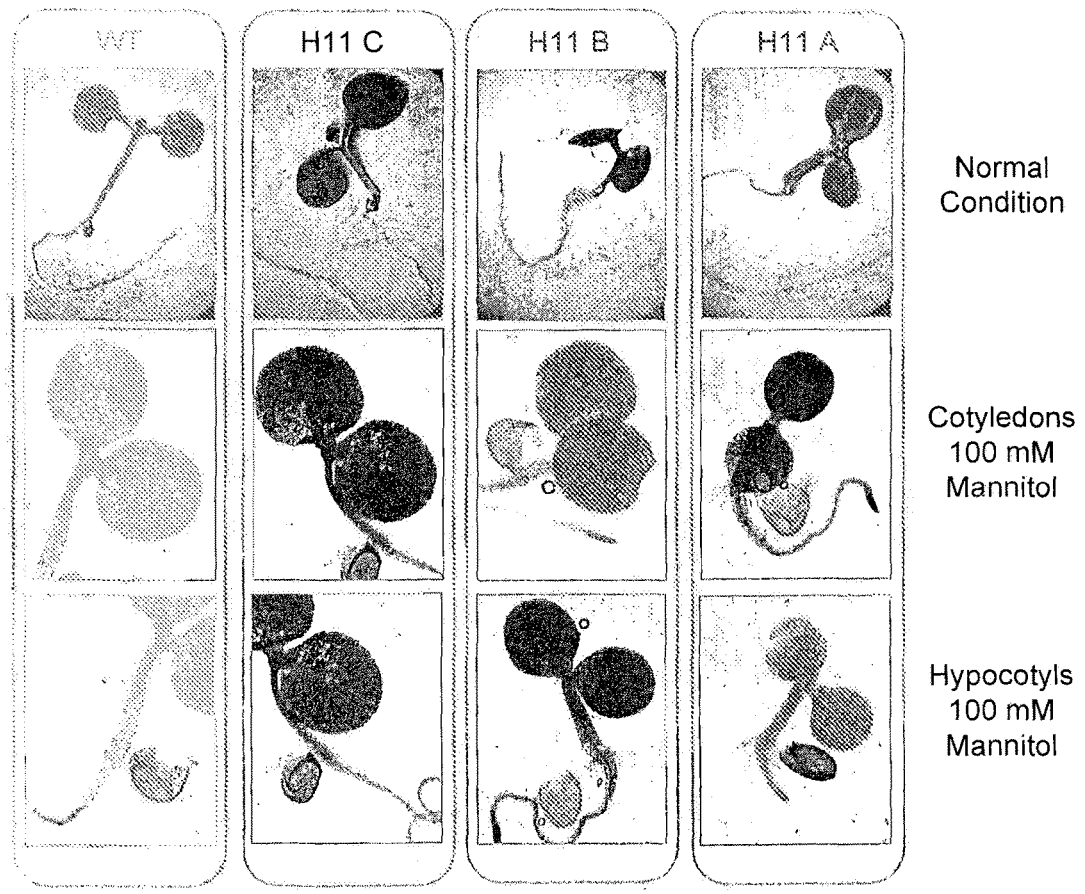
FIG. 12: Phenotype of plants grown in mannitol. Upper panel: plants grown on MS. Middle and lower panel: Plants grown in mannitol 100 mM.

Furthermore, transgenic plants grown on Murashige and Skoog (MS) plates showed more rounded cotyledons, shorter hypocotyls and larger roots. These phenotypic characteristics were very similar to those observed in WT plants grown in 100 mM mannitol (osmotic stress). Notably, transgenic plants did not alter their phenotype when subjected to osmotic stress, suggesting that they were constitutively prepared for such stress (FIG. 12).

Figure 13:
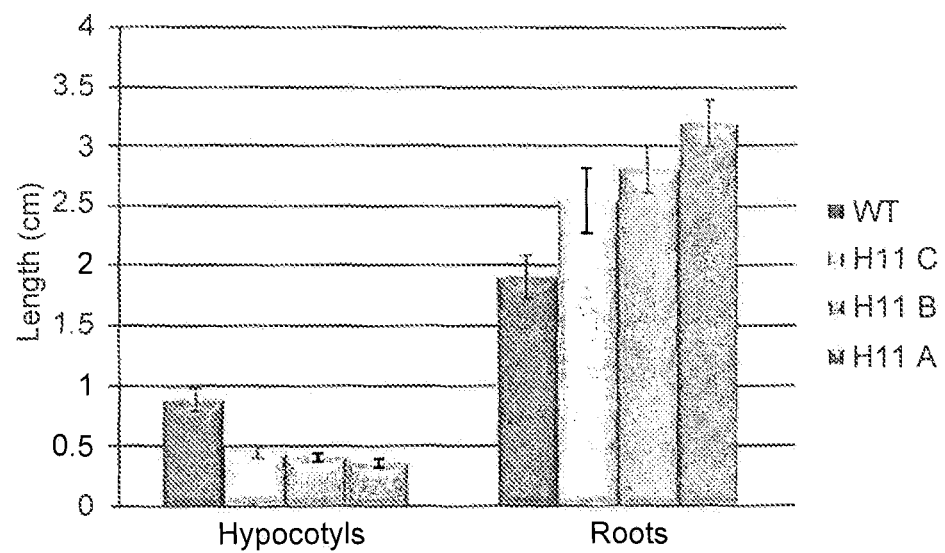
FIG. 13: Hypocotyl and root length. Hypocotyl and root length of 7-day-old plants grown on MS medium was measured. Average lengths and standard deviations were calculated from n=40 seedlings.

Hypocotyl and root length were quantified in order to further characterize these developmental features (FIG. 13).

Example 4

Transgenic Plants Bearing the Construct 35S:HaHB11 were More Tolerant to Several Abiotic Stress Factors Having determined that HaHB11 expression was upregulated by drought, mannitol and ABA, we investigated how transgenic plants (35S:HaHB11) responded to drought at different developmental stages.

Figure 14:
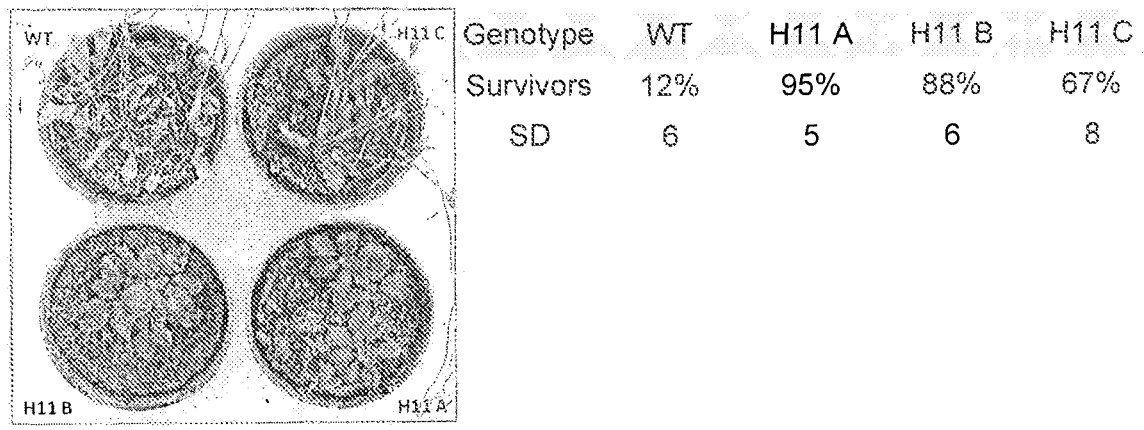
FIG. 14: Transgenic plants are more tolerant to drought than their WT controls. Illustrative assay performed with 25-day-old 35S:HaHB11 and WT plants, water-starved during 15 days. The illustrative photograph was taken during the assay. Right: a table showing the survival rate of each genotype. Statistical analysis was performed with 64 plants from each genotype.

*Arabidopsis* 25-day-old plants were subjected to a severe drought treatment by stopping the water supply during 15 consecutive days. Transgenic plants showed an enhanced tolerance to this treatment and the percentage of survivors after watering was significantly higher than for WT plants (FIG. 14). Subjected to this severe treatment, 67-95% of the transgenic plants survived (depending on the transgene expression level) as compared with 12% of WT plants.

Figure 15:
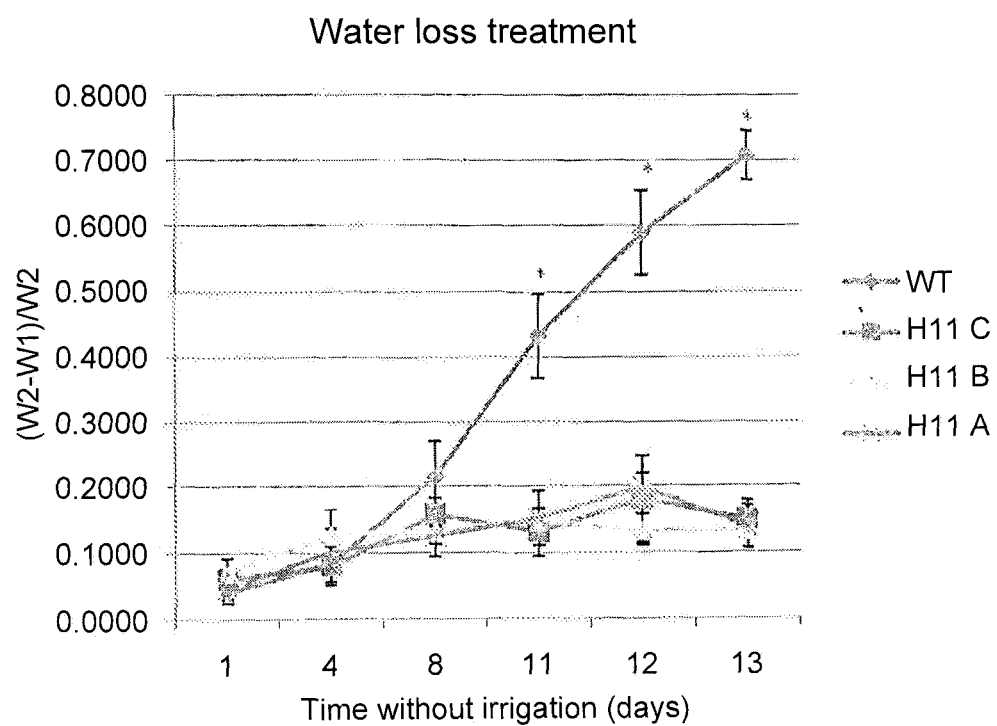
FIG. 15: Water loss treatment under drought stress. Drought tolerance assay performed with 25-day-old 35S:HaHB11 and WT plants during 15 days. Water loss was measured at the times indicated in the figure. W1 is the weight of dehydrated leaves and W2 the weight of re-watered leaves.

In order to elucidate the physiological mechanisms by which HaHB11 conferred drought tolerance, we investigated if transgenic plants consumed less water to live or lost less water due to a lower transpiration rate. To this end, water loss in leaves was quantified in the transgenic and WT genotypes during a drought stress assay (FIG. 15). Water loss was defined as the weight ratio between dehydrated leaves at different times during the drought stress and the same leaves after rewatering.

As demonstrated in FIG. 15, 35S:HaHB11 plants lost less water than WT during the stress treatment, suggesting that their ability to survive could be due to their capacity to retain water under drought stress.

The best known physiological mechanism by which plants are able to retain water is by stomata closure. We therefore decided to observe plant stomatal closure under water stress.

Figure 16:
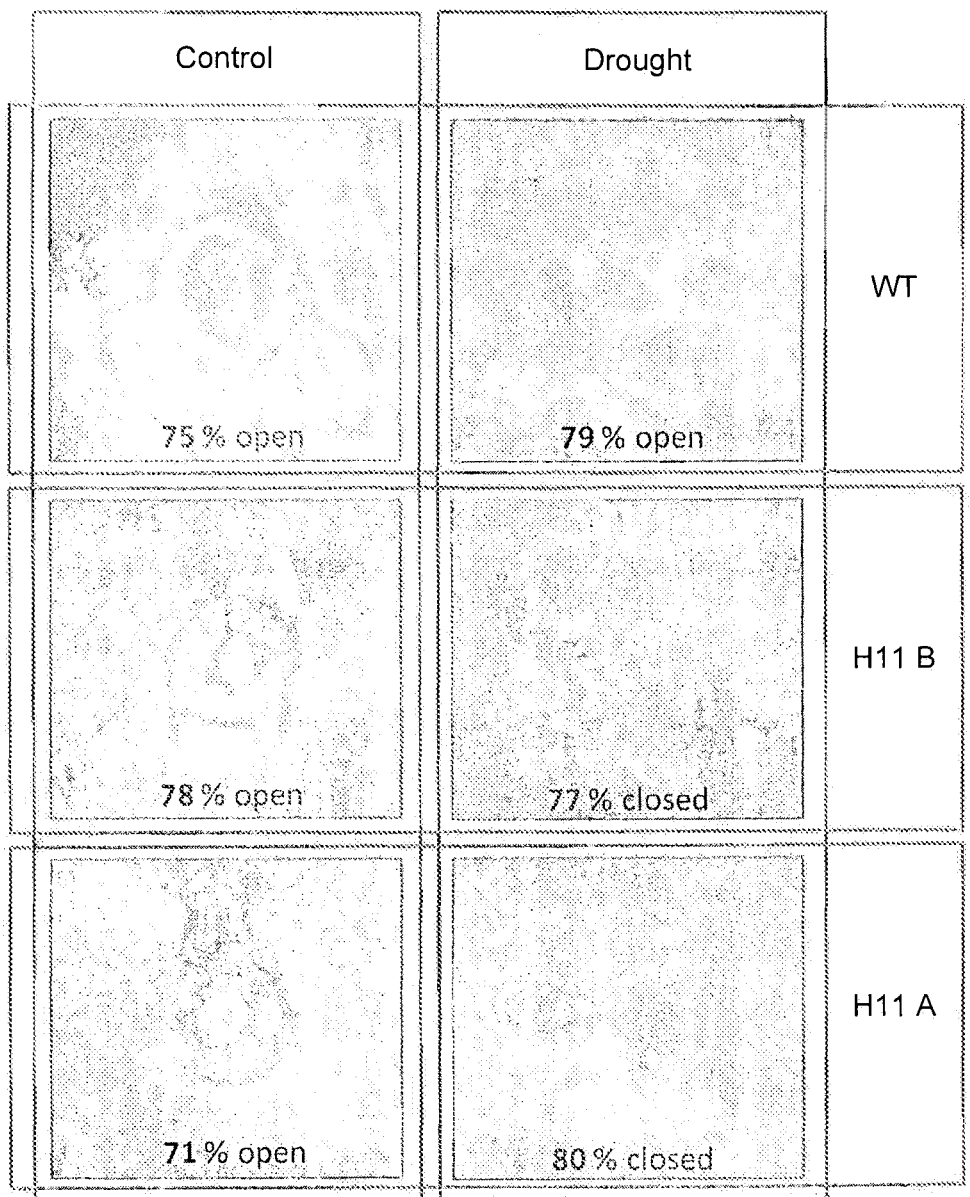
FIG. 16: Stomatal closure under drought stress. 25-day-old 35S:HaHB11 and WT plants grown on MS medium and then dehydrated on paper during 15 minutes. Photographs were taken using an optical microscope. The observation was performed with n=50 stomata for each genotype.

When plants were subjected to drought stress, transgenic plants closed their stomata faster than WT plants (FIG. 16) explaining the results shown in FIG. 15.

To further analyze this response, stomata closure/opening was analyzed in plants grown in soil and subjected to drought.

Figure 17:
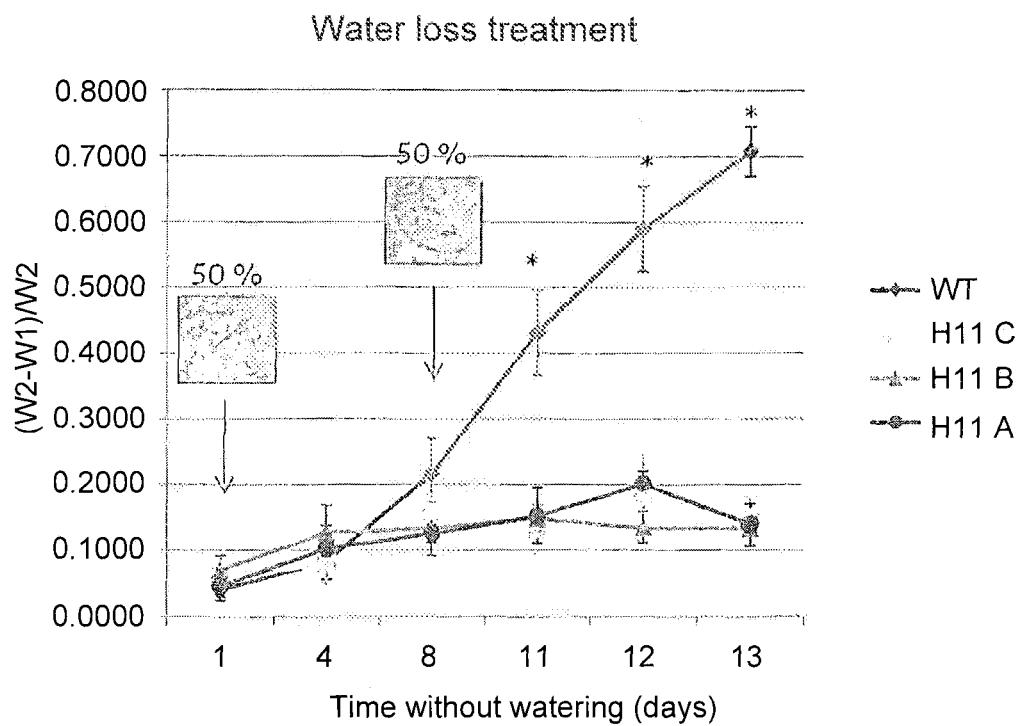
FIG. 17: Stomatal closure during water stress treatment in plants grown on soil. 25-day-old 35S:HaHB11 and WT plants were subjected to drought during 15 days. Water loss during the treatment was quantified at the times indicated in the figure as described above. W1 is the weight of dehydrated leaves and W2 the weight of re-watered leaves. Stomatal closure was estimated by microscopic observation at specific points during the assay.

As can be appreciated from FIG. 17, 35S:HaHB11 plants closed 50% of their stomata the first day of the drought treatment while WT plants achieved the same percentage on the 8th day (FIG. 17), indicating that transgenic plants were able to more quickly sense the stress and, consequently, close their stomata.

Because ABA is intimately related to stomatal closure we decided to evaluate if the more rapid stomata closure observed in transgenic plants was related to this hormone action. Plants were grown on MS and treated with ABA for 1 hour.

Figure 18:
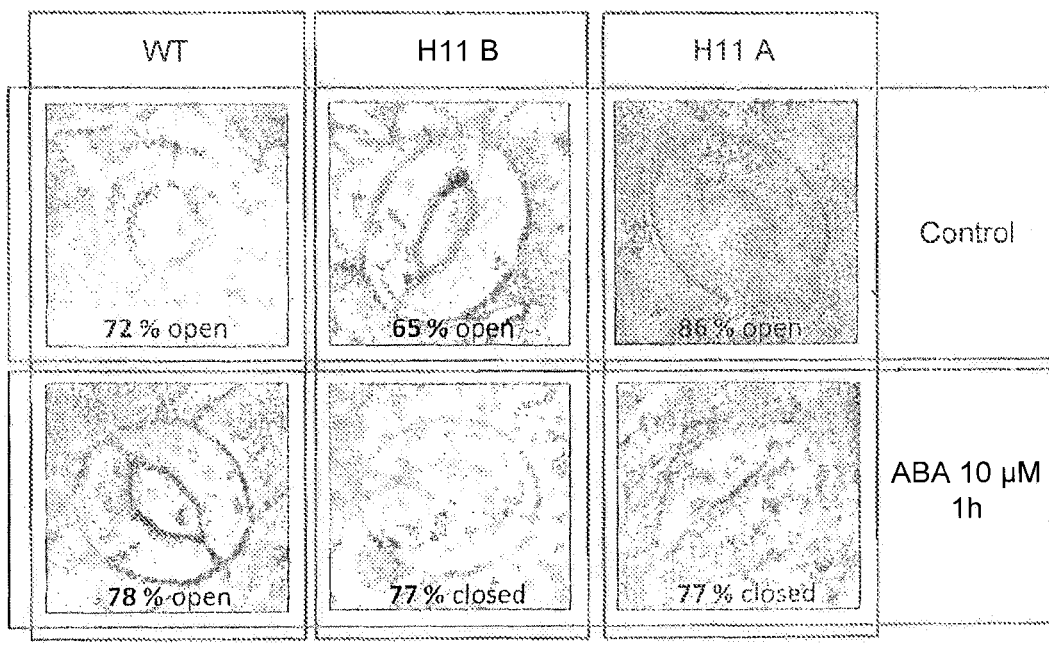
FIG. 18: Effect of ABA 10 uM on stomata closure in WT and transgenic plants. 25-day-old 35S:HaHB11 and WT plants grown on MS medium were treated with ABA 10 uM for 1 hour. Stomatal closure was quantified before and after ABA treatment in n=50 stomata.

ABA treatment provoked similar results as drought; 65-86% of transgenic stomata were closed after one hour while only 22-28% WT stomata were closed after the same period (FIG. 18).

When water stress treatments were performed with 35S:HaHB11 plants, we observed a remarkable difference in the humidity state of the pots bearing these plants as compared with the pots bearing WT plants; they were always more wet. This interesting observation suggested that, besides the lower water loss, an additional mechanism implying a lower water uptake under stress conditions could be playing a role in drought tolerance triggered by HaHB11. Aiming to test this hypothesis, water consumption was analyzed in transgenic and WT plants during a drought treatment.

Figure 19:
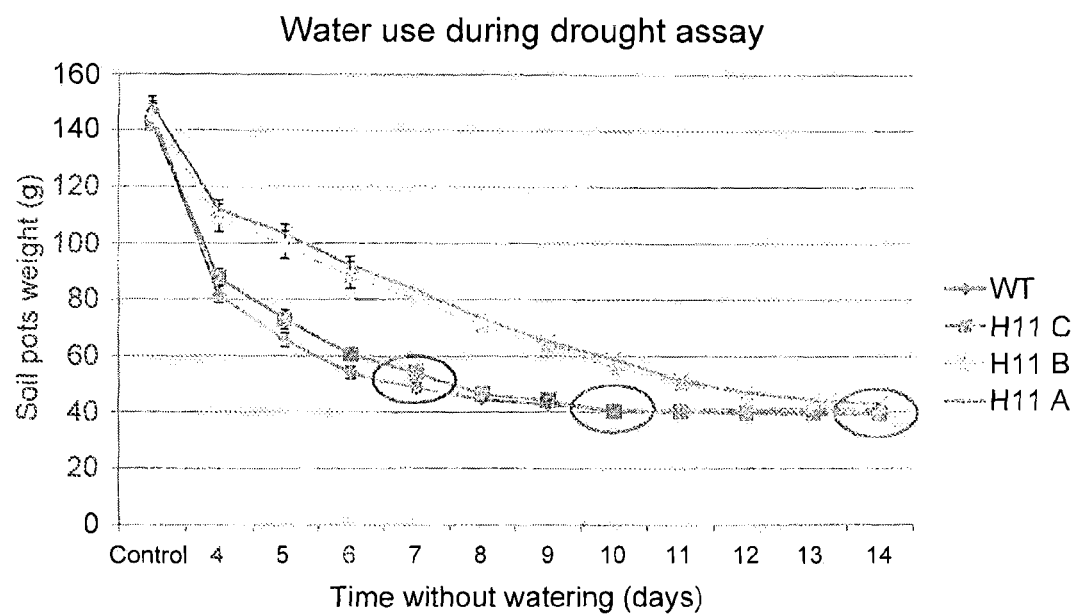
FIG. 19: Water use efficiency during drought assay. 25-day-old 35S:HaHB11 and WT plants grown on soil and dried during 14 days. Soil pots were weighed every day during the assay. Circles indicate the average day on which plant of each genotype died.

For this purpose, 25-day-old plants were subjected to drought by cessation of watering. Every day thereafter, the pot was weighed. FIG. 19 shows that the pots bearing the transgenic lines with high and medium expression HaHB11 levels retained more water (were heavier) than those bearing WT or transgenic plants with low level HaHB11 expression. These results suggested that transgenics were able to tolerate drought not only because they closed their stomata faster than WT plants but because they had the ability to survive with a lower water supply.

Figure 20:
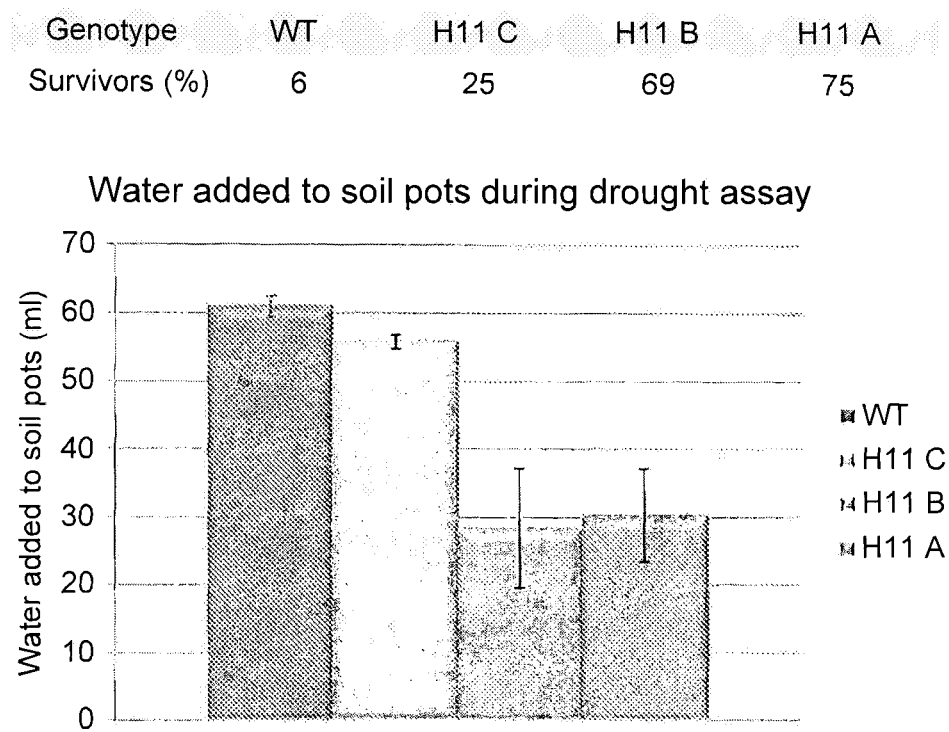
FIG. 20: Transgenic plants consumed less water than WT during a stress treatment. 25-day-old 35S:HaHB11 and WT plants were grown on soil and watering was stopped during 14 days. Soil pots were weighed every two days during the assay and water was added to those that needed it to maintain the same water volume in all the pots. In general, high expressing HaHB11 transgenic plants did not need any addition of water.

To further investigate the drought tolerance mechanism in HaHB11 plants and to corroborate if such tolerance resulted from combined or cooperative responses including stomata closure and optimized efficiency in water use, a drought assay in which the same amount of water was maintained in the pots was carried out. FIG. 20 shows that WT plants needed more water (twice) than 35S:HaHB11 plants during the assay to maintain the same pot weight. Although the stress applied was less severe, when survivors were counted at the end, there were fewer surviving WT than transgenic plants (FIG. 20).

Altogether, the results indicated a dual tolerance mechanism triggered in 35S:HaHB11 plants. Under severe drought conditions, transgenic plants exhibited more efficient water usage due to both lower transpiration and lower consumption rates.

Example 5

Figure 21:
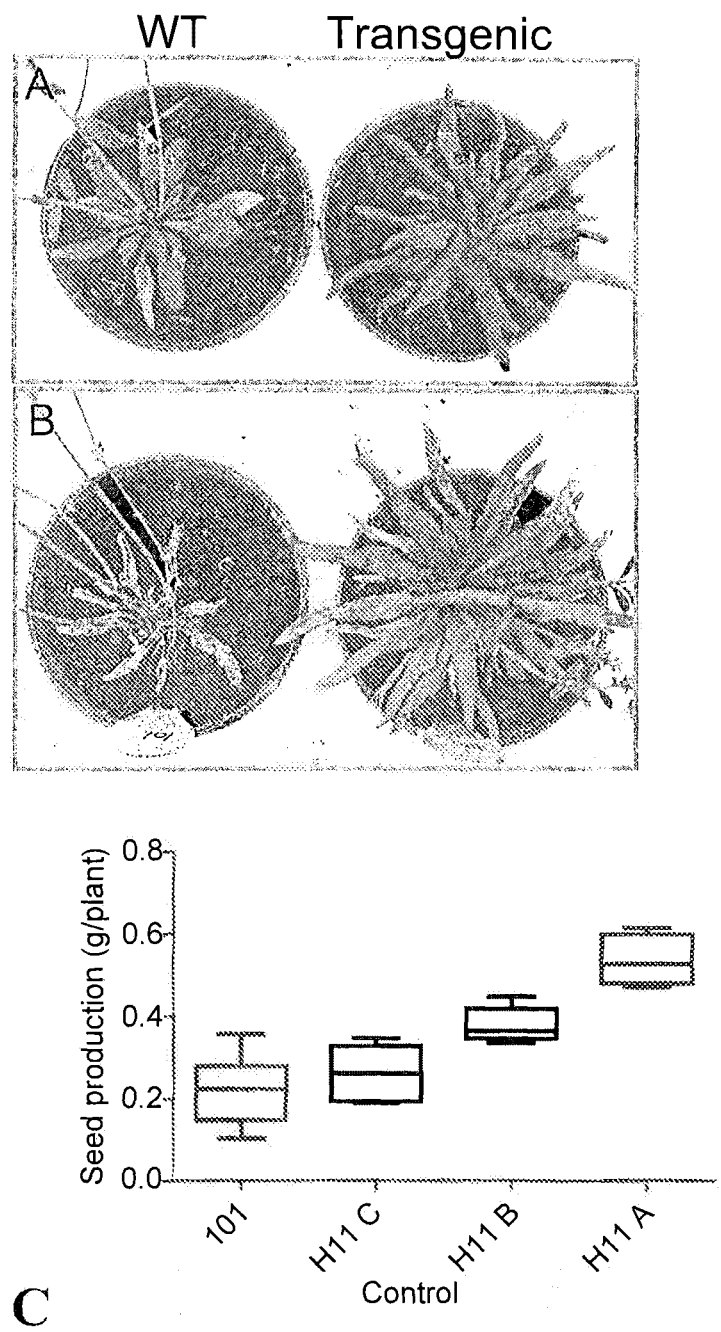
FIGS. 21A-C: Transgenic plants bearing the construct 35S:HaHB11 exhibited a larger rosette and a significantly higher yield A: 40-day-old WT and 35S:HaHB11 plants were grown on soil and normally irrigated during the whole life cycle. B: the same but with 50-day-old plant. C: Yield was calculated from an experiment performed with 12 plants of each genotype.

Transgenic 35S:HaHB11 *Arabidopsis* Exhibited Increased Yield Under Control Conditions Stomata closure is a natural mechanism of drought tolerance triggered by plants, and several genes are involved. Normally, stomata closure is a first response when plants sense the drought and results in a loss in productivity due to the decrease in the photosynthetic rate. A significant problem for farmers is that climate and humidity cannot be predicted with certainty and, as a consequence, drought tolerant plants that produce less in watered seasons are not convenient and hence, such plants are less desirable. Since in most cases in the field, drought stress is mild rather than severe, we evaluated how transgenic plants behave in non-stressed conditions. Yield of 35S:HaHB11 transgenic *Arabidopsis* and wild plants was quantified in standard growth conditions and the results shown in FIG. 21. Under these standard growth conditions, transgenic plants had a larger rosette and, as a consequence, a higher yield of seed.

Example 6

Figure 22:
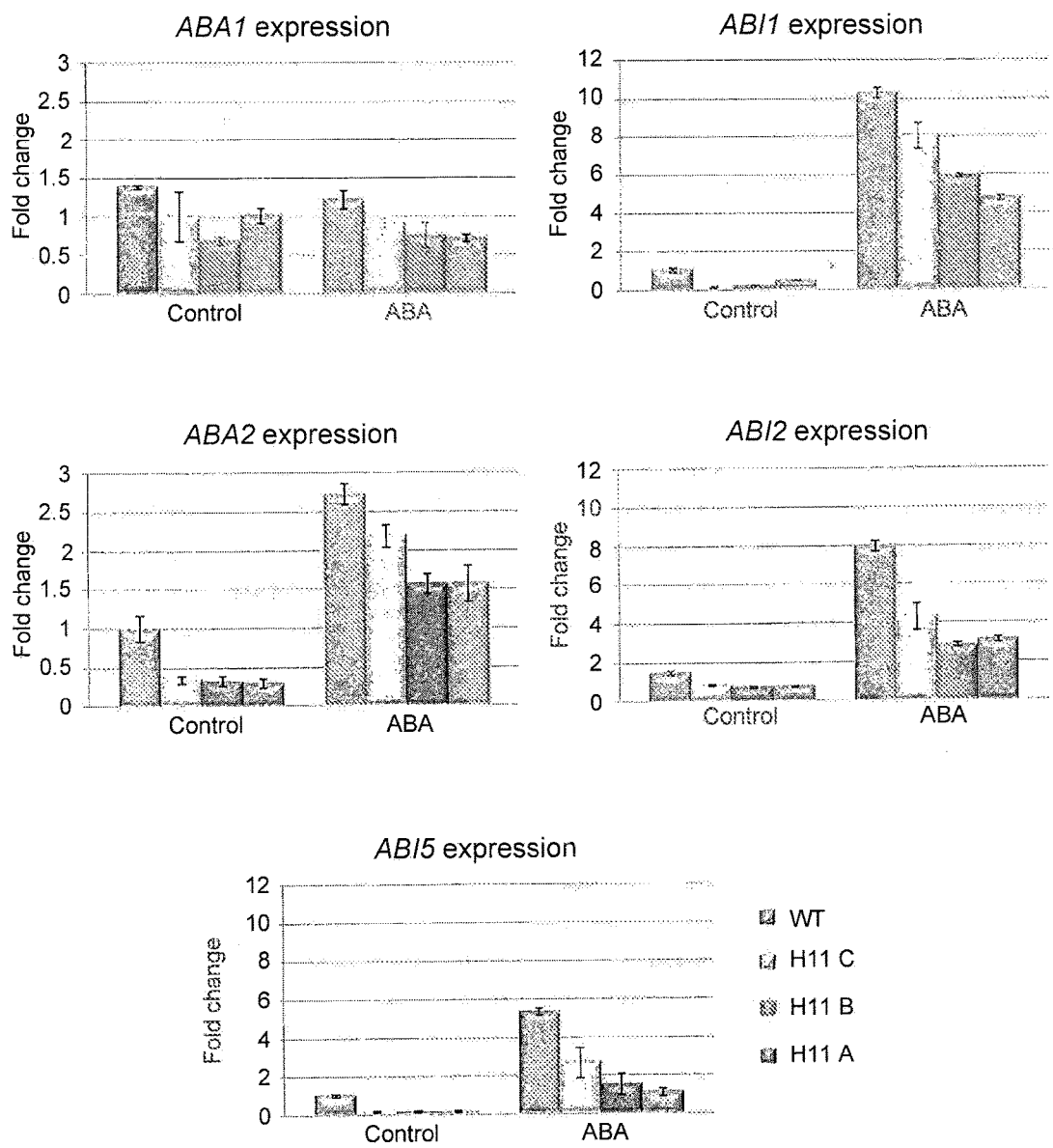
FIG. 22: Expression levels of selected genes involved in ABA synthesis and signaling in 35S:HaHB11 and WT plants. RNA from 21-day-old 35S:HaHB11 and WT plants grown on MS medium treated with ABA 100 1-1M during 1 hour were isolated and quantified by qPCR. Statistical analysis was performed from three biological triplicates.

A Complex Molecular Mechanism Takes Place in HaHB11 Plants to Trigger Drought Tolerance ABA biosynthesis and signaling pathways are intimately related to most known mechanisms of abiotic stress tolerance. Aiming to evaluate the phenotype of HaHB11 plants in more detail, the expression levels of genes participating in ABA biosynthesis and signaling and those involved in stress tolerance were quantified in HaHB11 overexpressors treated or untreated with ABA. RNA from transgenic and WT genotypes was isolated from control or ABA treated plants, and 11 selected gene transcripts were quantified. FIG. 22 shows the results obtained from three independent assays. Transcript levels of five genes involved in ABA biosynthesis and signaling (ABA1, ABA2, ABI1, ABI2, ABI5) were consistently and significantly lower in ABA-treated 35S:HaHB11 plants than in WT (FIG. 22).

COR (COR15A and COR47) and RD29A genes have been reported to play key roles in the abiotic stress response as protectors. Their transcript levels were significantly reduced in 35S:HaHB11 plants compared with WT (FIG. 23).

Figure 23:
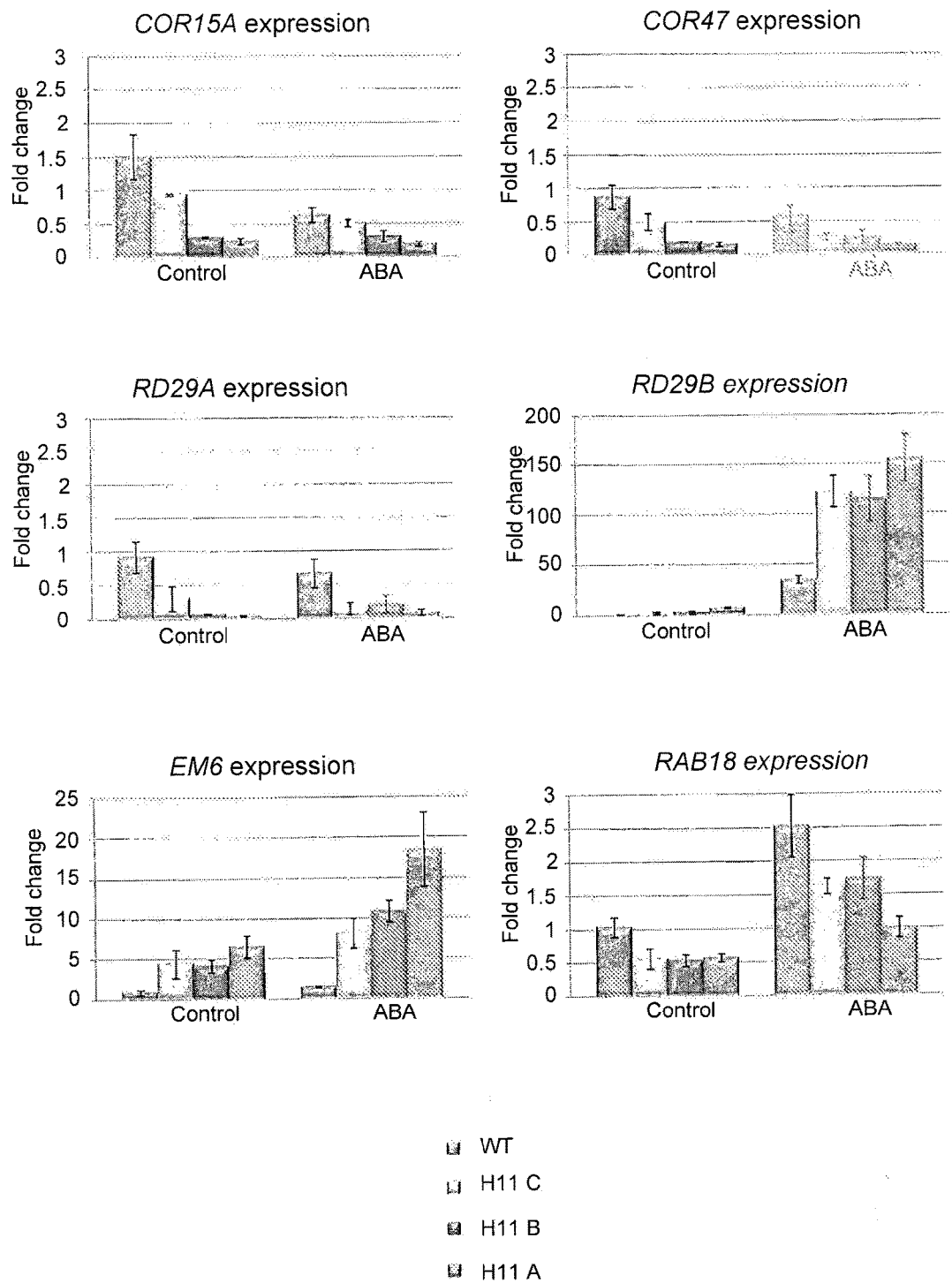
FIG. 23: Expression levels of genes involved in abiotic stress protection in 35S:HaHB11 and WT plants. RNA from 21-day-old 35S:HaHB11 and WT plants grown on MS medium were treated with ABA 100 1-1M during 1 hour were isolated and analyzed by qPCR. Statistics analysis was performed with three biological triplicates.

On the other hand, the expression levels of RD29B, EM6 and RAB18 were higher in 35S:HaHB11 than in WT plants (FIG. 23).

These results indicate that HaHB11 triggers a complex pathway in which genes involved in ABA biosynthesis and ABA-independent signaling pathways are down-regulated after drought, salt or cold induction, while genes involved in ABA-dependent signaling pathways are up-regulated. The up-regulation of HaHB11 by ABA and the down-regulation of ABA biosynthesis genes is suggestive of a negative feedback that regulates ABA concentration after stress.

Example 7

Figure 24:
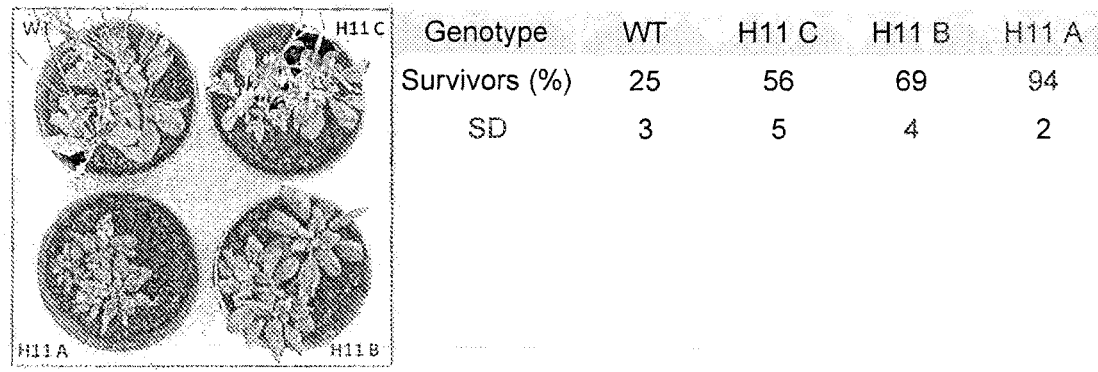
FIG. 24: Transgenic plants were tolerant to salinity stress. 21-day-old 35S:HaHB11 and WT plants were watered with increasing NaCl concentrations up to 400 mM during a 21 day period. The photograph was taken 7 days after the end of the assay. Statistics was performed with n=32 plants for each genotype.

Transgenic Plants Bearing the Construct 35S:HaHB11 were More Tolerant to Salt Stress Since stress caused by drought and high salinity are usually related and taking into account the up-regulation of HaHB11 by salt, transgenic plants were tested for their ability to tolerate salt stress as compared with WT plants. Twenty one-day-old 35S:HaHB11 and WT plants were watered with increasing NaCl concentrations up to 400 mM for 21 days. As shown in FIG. 24, transgenic plants looked healthier during the treatment than their controls and at the end, exhibited a higher survival rate.

Example 8

Isolation and Partial Characterization of 466 bp Fragment of the HaHB11 Promoter A 466 bp segment upstream from the transcription initiation site and corresponding to the 5' non coding sequence and a partial promoter segment of HaHB11 was isolated from a BACs genomic library (ProH11 (short); SEQ ID NO:5). Within this DNA segment different cis-elements were identified using the PLACE database (at world wide web dna.affrc.go.jp/PLACE) including a LTRE (Low Temperature Responsive Element), a DRE (Dehydration Responsive Element) and an ABRE (ABA Responsive Element) located at 318 and 326 bp from the +1 (position 266 of SEQ ID NO:4 (−strand); see, schematic in FIG. 1A).

Figure 25:
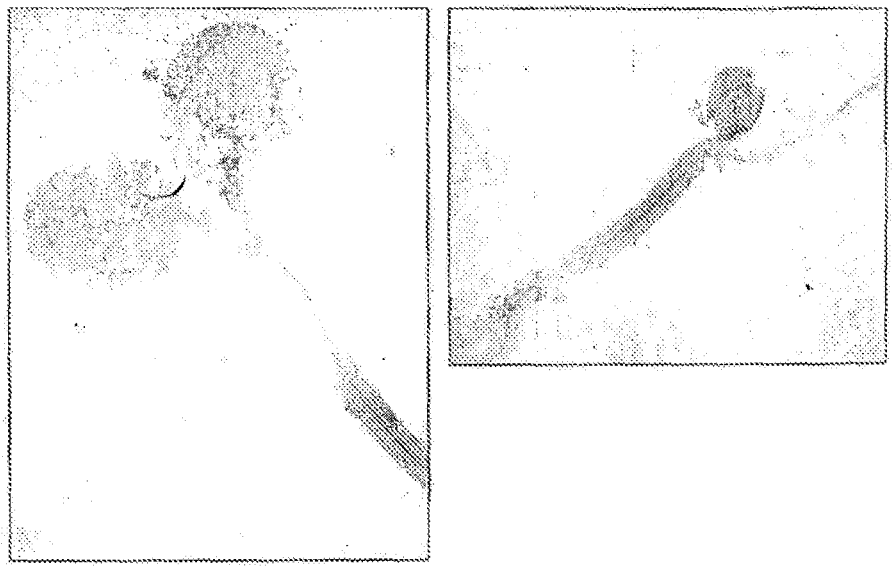
FIG. 25: Histochemical GUS staining in PrH11:GUS plants. GUS detection in 7-day-old PrH11:GUS plants grown on MS medium.
Figure 26:
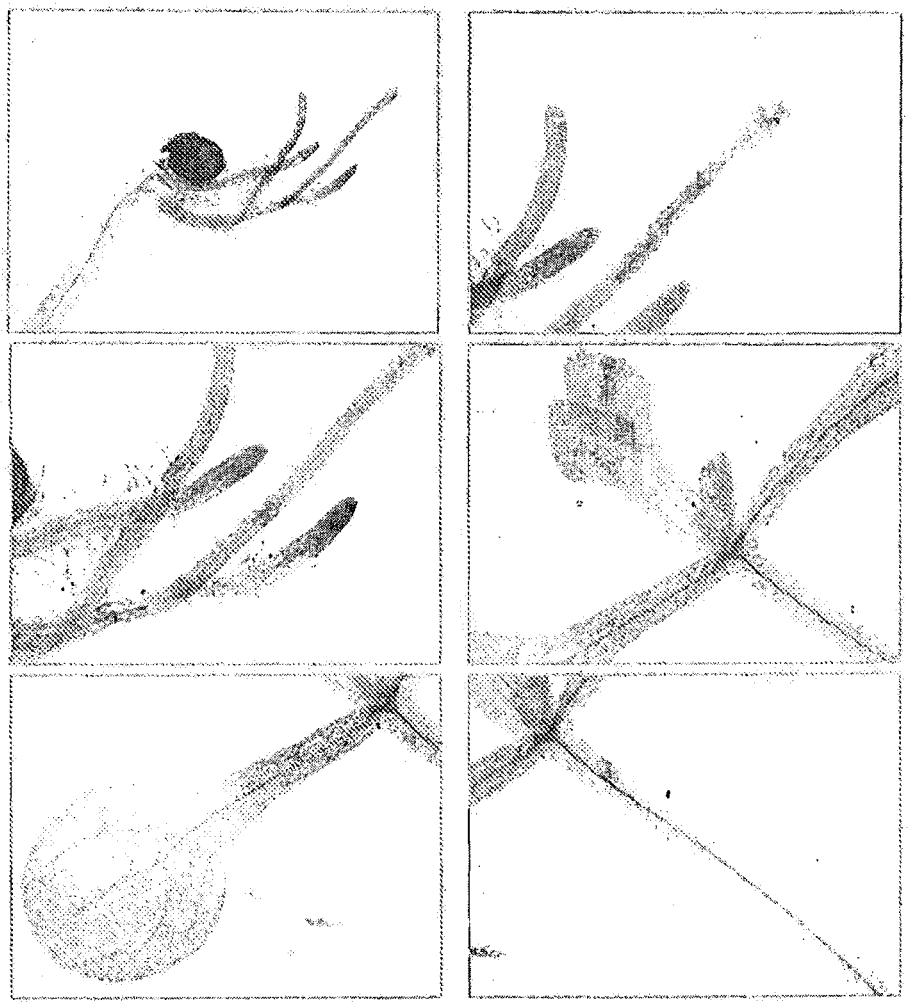
FIG. 26: Histochemical GUS staining in PrH11:GUS plants. GUS detection in 14-day-old PrH11:GUS plants grown on MS medium.

This DNA fragment was cloned to direct expression of the GUS reporter gene as described in Example 1. This construct was used to transform *Arabidopsis* plants, which were then analyzed by histochemistry. FIG. 25 and FIG. 26 show GUS expression pattern as directed by the HaHB11 short promoter fragment. As it can be observed, GUS is expressed in the hypocotyl of *Arabidopsis* seedlings and in the roots and meristematic regions of 25-day-old plants.

Example 9

HaHB11 Transgenic Plants were Tolerant to Submergence

In order to further investigate the molecular mechanism by which HaHB11 conferred drought tolerance to transgenic plants, an exploratory transcriptome analysis was performed with RNA obtained from sunflower transiently transformed leaf disks. This analysis indicated that several genes were up-regulated such as ADH (Alcohol dehydrogenase), PDC (Pyruvate Decarboxylase) and SS (Sucrose synthase), which are putative homologs to *Arabidopsis* genes reported to be involved in submergence tolerance.

In view of these observations, we decided to evaluate the performance of HaHB11 as a transgene during a stress caused by submergence. Twenty one-day-old plants were submerged in water during six consecutive days. After that, the plants were placed in a dry tray to recover themselves and were normally irrigated thereafter. FIG. 27a shows the plants after recovery; as it can be appreciated, HaHB11 plants tolerated this severe stress better and exhibited a higher survival rate than their controls. Moreover, the chlorophyll content of transgenic plants immediately after the treatment was higher than in control plants (FIG. 27b)

indicating that the transgenic plants were somehow protected from the stress and could better preserve cell and organelle integrity.

Submerged plants do not only suffer during submergence but also during desubmergence by dehydration. Cell death is more likely to occur during this after stress period. In order to evaluate transgenic plant behavior after submergence treatment, water loss was quantified in both genotypes, WT and transgenic. FIG. 27c shows the obtained data indicating that transgenic plants were able to better tolerate this after stress period than their non-transformed counterparts.

Example 10

HaHB11 Transgenic Plants are Tolerant to Waterlogging

Waterlogging, caused by flooding, long periods of rain and poor drainage is a serious constraint with damaging effects (Visser et al., Ann. Bot. 91:107-109 (2003)). The imbalance between slow diffusion and rapid consumption of oxygen in plant roots drastically reduces the oxygen supply (Zou et al., Plant Biol. 10:189-215 (2010)). The rapidly depleted oxygen from the submerged root zone is sensed by the plant, which adjusts the expression of genes induced by anaerobiosis. Flooding induces or accelerates plant senescence in tobacco, tomato, sunflower, barley, peas, wheat, maize and soybean (Burrows et al., Plant Physiol. 22:1105-1112 (1969); Drew and Sisworo, New Phytol. 79:567-571 (1977); Olymbios et al., J. Am. Soc. Hort. Sci. 52:485-500 (1977); Jackson, Sci. Food Agric. 30:143-152 (1979); Trought et al., Plant Soil 54:77-94 (1980); VanToai et al., Crop Sci. 34:1112-1115 (1994)). The most obvious symptom of flooding injury is leaf chlorosis, which is followed by necrosis, defoliation, cessation of growth and premature plant death.

To evaluate the damage induced by waterlogging, chlorophyll content after waterlogging stress was quantified in the different genotypes. FIG. 28 shows that WT plants exhibited a chlorophyll concentration of 440-480 ug/g tissue after the treatment, while 35S:HaHB11 plants showed an increased chlorophyll concentration (495-535 ug/g tissue).

It has been reported that many plants that survive flooding die immediately afterwards (Sullivan et al., Crop Sci. 41:1-8 (2001)). Thus, the post-flooding period can be as injurious as the flooding period itself. After the waterlogging treatment, 35S:HaHB11 plants grew better than WT, indicating that HaHB11 conferred tolerance to the after-waterlogging stress. FIG. 29 illustrates the appearance of the different genotypes after six days of recovery.

Example 11

HaHB11 is a Sunflower Divergent Transcription Factor

HaHB11 encodes a 175 amino acid protein belonging to subfamily I of HD-Zip transcription factors (Arce et al., BMC Plant Biol. 11:42 (2011)). Phylogenetic trees based on the HD-Zip domain family of proteins from several species suggested this protein belongs in the same group as AtHB7 and AtHB12 from *Arabidopsis thaliana*, HaHB4 from *Helianthus annuus* and MtHB1 from *Medicago truncatula* (Chan et al., Biochim. Biophys. Acta 1442:1-19 (1998); Ariel et al., Trends Plant Sci. 12:419-426 (2007); Ariel et al., Plant Cell 22:2171-2183 (2010)). However, more recent phylogenetic trees indicate that neither HaHB11 nor HaHB4 can be resolved into the same group as these putative homologs; both sunflower genes are divergent and were not resolved into any of the six HD-Zip 1 groups in which this subfamily has been divided based on structural features outside of the conserved HD-Zip domain (Arce et al., BMC Plant Biol. 11:42 (2011)). Thus it was interesting to functionally characterize these genes that lack orthologs in model species.

The expression pattern of HaHB11 was analyzed in 7- and 21-day old sunflower plants and by obtaining transgenic *Arabidopsis* bearing a 452 bp promoter segment directing the reporter gen GUS. The results obtained with both methodologies indicated that HaHB11 is expressed in hypocotyls and cotyledons, in seedlings and significantly in 21-day-old roots. This expression was up-regulated by drought, mannitol, NaCl and ABA. This pattern presented similarities to those of AtHB7 and AtHB12 which were also up regulated by drought (Olsson et al., Plant Mol. Biol. 55:663-677 (2004)), NaCl and ABA (Shin et al., Biochem. Biophys. Res. Commun. 323:534-40 (2004); and Henriksson et al., Plant Physiol. 139:509-518 (2005)). In particular, the expression in leaves and roots was similar to that of AtHB7, while AtHB12 expression was weak in roots, at least under standard growth conditions (Henriksson et al., Plant Physiol. 139:509-518 (2005)).

The *Medicago truncatula* gene, MtHB1, was expressed in the root apical meristem as well as in the lateral roots emergence region (Ariel et al., Plant Cell 22:2171-2183 (2010)) in contrast with HaHB11 which is expressed in the entire root with the exception of the apical meristem.

The expression of GUS directed by the HaHB4 promoter was evident in the root central cylinder and in the lateral roots emergence region (Dezar et al., Plant Sci. 169:447-459 (2005)) and the expression of this gene was up-regulated by drought and ABA as was the case for all the genes discussed above including HaHB11.

35S:HaHB11 plants demonstrated stomata closure under stress conditions or in response to ABA treatment. Furthermore, seeds were more sensitive to this hormone in the germination stage. The plant studies indicated an enhanced synthesis or sensitivity to ABA. However, transcript quantification from genes involved in these processes (synthesis and ABA perception) suggested a different, more complex scenario.

ABA1, ABA2 and ABA3 transcripts have been reported to be induced by water and salt stresses, contributing to the enhancement of ABA levels in plants affected by such stresses (Ding et al., J. Genet. Genom. 36:17-29 (2009)). The expression of these genes was lowered in HaHB11 plants, suggesting that ABA synthesis in these plants is diminished. ABI1 and ABI2 were reported as negative regulators of the ABA response, and plants over-expressing these genes presented a reduced sensitivity to the hormone (Raghavendra et al., Cell 15:395-401 (2010)). Since these two genes were repressed in HaHB11 plants, the enhanced sensitivity to ABA in these plants could be explained in this way.

ABI5 is a transcription factor belonging to the bZip family and it was reported as a positive regulator of the ABA response. We expected to observe AB/5 over-expressed in HaHB11 plants; however, the expression of this gene was repressed under standard growth conditions and, although it was normally induced by ABA, it remained repressed in the transgenic plants treated with ABA as compared with WT plants.

ABA induces ABI5 accumulation by transcriptionally inducing expression of this gene and stabilizing the encoded protein (Lopez-Molina et al., PNAS 98:4782-4787 (2001)).

This stabilized protein was able to bind the ABRE cis elements present in the regulatory regions of several ABA responsive genes (Hirayama and Shinozaki, Trends Plant Sci. 12:343-351 (2007)); Carles et al., Plant J. 30:373-383 (2002)). Plants over-expressing ABI5 were described as more tolerant to different abiotic stresses (Nakashima and Yamaguchi-Shinozaki, Japan Agricultural Research Quarterly. 39:221-229 (2005)), making it difficult to understand why it was repressed in HaHB11 plants.

COR15A and COR47 are regulated by the signal cascade mediated by CBF genes (Thomoshow, Plant Physiol. 125: 89-93 (2001)), and they do not need ABA to be expressed under abiotic stress conditions (Yamaguchi-Shinozaki and Shinozaki, Plant Cell 6:251-264 (1994)). Transcripts of these two genes were repressed in HaHB11 over-expressing plants grown in normal conditions. When these plants were subjected to freezing transcription levels of each of these genes did not appear to differ compared to that observed in WT plants. These results are in accordance with those described by Ding et al., J. Genet, Genom. 36:17-29 (2009), in which MYB15 over-expressers tolerated drought better than WT but not freezing temperatures. MYB15 over-expressers exhibited repression of either CBF or repression of genes downstream in the CBF cascade; like COR15A, COR47 and RD294.

RD294 and RD29B have been described as ABA responsive genes. RD29A is regulated both in an ABA dependent and ABA independent way. In its promoter region there are cis acting elements responsive to drought (DRE) and also cis acting elements responsive to ABA (ABRE; Narusaka et al., Plant J 34:137-148 (2003)). Considering these observations, its regulation by abiotic stresses does not require the presence of ABA and can be explained by the presence of DRE elements (Yamnaguchi-Shinozaki; Plant Cell 6:251-264 (1994)). On the other hand, RD29A has been described as exclusive to the ABA signaling pathway. This gene was repressed in 35S:HaHB11 plants, and this repression remained when the plants were treated with ABA. In contrast, RD29B was induced in 35S:HaHB11 plants grown under normal conditions and this induction increased 20-40 fold with ABA treatment. These results are in agreement with those obtained by measuring COR transcripts and indicate that HaHB11 is a repressor of the ABA independent pathway and an inducer of the ABA dependent one.

EM6 encodes a LEA protein involved in seed maturation and is necessary for normal seed development (Manfre et al., Plant Physiol. 140:140-149 (2005)). EM6 transcripts are induced in HaHB11 plants grown under standard conditions and increase even more when the plants are treated with ABA. ABI5 binds an ABRE located in the EM6 promoter (Caries et al., Plant J. 30:373-383 (2002)), and AB15 was repressed in HaHB11 plants, suggesting that HaHB11 positively regulates EM6 by an ABI5 independent pathway.

RAB18 is repressed in HaHB11 plants both in normal conditions or when treated with ABA. Surprisingly, RAB18 transcripts were not modified in ABA treated WT plants in our experiments although others authors have previously reported that this gene is up-regulated by ABA and drought (Lang et al., Plant Biol. 20:951-962 (1992)). RAB18 up-regulation was related with ADH1 and DREB1A induction and with drought tolerance (Kyu Hong et al., Planta 227: 539-558 (2008)). Furthermore, the induction of DREB1A resulted in the up-regulation of RD29A (Liu et al., Plant Cell tO:1391-1406 (1998)). On the other hand. MYB44 over-expressors were described as drought tolerant exhibiting a rapid stomata closure under stress conditions (salinity or drought). In HaHB11 plants RD29A, RD22 and RAB18 were repressed indicating a different pathway triggered in these plants resulting in enhanced tolerance to abiotic stresses.

CBF genes are well-known as involved in cold response as positive regulators and these genes are repressed in HaHB11 plants as well as other genes described as CBF downstream regulated genes (Yamaguchi-Shinozaki et al., Ann. Rev. Plant Biol. 57:781-803 (2006)). These genes were also repressed in HaHB11 plants. Altogether, these results suggest that HaHB11 may function in separate transcriptional regulation schemes. When induced by drought and salt stresses, HaHB11 functions as a positive regulator to aid ABA dependent up-regulation of stress responsive genes, leading to enhanced drought and salt tolerance, while when this gene is induced by cold stress it would act as a negative controller of an ABA independent pathway. This complex regulation mechanism is summarized in a putative model presented in FIG. 30.

Although not all drought tolerant plants are able to tolerate submergence, it appears that HaHB11 plants can tolerate this stress because they are prepared to survive under drought stress by stomata closing. Two different mechanisms in order to tolerate flooding have been described based on experimental data obtained with rice cultivars. One of them involves two AP2/ERF transcription factors named SNORKEL1 (SK1) and SK2 (Hattori et al., Ann. Rev. Plant Biol. 57:781-803 (2009)) and is essentially an escape response in which internode elongation is promoted in order to protrude above the surface of the water. The second one is a quiescent response in which elongation growth is restrained, economizing carbohydrate reserves in order to enable development of new leaves upon desubmergence. This mechanism is regulated by another AP2/ERF transcription factor, named submergence inducible gene (SUB1A; Xu et al., Nature 442(7103):705-708 (2006)). Since HaHB11 plants did not promote internode elongation under submergence stress, while better resisting this kind of stress, and capable of developing new healthy leaves after desubmergence, it appears that HaHB11 participates in the quiescent response.

Through the phenotypic, physiological and molecular analyses described above, positive correlations were found between HaHB11 over-expression, enhanced ABA sensitivity, reduced water loss rate, repression of genes involved in ABA biosynthesis and signaling, and induction of others encoding stress-protective proteins. These correlated changes caused by the HaHB11 transgene resulted in an improved tolerance to drought, high salinity stress, water-logging and submergence and, importantly, improved yield. Consequently, HaHB11 can be characterized as a positive regulator of the abiotic stress response.

Example 12

Experimental Procedures

Isolation and Molecular Characterization of Long Portion of HaHB11 Promoter

A long portion of the HaHB11 promoter was isolated from a genomic BAC (Id. 175N08—from Clemson University world wide web genome.clemson.edu). The Sunflower Library ID is HA_HBa and was generated from the ecotype HA383. Two oligonucleotides were designed to isolate 1363 bp of the HaHB11 promoter region which was cloned in the HindIII/XbaI sites of the pUC19 vector, the pBI 121 vector replacing the 35S promoter directing HaHB11 cDNA expression and in the pBI 101 vector directing GUS expression.

Figure 2A:
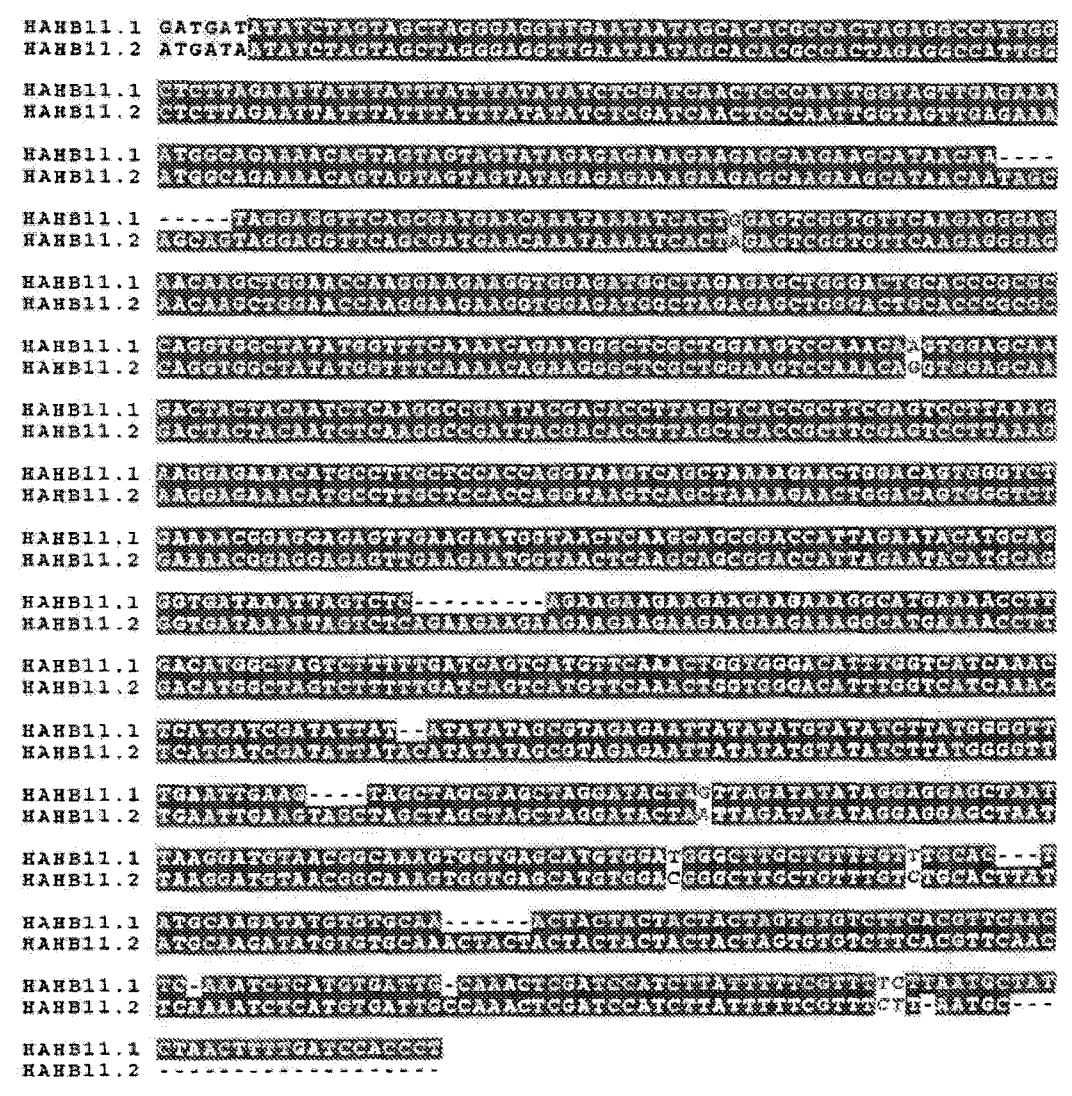

The sequence encoding HaHB11 from BAC 175N08 (HaHB11.1, SEQ. ID NO:2) was determined and compared with that isolated from clone RAFL (HaHB11.2, SEQ. ID NO:9). As depicted in FIGS. 2A and 2C, the sequences of these two *Helianthus* cultivars have differences that result in differences in the sequences of their respective encoded HaHB11 proteins (see, FIGS. 2A-B). The most significant differences between the sequences of these encoded HaHB11 proteins result in the insertions of three consecutive serines and three consecutive glutamic acids in different regions of the BAC 175N08 coding sequence.

Generation of Transgenic *Arabidopsis* Plants

ProH11 (Long)::H11.1

The HaHB11 long promoter isolated from BAC 175N08 ("ProH11"; SEQ ID NO:16) was inserted between HindIII and XbaI sites of the pBI121 binary vector, thereby replacing the constitutive 35S promoter and operably associating the ProH11 (long) promoter and HaHB11.1 coding sequence (SEQ ID NO:2). The resulting ProH11 (long)::H11.1 construct was transformed into *E. coli* and once confirmed, introduced into *Agrobacterium tummefaciens*. *Arabidopsis* plants, ecotype Col 0, were transformed following the floral dip method.

ProH11 (Long)::GUS

Following a strategy similar to that described above for the ProH11 (long)::H11.1 construct, the ProH11 long promoter was inserted in the HindIII/XbaI sites of the pBI 101 vector, thereby replacing the constitutive 35S promoter, and operably associating the ProH11 long promoter and GUS coding sequence.

35S::H11.2

The coding region from BAC 175N08 (HaHB11.2 (SEQ ID NO:10) was cloned in the BamH1/SacI sites of the pBI 121 vector, doing a chimerical construct in order to delete introns. In this way, the expression of the HaHB11.2 coding sequence was directed by the 35S constitutive promoter.

Activation Capacity Evaluated in Yeast Simple Hybrid

Both versions of the HaHB11 coding sequence (i.e., HaHB11.1 (SEQ ID NO:2) and HaHB11.2 (SEQ ID NO:10) were separately cloned in the pGBKT7 vector fused to the GAL4 DNA binding domain. Transactivation ability, as β-galactosidase activity quantitation, was tested for these constructs following a liquid culture assay using Ortho-Nitrophenyl-β-D-Galactopyranoside (ONPG) as substrate.

Soluble Sugars and Starch Quantitation

Leaf material (50-80 mg) was frozen in liquid $N_2$. Sucrose, glucose and starch were quantified in the soluble and residual fractions of ethanol-water extracts. Each sample was powdered in liquid $N_2$ and extracted in 700 µl of buffer containing 62.5% methanol, 26.8% chloroform, 5.4 mM $PO_4$ pH 7.5 and 0.1 mM EDTA. The extracts were kept on ice during 20 minutes and after an addition of 300 µl of water, they were vigorous mixed at room temperature and centrifuged for 5 min at 13000 rpm. Soluble sugars were quantified in the supernatant while starch in the pellet. The supernatant was decanted and evaporated at 40° C. using a speed vac. The pellet was resuspended in 100 µl of water And 50 µl were used to quantify glucose. The remaining 50 µl were incubated with 71 U of invertase (Roche) at 37° C. for 1 hour in order to measure glucose. Sucrose concentration was calculated from glucose determination. Glucose was tested using an enzymatic kit as follows: Glucose+$O_2$+$H_2O$→Gluconic acid+$H_2O_2$; $H_2O_2$+4-AF+4-hidroxibenzoat→red quinonimin. Red quinonimin was measured at 505 nm.

For starch extraction, the pellet was dried at 60° C. for an hour. Then, 250 µl of 0.1 N NaOH were added and the tubes were incubated 30 min at 70° C. The samples were neutralized with 75 µl of 0.1 N acetic acid and then centrifuged for 5 min at 13000 rpm. For starch cleavage we added a 50-µL aliquot of the supernatant to 8 µl of 50 mM sodium-acetate incubation buffer, pH 5.1, containing 28 units of amyloglucosidase (Roche). The samples were incubated at 37° C. for 16 h and then centrifuged for 5 min at 13000 rpm and glucose quantified in the supernatant.

Yield after Moderate Drought Stress

Moderate drought-stress treatments were carried out on plants grown under standard conditions until they reached a stem of 150 mm. Because of the development delay detected as this stage, WTs and TGs plants were subjected to drought stress starting at different times. In each case, watering was stopped until a moderate stress level was reached. Subsequently, the stress was maintained by watering the pots every day in order to maintain the same weight in all the pots. In this case, the field capacity is 150 g of water and soil and the permanent wilting point is 45 g. Moderate stress was set at 100 g of water and soil. The plants were watered up to 100 g until siliques were filled and they were ready to be harvested. Yield was informed as the seed weight for each plant.

Yield after Waterlogging

Plants were grown under normal conditions until reaching a stem length of approximately 200 mm. Because of the development delay, wild type plants and transgenic plants were subjected to stress starting at different times but at the same developmental stage. Plants were watered until the water level reached the soil limit. This stress was maintained for 3 days and then the plants were grown in standard conditions until siliques were filled and could be harvested. Yield was informed as the seed weight of each plant.

Example 13

Identification of HaHB11 Orthologs/Variants in the Asteraceae Family

Representative members of the Asteraceae family were screened for sequences encoding HaHB11 orthologs. FIG. 2C shows a sequence alignment of the HaHB11 orthologs and/or variants in the Asteraceae family identified by this screen. The alignment includes the sequence of HaHB11 orthologs in *Helianthus annuus* (Hann; SEQ ID NO:3 and SEQ ID NO:10), *Helianthus tuberosus*, (Htub; SEQ ID NO:3 and SEQ ID NO:11, SEQ ID NO:14 and SEQ ID NO:15), *Helianthus argophyllus* (Harg; SEQ ID NO:12) and *Helianthus ciliaris* (Hcil; SEQ ID NO:13). Table 1 provides an overview of domains in the identified HaHB11 orthologs/variants

TABLE 1

Structural domains of HaHB11 orthologs/variants in the Asteraceae family

| Asteraceae member | SEQ ID NO: | N-terminal region | HD-LZ region | HD region | LZ Region | C-terminal region |
|---|---|---|---|---|---|---|
| H. annuus HaHB11.1 | 3 | 1-14 | 15-110 | 15-74 | 75-110 | 111-175 |

TABLE 1-continued

Structural domains of HaHB11 orthologs/variants in the Asteraceae family

| Asteraceae member | SEQ ID NO: | N-terminal region | HD-LZ region | HD region | LZ Region | C-terminal region |
|---|---|---|---|---|---|---|
| H. annuus HaHB11.2 | 10 | 1-14 | 15-113 | 15-77 | 78-113 | 114-181 |
| H. tuberosus 1 | 11 | 1-14 | 15-113 | 15-77 | 78-113 | 114-180 |
| H. argophyllus | 12 | 1-14 | 15-110 | 15-74 | 75-110 | 111-179 |
| H. ciliaris | 13 | 1-14 | 15-110 | 15-74 | 75-110 | 111-177 |
| H. tuberosus 2 | 14 | 1-14 | 15-112 | 15-76 | 77-112 | 113-183 |
| H. tuberosus 3 | 15 | 1-14 | 15-111 | 15-75 | 76-111 | 112-186 |

Example 14

The HaHB11 Promoter Region Contains Stress Responsive Cis-Acting Elements

A 1364 bp fragment corresponding to the HaHB11 promoter region was isolated from BAC 175N08 as described above. This fragment of the promoter region exhibited cis-acting elements found in promoters that participate in abiotic stress responses. A LTRECOREATCOR15, core of low temperature responsive element (LTRE) is present at position 1158 of SEQ ID NO:16 (−strand); an ABRELAT-ERD1, ABRE (ABA-responsive element)-like sequence at position 1165 of SEQ ID NO:16 (−strand); two ABRERAT-CAL, ABRE-related sequence at positions 864 and 1164 of SEQ ID NO:16 (−strand); a DRE2COREZMRAB17, DRE (Dehydration responsive element) core found in Zea maize RAB17 gene promoter at position 1158 of SEQ ID NO:16 and an ANAERO2CONSENSUS, one of the 16 motifs found in silico in promoters of 13 anaerobic genes involved in the fermentative pathway, at position 243 bp SEQ ID NO:16 (−strand).

```
Sequence of HAHB11 proH11 long promoter portion
(1363 bp; SEQ ID NO: 16):
ccccaacaaaggtaaaagaaattttaataatggccgtgtaagacaaacc ctccagtcgttttcgtaaaagagttggggtgtctaaatttcattcatca cattcttttctttttcattatttatatttattttattcatcatgtca attagtttgacaaattaggcctagctagctaggtgtccaaaaccaaacg cataacattgcccacaaccatcaacttatgrtgacaattgtaaataagc tgctagctagcttgacatcaattatcaaaacacttgtctttgttaatcc aaaccatatatcttaaagccggtgtataagatgatcgattcgggaaat gaatcttgattatcatgatatctttacaggtggcaggaaagctagctag ctagctaaattcagtgtatcctccttacgattgagattattgaaattta tttattatgtgaagcaaatgtaatgcatgtgtgaaagcgtactattgga ggagccctatcccacatcgaacgaataagaccttccggttgtattaata agatcttgggttactccctctatcaccaattggttttagagtggaaccc catagacttcaatacgtacatccttcattttgtcctaattgaatttgt acttatcatagcatactttgacaaaaacatatacctggattaactacaa atgaacatgatcatctcacatatatatattaccttctctagcttttact atatatatatatatatatatatatatatatatattctcatttaagagaaca aatttaagtactatatattaattatagttgagcgttaaatccgtcacga gtcattattaaatccgtagatacaagtaccgcgtggaattggaaactca ttggatccttttggataaatagaaatattcccatcgatcataaacaatt aatatgagtatacataatgaaaactaaccttcaacaccgttgttaattc attttatacgccattccaagtatgcctaggcggtagagattgttgtctt tgaaggagaagatcgattaggattcaaatcctagcatggggtagattag catgaatatggtataactatgggtaggattaatgtaacattcgccgttg caaaaaaaaaaatcatttttatcgtcggtgcacgttttaaggttatta attaataacttgtaactaattgtaagcatcaacacatgttatgtcgtac cagatttttgtattattaattattagtctgctcatgtatatttaataat taataataatcggttaggcatattgtatccaagtgatatgaataaaatt agttgtggaaataagaaaaaggaaatatgatta
```

The ProH11 Long Promoter Fragment Directs GUS Expression in Roots, Hypocotyls and Petioles As described in the experimental procedures, the 1364 bp fragment corresponding to the HaHB11 promoter region was inserted upstream of the β-glucuronidase (GUS) reporter gene and the resulting expression cassette was transformed into Arabidopsis plants. GUS expression in the transgenic plants was evident in cotyledons (A), hypocotyls (B), petioles (C) and roots (D) in normal growth conditions (FIG. 33A-J: cotyledons (A), hypocotyls (B), petioles (C) and roots (D) in normal growth conditions).

The ProH11 Long Promoter is Inducible by ABA and Wounding

In view of the stress response associated cis acting elements detected in the HaHB11 promoter, a GUS expression pattern assay was conducted in transgenic Arabidopsis plants subjected to stress (i.e., ABA). As depicted in FIG. 33A-J, the location of the GUS expression in the transgenic plants bearing the ProH11 long . . . . GUS construct did not change after ABA treatment. However, the intensity of the signal significantly increased in all the tissues, indicating an up-regulation of this promoter by ABA in the cotyledons (A and F), hypocotyls (B and G), petioles (C and H) and roots (D-J).

ProH11 Long::H11 Transgenic Plants Exhibit Longer Roots

Transgenic Arabidopsis plants bearing the construct ProH11 long::H11 were grown in MS-agar plates and roots were observed 10 days after germination. As depicted in FIG. 34, transgenic plants exhibit significantly longer roots compared with WT plants and transgenic 35S::GUS control plants.

Example 15

Constitutive Expression of HAHB11 in Transgenic Plants

3S::H11.1 Transgenic Plants Exhibit Increased Yield after Waterlogging

While tolerance to a lethal stress has value as a biotechnological indicator, moderate stress conditions are more widespread in agriculture, and plants were therefore subjected to relatively moderate stress conditions in our study. HaHB11.1 and WT plants grown under normal conditions were given a regular watering regime or subjected to a moderate stress (waterlogging for 3 days). After that, plants were normally watered. This moderate stress treatment did not cause plant death; plants were able to flower and set seeds, so that yield could be quantified for each individual plant. FIG. 30 illustrates seed weight obtained for HaHB11 and WT plants subjected to a moderate waterlogging stress. Grown under standard conditions, HaHB11 plants exhibit approximately twice yield than WT plants. After the stress treatment, both genotypes showed a yield decrease but that of WT was significantly larger than that of transgenic plants.

3S::H11.1 Transgenic Plants Exhibit Increased Starch at the End of the Day

Figure 32A:
Figure 32B:
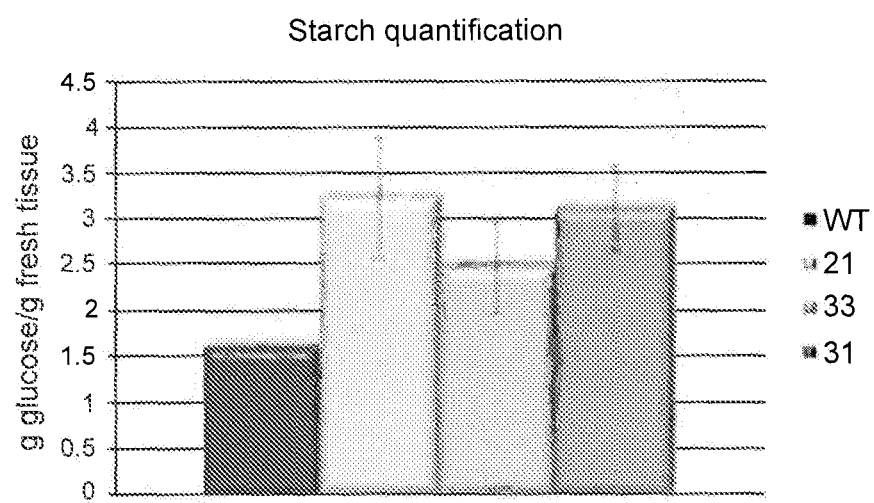

Rosettes from three-week-old transgenic 35S:HaHB11 and WT plants grown in standard conditions were analyzed for starch content. FIG. 32A shows a qualitative assay using a lugol staining technique. It can be appreciated that transgenic plants exhibit more starch than WT ones. FIG. 32B shows a quantitation of the accumulated starch during the day. This quantification was performed following the technique described in Strand et al., 1999 (Experimental procedures). Transgenic plants accumulated almost twice starch than WT.

Example 16

Transactivation of HAHB11.1 and HAHB11.2 in S. cerevisiae

Sacharomyces cerevisiae, strain Y187, were transformed with both constructs bearing the different clones of HaHB11 (HaHB11.1 and HaHB11.2). The activation assay was performed as described in the methods section. FIG. 35 indicates that HaHB11 acts as an activator, at least in the yeast system, and that both versions do not differ in this ability under the conditions tested.

The foregoing is illustrative of the present invention, and is not to be construed as limiting thereof. The invention is defined by the following claims, with equivalents of the claims to be included therein.

LITERATURE CITED

Arce A. L., Raineri J., Capella M., Cabello J. V. and Chan R. L. (2011) Uncharacterized conserved motifs outside the HD-Zip domain in HD-Zip subfamily I transcription factors; a potential source of functional diversity. BMC Plant Biol. 11:42.

Ariel F., Diet A., Verdenaud M., Gruber V., Frugier F., Chan R. and Crespi M. (2010) Environmental Regulation of Lateral Root Emergence in Medicago truncatula Requires the HD-Zip I Transcription Factor HB1. Plant Cell 22:2171-2183.

Ariel F. D., Manavella P. A., Dezar C. A. and Chan R. L. (2007) The true story of the HD-Zip family. Trends Plant Sci. 12:419-426.

Burrows W. J. and Carr D. J. (1969) Effects of flooding the root system of sunflower plants on the cytokinin content of the xylem sap. Plant Physiol. 22:1105-1112.

Cabello J. V., Arce A. L and Chan R. L. (2011) The homologous HD-Zip I transcription factors HaHB1 and AtHB13 confer cold tolerance via the induction of chitinase and glucanase proteins. Submitted Caries C., Bies-Etheve N., Aspart L., LeA on-Kloosterziel K. M., Koomneef M., Echeverria M. and Delseny M. (2002) Regulation of Arabidopsis thaliana Em Genes: Role of AB15. Plant J. 30:373-383.

Chan R. L., Gago G. M., Palena C. M. and Gonzalez D. H. (1998) Homeoboxes in plant development. Biochim. Biophys. Acta 1442:1-19.

Clough S. J. and Bent A. F. (1998). Floral dip: a simplified method for Agrobacterium-mediated transformation of Arabidopsis thaliana. Plant J. 16:735-743.

Dezar C. A., Fedrigo G. V. and Chan R. L. (2005b) The promoter of the sunflower HD-Zip protein gene Hahb4 directs tissue-specific expression and is inducible by water stress, high salt concentrations and ABA. Plant Sci. 169:447-459.

Dezar C. A., Gago G. M., Gonzalez D. H., and Chan R. L. (2005a) Hahb-4, a sunflower homeobox-leucine zipper gene, is a developmental regulator and confers drought tolerance to Arabidopsis thaliana plants. Transgenic Res. 14:429-440.

Easterling, WE (2007). Climate change and the adequacy of food and timber in the 21st century. PNAS. 104:19679

Ding 1, Li S., An X., Liu X., Qin H. and Wang D. (2009) Transgenic Expression of MYB15 Confers Enhanced Sensitivity to Abscisic Acid and Improved Drought Tolerance in Arabidopsis thaliana. J. Genet. Genom. 36:17-29

Drew M. C. and Sisworo E. J. (1977) Early effects of flooding on nitrogen deficiency and leaf chlorosis in barley. Nert J Phytol. 79:567-571.

Fukao T., Yeung E. and Railey-Serres J. (2011) The submergence tolerance regulator SUB 1A mediates crosstalk between submergence and drought tolerance in rice. Plant Cell 23:412-427.

Gago, G. M., Almoguera, C, Jordano, J., Gonzalez, D. H. and Chan, R. L. (2002) Hahb-4, a homeobox-leucine zipper gene potentially involved in abscisic acid-dependent responses to water stress in sunflower. Plant Cell Environ. 25, 633-640.

Hattori Y., Nagai K., Furukawa S., Song X. J., Kawano R., Sakakibara H., Wu J., Matsumoto T., Yoshimura A., Kitano H., Matsuoka M., Mori H. and Ashikari M. (2009). Nature 20:1026-1030.

Henriksson E., Olsson A. S. B., Johannesson H., Johansson H., Hanson J., Engstrom P. and Soderman E. (2005) Homeodomain Leucine Zipper Class I Genes in Arabidopsis. Expression Patterns and Phylogenetic Relationships. Plant Physiol. 139:509-518.

Hirayama T. and Shinozald K. (2007) Perception and Transduction of Abscisic Acid Signals:Keys to the Function of the Versatile Plant Hormone ABA. Trends Plant Sci. 12:343-351.

Jackson M. B. (1979) Rapid injury to peas by soil waterlogging. J. Sci. Food Agric. 30:143-152.

Jefferson, R. A., Kavanagh, T. A. and Bevan, M. W. (1987) GUS fusions:beta-glucuronidase as a sensitive and versatile gene fusion marker in higher plants. EMBO J. 6:3901-3907.

Kyu Hong J., Choi H. W., Hwang I. S., Kim D. S., Kim N. H., Choi D. S. Kim Y. J. and Hwang B. K. (2008) Function of a Novel GDSL-type Pepper Lipase Gene, CaGLIP1, in Disease Susceptibility and Abiotic Stress Tolerance. Planta 227:539-558.

Lang V. and Palva E. T. (1992) The Expression of a Rab-Related Gene, rab18, is Induced by Abscisic Acid During the Cold Acclimation Process of Arabidopsis thaliana. Plant Mol. Biol. 20:951-962.

Liu Q., Kasuga M., Sakuma Y., Abe H., Miura S., Yamaguchi-Shinozaki K. and Shinozaki K. (1998) Two Transcription Factors, DREB1 and DREB2, with an EREBP/AP2 DNA Binding Domain Separate two Cellular Signal Transduction Pathways in Drought- and Low-Temperature-Responsive Gene Expression, respectively, in *Arabidopsis*. Plant Cell 10:1391-1406.

Lopez-Molina L., Mongrand S. and Chua N. H. (2001) A Postgermination Developmental Arrest Checkpoint is Mediated by Abscisic Acid and Requires the AB15 Transcription Factor in *Arabidopsis*. PNAS 98:4782-4787.

Manfre A. J., Lanni L. M. and Marcotte W. R. (2006). The *Arabidopsis* Group 1 LATE EMBRYOGENESIS ABUNDANT Protein ATEM6 Is Required for Normal Seed Development. Plant Physiol. 140:140-149, Manavella, P. A., Arce, Al., Dezar, C. A., Bitton, F., Reuou, Crespi, M., and Chan, R. L. (2006) Cross-talk between ethylene and drought signaling pathways is mediated by the sunflower Hahb-4 transcription factor. Plant. J. 48:125-137.

Manavella, P. A., and Chan, R. L. (2009) Transient transformation of sunflower leaf discs via an *Agrobacterium*-mediated method: applications for gene expression and silencing studies. Nat. Protoc. 4:1699-1707.

Manavella P. A., Dezar C. A., Ariel F. D., Drincovich M. F. and Chan R. L. (2008b) The sunflower HD-Zip transcription factor HAHB4 is up regulated in darkness acting as a repressor of photosynthesis related genes transcription. J Exp. Bot. 59:3143-3155.

Manavella P. A., Dezar C. A., Bonaventm•e G., Baldwin I. T. and Chan, R. L. (2008a) HAHB4, a sunflower HD-Zip protein, integrates signals from the jasmonic acid and ethylene pathways during wounding and biotic stress responses, Plant J. 56:376-388.

Manavella P A, Ariel F D, Dezar C A, Chan R L (2008c) "Two ABREs, two redundant root-specific and one W-box cis-acting elements are functional in the sunflower HAHB4 promoter" Plant Physiol. Biochem. 46:860-867.

Mitsuda N. and Ohme-Tagaki M. (2009) Functional Analysis of Transcription Factors in *Arabidopsis*. Plant and Cell Physiology. 50:1232-1248.

Nakashima K. and Yamaguchi-Shinozaki K. (2005) Molecular Studies on Stress-Responsive Gene Expression in *Arabidopsis* and improvement of Stress Tolerance in Crop Plants by Regulon Biotechnology. Japan Agricultural Research Quarterly. 39:221-22.9.

Olsson A. S., Engstrom P. and Soderman E. (2004) The Homeobox Genes Athbl2 and Athb7 Encode Potential Regulators of Growth in Response to Water Deficit in *Arabidopsis*. Plant Mol. Biol. 55:663-677.

Olymbios C. M. and Schwabe W. W. (1977) Effects of aeration and soil compaction on growth of the carrot, *Daucus carota* L. J. Am. Soc. Hort. Sci. 52:485-500.

Raghavendra A. S., Gonugunta V. K., Christmann A. and Grill E. (2010) ABA Perception and Signalling. Cell 15:395-401.

Riechmann J. L., Heard J., Martin G., Reuber L., Jiang C., Keddie J., Adam L., Pineda O., Ratcliffe O. J., Samaha R. R., Creelman R., Pilgrim M., Broun P., Zhang J. Z., Ghandehari D., Sherman B. K. and Yu G. (2000) *Arabidopsis* Transcription Factors:Genome-Wide Comparative Analysis among Eukaryotes. Science 290:2105-2110.

Schena, M. and Davis, R. W. (1992) HD-Zip protein members of *Arabidopsis* homeodomain protein superfamily. Proc. Natl Acad. Sci. USA, 89, 3894-3898.

Shin D, Koo Y D, Lee J, Lee H J, Baek D, Lee S, Cheon Cl, Kwak S S, Lee S Y, Yun D J. (2004) Athb-12, a homeobox-leucine zipper domain protein from *Arabidopsis thaliana*, increases salt tolerance in yeast by regulating sodium exclusion. Biochem. Biophys. Res. Commun. 323:534-40.

Sullivan M., VanToai T., Fausey N., Beuerlein J., Parkinson R. and Soboyejo A. (2001) Evaluating on-farm flooding impacts on soybean. Crop Sci. 41:1-8.

Thomashow M. F. (2001). So what's New in the Field of Plant Cold Acclimation? Lots! Plant Physiol. 125:89-93.

Trought M. C. T. and Drew M. C. (1980) The development of waterlogging damage in wheat seedlings (*Triticum aestivum* L.). I. Shoot and root growth in relation to changes in the concentrations of dissolved gases and solutes in the soil solution. Plant Soil 54:77-94.

VanToai T. T., Beuerlein .J. E., Schmitthenner A. F. and St Marttin K. S. (1994) Genetic variability for flooding tolerance in soybeans. Crop Sci. 34:1112-1115.

Visser E. J. W, Voesenek: L. A. C. J., Vartapetian B. B. and Jackson M. B. (2003). Flooding and Plant Growth. Ann. Bot. 91: 107-109.

Whatley F. R., Tagawa K. and Arnon D. I. (1963) Separation of the Light and Dark Reactions in Electron Transfer during Photosynthesis. Proc. Natl Acad. Sci. USA 49: 266-270.

Xu K., Xu X., Fukao T., Canlas P., Maghirang-Rodriguez R., Heuer S., Ismail A. M., Bailey-Serres J., Ronald F. C. and Mackill D. J. (2006) SublA is an ethylene-response-factor-like gene that confers submergence tolerance to rice. Nature 10: 705-708.

Yamaguchi-Shinozaki K. and Shinozaki K. (1994) A Novel cis-Acting Element in an *Arabidopsis* Gene is Involved in Responsiveness to Drought, Low-Temperature, or High Salt Stress. Plant Cell 6: 251-264.

Yamaguchi-Shinozaki K. and Shinozaki K. (2006) Transcriptional Regulatory Networks in Cellular Responses and Tolerance to Dehydration and Cold Stresses. Ann. Rev. Plant Biol. 57:781-803.

Zou X., Jiang Y., Liu L., Zhang Z. and Zheng Y. (2010) Identification of transcriptome induced in roots of maize seedlings at the late stage of waterlogging. BMC Plant Biol. 10:189-215.

The contents of U.S. Application No. 61/594,133; filed Feb. 2, 2012, is herein incorporated by reference in its entirety. Additionally, all publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A transgenic plant stably transformed with an isolated nucleic acid encoding a polypeptide comprising the amino acid sequence of SEQ ID NO:10 operably associated with a promoter, wherein the promoter is heterologous to the coding sequence.

2. The transgenic plant of claim 1, wherein the nucleic acid sequence comprises the nucleotide sequence of SEQ ID NO:9.

3. The transgenic plant of claim 1, wherein the transgenic plant is stably transformed with an expression cassette.

4. The transgenic plant of claim 3, wherein the expression cassette comprises a selectable marker.

5. The plant of claim 1, wherein the plant is (a) a monocot, (b) a dicot or (c) a sunflower, wheat, maize, soybean, rice, alfalfa or *Arabidopsis*.

6. A crop comprising a plurality of the plant of claim 1.

7. Seed produced from the transgenic plant of claim 1, wherein the seed comprises the isolated nucleic acid stably incorporated in its genome.

* * * * *

SEQUENCE LISTING

```
<160> NUMBER OF SEQ ID NOS: 17

<210> SEQ ID NO 1
<211> LENGTH: 944
<212> TYPE: DNA
```

<213> ORGANISM: Helianthus annuus

<400> SEQUENCE: 1

| | | | | | |
|---|---|---|---|---|---|
| gatgatatat | ctagtagcta | gggaggttga | ataatagcac | acgccactag | aggccattgg | 60 |
| ctcttagaat | tatttattta | tttatatatc | tcgatcaact | cccaattggt | agttgagaaa | 120 |
| atggcagaaa | acagtagtag | tagtatagag | agaaagaaga | gcaagaagca | taacaatagg | 180 |
| aggttcagcg | atgaacaaat | aaaatcactg | gagtcggtgt | tcaagaggga | gaacaagctg | 240 |
| gaaccaagga | agaaggtgga | gatggctaga | gagctgggac | tgcacccgcg | ccaggtggct | 300 |
| atatggtttc | aaaacagaag | ggctcgctgg | aagtccaaac | aagtggagca | agactactac | 360 |
| aatctcaagg | ccgattacga | caccttagct | caccgcttcg | agtccttaaa | gaaggagaaa | 420 |
| catgccttgc | tccaccaggt | aagtcagcta | aaagaactgg | acagtgggtc | tgaaaacgga | 480 |
| ggagagttga | agaatggtaa | ctcaagcagc | ggaccattag | aatacatgca | gggtgataaa | 540 |
| ttagtctcag | aagaagaaga | agaagaaagg | catgaaaacc | ttgacatggc | tagtcttttt | 600 |
| gatcagtcat | gttcaaactg | gtgggacatt | tggtcatcaa | actcatgatc | gatattatat | 660 |
| atatagcgta | gagaattata | tatgtatatc | ttatggggtt | tgaattgaag | tagctagcta | 720 |
| gctaggatac | tagttagata | tataggagga | gctaattaag | gatgtaacgg | caaagtggtg | 780 |
| agcatgtgga | tgggcttgct | gtttgtttgc | actatgcaag | atatgtgtgc | aaactactac | 840 |
| tactactagt | gtgtcttcac | gttcaactca | aatctcatgt | gattgcaaac | tcgatccatc | 900 |
| ttatttttcg | ttttcttaat | gctatctaac | ttttgatcca | ccct | | 944 |

<210> SEQ ID NO 2
<211> LENGTH: 528
<212> TYPE: DNA
<213> ORGANISM: Helianthus annuus

<400> SEQUENCE: 2

| | | | | | |
|---|---|---|---|---|---|
| atggcagaaa | acagtagtag | tagtatagag | agaaagaaga | gcaagaagca | taacaatagg | 60 |
| aggttcagcg | atgaacaaat | aaaatcactg | gagtcggtgt | tcaagaggga | gaacaagctg | 120 |
| gaaccaagga | agaaggtgga | gatggctaga | gagctgggac | tgcacccgcg | ccaggtggct | 180 |
| atatggtttc | aaaacagaag | ggctcgctgg | aagtccaaac | aagtggagca | agactactac | 240 |
| aatctcaagg | ccgattacga | caccttagct | caccgcttcg | agtccttaaa | gaaggagaaa | 300 |
| catgccttgc | tccaccaggt | aagtcagcta | aaagaactgg | acagtgggtc | tgaaaacgga | 360 |
| ggagagttga | agaatggtaa | ctcaagcagc | ggaccattag | aatacatgca | gggtgataaa | 420 |
| ttagtctcag | aagaagaaga | agaagaaagg | catgaaaacc | ttgacatggc | tagtcttttt | 480 |
| gatcagtcat | gttcaaactg | gtgggacatt | tggtcatcaa | actcatga | | 528 |

<210> SEQ ID NO 3
<211> LENGTH: 175
<212> TYPE: PRT
<213> ORGANISM: Helianthus annuus

<400> SEQUENCE: 3

Met Ala Glu Asn Ser Ser Ser Ser Ile Glu Arg Lys Lys Ser Lys Lys
1               5                   10                  15

His Asn Asn Arg Arg Phe Ser Asp Glu Gln Ile Lys Ser Leu Glu Ser
            20                  25                  30

Val Phe Lys Arg Glu Asn Lys Leu Glu Pro Arg Lys Lys Val Glu Met
        35                  40                  45

```
Ala Arg Glu Leu Gly Leu His Pro Arg Gln Val Ala Ile Trp Phe Gln
 50                  55                  60

Asn Arg Arg Ala Arg Trp Lys Ser Lys Gln Val Glu Gln Asp Tyr Tyr
 65                  70                  75                  80

Asn Leu Lys Ala Asp Tyr Asp Thr Leu Ala His Arg Phe Glu Ser Leu
                 85                  90                  95

Lys Lys Glu Lys His Ala Leu Leu His Gln Val Ser Gln Leu Lys Glu
            100                 105                 110

Leu Asp Ser Gly Ser Glu Asn Gly Gly Glu Leu Lys Asn Gly Asn Ser
            115                 120                 125

Ser Ser Gly Pro Leu Glu Tyr Met Gln Gly Asp Lys Leu Val Ser Glu
        130                 135                 140

Glu Glu Glu Glu Glu Arg His Glu Asn Leu Asp Met Ala Ser Leu Phe
145                 150                 155                 160

Asp Gln Ser Cys Ser Asn Trp Trp Asp Ile Trp Ser Ser Asn Ser
                165                 170                 175

<210> SEQ ID NO 4
<211> LENGTH: 839
<212> TYPE: DNA
<213> ORGANISM: Helianthus annuus

<400> SEQUENCE: 4
aaaatagaaa tattcccatc gatcataaac aattaatatg agtatacata atgaaaacta      60
accttcaaca ccgttgttaa ttcattttat acgccattcc aagtatgcct aggcggtaga     120
gattgttgtc tttgaaggag aagatcgatt aggattcaaa tcctagcatg ggtagatta     180 gcatgaatat ggtataacta tgggtaggat taatgtaaca ttcgccgttg caaaaaaaaa     240
aaaaaaatca tttttatcgt cggtgcacgt tttaaggtta ttaattaata acttgtaact     300
aattgtaagc atcaacacat gttatgtcgt accagatttt tgtattatta attattagtc     360
tgctcatgta tatttaataa ttaataataa tcggttaggc atattgtctt ccaagtgata     420
tgaataaaat tagttgtgga aataagaaaa aggaaatatg attaatgata atatctagta     480
gctagggagg ttgaataata gcacacgcca ctagaggcca ttggctctta gaattattta     540
tttatttata tatctcgatc aactcccaat tggtagttga gaaaatggca gaaaacagta     600
gtagtagtat agagagaaag aagagcaaga agcataacaa tagcagcagt aggaggttca     660
gcgatgaaca aataaaatca ctagagtcgg tgttcaagag ggagaacaag ctggaaccaa     720
ggaagaaggt ggagatggct agagagctgg gactgcaccc gcgccaggtg gctatatggt     780
ttcaaaacag aagggctcgc tgaagtccaa acaggggagc agactctcat tcatgctttt    839

<210> SEQ ID NO 5
<211> LENGTH: 416
<212> TYPE: DNA
<213> ORGANISM: Helianthus annuus

<400> SEQUENCE: 5
aaaatagaaa tattcccatc gatcataaac aattaatatg agtatacata atgaaaacta      60
accttcaaca ccgttgttaa ttcattttat acgccattcc aagtatgcct aggcggtaga     120
gattgttgtc tttgaaggag aagatcgatt aggattcaaa tcctagcatg ggtagatta     180 gcatgaatat ggtataacta tgggtaggat taatgtaaca ttcgccgttg caaaaaaaaa     240
aaaaaaatca tttttatcgt cggtgcacgt tttaaggtta ttaattaata acttgtaact     300
aattgtaagc atcaacacat gttatgtcgt accagatttt tgtattatta attattagtc     360
```

```
tgctcatgta tatttaataa ttaataataa tcggttaggc atattgtctt ccaagt         416
```

```
<210> SEQ ID NO 6
<211> LENGTH: 584
<212> TYPE: DNA
<213> ORGANISM: Helianthus annuus

<400> SEQUENCE: 6
aaaatagaaa tattcccatc gatcataaac aattaatatg agtatacata atgaaaacta     60
accttcaaca ccgttgttaa ttcattttat acgccattcc aagtatgcct aggcggtaga    120
gattgttgtc tttgaaggag aagatcgatt aggattcaaa tcctagcatg ggtagatta    180 gcatgaatat ggtataacta tgggtaggat taatgtaaca ttcgccgttg caaaaaaaaa    240
aaaaaaatca ttttatcgt cggtgcacgt tttaaggtta ttaattaata acttgtaact     300
aattgtaagc atcaacacat gttatgtcgt accagatttt tgtattatta attattagtc    360
tgctcatgta tatttaataa ttaataataa tcggttaggc atattgtctt ccaagtgata    420
tgaataaaat tagttgtgga aataagaaaa aggaaatatg attaatgata atatctagta    480
gctagggagg ttgaataata gcacacgcca ctagaggcca ttggctctta gaattattta    540
tttatttata tatctcgatc aactcccaat tggtagttga gaaa                     584
```

```
<210> SEQ ID NO 7
<211> LENGTH: 9
<212> TYPE: DNA
<213> ORGANISM: Artificial Sequence
<220> FEATURE:
<223> OTHER INFORMATION: HD-Zip domain

<400> SEQUENCE: 7 caatwattg                                                             9
```

```
<210> SEQ ID NO 8
<211> LENGTH: 956
<212> TYPE: DNA
<213> ORGANISM: Helianthus annuus

<400> SEQUENCE: 8
atgataatat ctagtagcta gggaggttga ataatagcac acgccactag aggccattgg     60
ctcttagaat tatttattta tttatatatc tcgatcaact cccaattggt agttgagaaa    120
atggcagaaa acagtagtag tagtatagag agaaagaaga gcaagaagca taacaatagc    180
agcagtagga ggttcagcga tgaacaaata aaatcactag agtcggtgtt caagagggag    240
aacaagctgg aaccaaggaa gaaggtggag atggctagag agctgggact gcacccgcgc    300
caggtggcta tatggtttca aaacagaagg gctcgctgga agtccaaaca ggtggagcaa    360
gactactaca atctcaaggc cgattacgac accttagctc accgcttcga gtccttaaag    420
aaggagaaac atgccttgct ccaccaggta agtcagctaa agaactggac agtgggtct    480 gaaaacggag gagagttgaa gaatggtaac tcaagcagcg gaccattaga atacatgcag    540
ggtgataaat tagtctcaga agaagaagaa gaagaagaag aagaaaggca tgaaaacctt    600
gacatggcta gtcttttga tcagtcatgt tcaaactggt gggacatttg gtcatcaaac    660
tcatgatcga tattatacat atatagcgta gagaattata tatgtatatc ttatggggtt    720
tgaattgaag tagctagcta gctagctagg atactaatta gatatatagg aggagctaat    780
taaggatgta acggcaaagt ggtgagcatg tggacgggct tgctgtttgt ctgcacttat    840
```
atgcaagata tgtgtgcaaa ctactactac tactactact agtgtgtctt cacgttcaac    900
tcaaaatctc atgtgattgc caaactcgat ccatcttatt tttcgtttct taatgc        956

<210> SEQ ID NO 9
<211> LENGTH: 546
<212> TYPE: DNA
<213> ORGANISM: Helianthus annuus

<400> SEQUENCE: 9
atggcagaaa acagtagtag tagtatagag agaaagaaga gcaagaagca taacaatagc     60
agcagtagga ggttcagcga tgaacaaata aaatcactag agtcggtgtt caagagggag    120
aacaagctgg aaccaaggaa gaaggtggag atggctagag agctgggact gcacccgcgc    180
caggtggcta tatggtttca aaacagaagg gctcgctgga agtccaaaca ggtggagcaa    240
gactactaca atctcaaggc cgattacgac accttagctc accgcttcga gtccttaaag    300
aaggagaaac atgccttgct ccaccaggta agtcagctaa agaactgga cagtgggtct     360 gaaaacggag gagagttgaa gaatggtaac tcaagcagcg gaccattaga atacatgcag    420
ggtgataaat tagtctcaga agaagaagaa gaagaagaag aagaaaggca tgaaaacctt    480
gacatggcta gtctttttga tcagtcatgt tcaaactggt gggacatttg gtcatcaaac    540
tcatga                                                                546

<210> SEQ ID NO 10
<211> LENGTH: 181
<212> TYPE: PRT
<213> ORGANISM: Helianthus annuus

<400> SEQUENCE: 10

Met Ala Glu Asn Ser Ser Ser Ser Ile Glu Arg Lys Lys Ser Lys Lys
1               5                   10                  15

His Asn Asn Ser Ser Ser Arg Arg Phe Ser Asp Glu Gln Ile Lys Ser
            20                  25                  30

Leu Glu Ser Val Phe Lys Arg Glu Asn Lys Leu Glu Pro Arg Lys Lys
        35                  40                  45

Val Glu Met Ala Arg Glu Leu Gly Leu His Pro Arg Gln Val Ala Ile
    50                  55                  60

Trp Phe Gln Asn Arg Arg Ala Arg Trp Lys Ser Lys Gln Val Glu Gln
65                  70                  75                  80

Asp Tyr Tyr Asn Leu Lys Ala Asp Tyr Asp Thr Leu Ala His Arg Phe
                85                  90                  95

Glu Ser Leu Lys Lys Glu Lys His Ala Leu Leu His Gln Val Ser Gln
            100                 105                 110

Leu Lys Glu Leu Asp Ser Gly Ser Glu Asn Gly Gly Glu Leu Lys Asn
        115                 120                 125

Gly Asn Ser Ser Ser Gly Pro Leu Glu Tyr Met Gln Gly Asp Lys Leu
    130                 135                 140

Val Ser Glu Glu Glu Glu Glu Glu Glu Arg His Glu Asn Leu
145                 150                 155                 160

Asp Met Ala Ser Leu Phe Asp Gln Ser Cys Ser Asn Trp Trp Asp Ile
                165                 170                 175

Trp Ser Ser Asn Ser
            180

<210> SEQ ID NO 11
<211> LENGTH: 180

```
<212> TYPE: PRT
<213> ORGANISM: Helianthus tuberosus 1

<400> SEQUENCE: 11

Met Ala Glu Asn Ser Ser Ser Ile Glu Arg Lys Ser Lys Lys
1               5                   10                  15

His Asn Asn Ser Ser Ser Arg Arg Phe Ser Asp Glu Gln Ile Lys Ser
                20                  25                  30

Leu Glu Ser Val Phe Lys Arg Glu Asn Lys Leu Glu Pro Arg Lys Lys
            35                  40                  45

Val Glu Met Ala Arg Glu Leu Gly Leu His Pro Arg Gln Val Ala Ile
50                  55                  60

Trp Phe Gln Asn Arg Arg Ala Arg Trp Lys Ser Lys Gln Val Glu Gln
65                  70                  75                  80

Asp Tyr Tyr Asn Leu Lys Ala Asp Tyr Asp Thr Leu Thr His Arg Phe
                85                  90                  95

Glu Ser Leu Lys Lys Glu Lys His Ala Leu Leu His Gln Val Ser Gln
            100                 105                 110

Leu Lys Glu Leu Asp Ser Gly Ser Glu Asn Gly Gly Glu Leu Lys Asn
        115                 120                 125

Gly Asn Ser Ile Ser Gly Pro Leu Glu Tyr Met Gln Gly Asp Lys Leu
130                 135                 140

Val Ser Glu Glu Glu Glu Glu Glu Arg His Glu Asn Leu Asp
145                 150                 155                 160

Leu Ala Ser Leu Phe Asp Gln Ser Cys Ser Asn Trp Trp Asp Ile Trp
                165                 170                 175

Ser Ser Asn Ser
            180

<210> SEQ ID NO 12
<211> LENGTH: 179
<212> TYPE: PRT
<213> ORGANISM: Helianthus argophyllus

<400> SEQUENCE: 12

Met Ala Glu Asn Ser Ser Ser Met Glu Arg Lys Lys Ser Lys Lys
1               5                   10                  15

His Asn Asn Arg Arg Phe Ser Asp Glu Gln Ile Lys Ser Leu Glu Ser
                20                  25                  30

Val Phe Lys Arg Glu Asn Lys Leu Glu Pro Arg Lys Lys Val Glu Met
            35                  40                  45

Ala Arg Glu Leu Gly Leu His Pro Arg Gln Val Ala Ile Trp Phe Gln
50                  55                  60

Asn Arg Arg Ala Arg Trp Lys Ser Lys Gln Val Glu Gln Asp Tyr Tyr
65                  70                  75                  80

Asn Leu Lys Ala Asp Tyr Asp Thr Leu Ala His Arg Phe Glu Ser Leu
                85                  90                  95

Lys Lys Glu Lys His Ala Leu Leu His Gln Val Ser Gln Leu Lys Glu
            100                 105                 110

Leu Asp Ser Gly Ser Glu Asn Gly Gly Gly Glu Leu Lys Asn Gly Asn
        115                 120                 125

Ser Ser Ser Gly Pro Leu Glu Tyr Met Gln Gly Asp Lys Leu Val Ser
130                 135                 140

Glu Glu Glu Glu Glu Glu Glu Glu Arg His Glu Asn Leu Asp Met
145                 150                 155                 160
```

```
                Ala Ser Leu Phe Asp Gln Ser Cys Ser Asn Trp Trp Asp Ile Trp Ser
                                165                 170                 175

Ser Asn Ser

<210> SEQ ID NO 13
<211> LENGTH: 177
<212> TYPE: PRT
<213> ORGANISM: Helianthus ciliaris

<400> SEQUENCE: 13

Met Ala Glu Asn Ser Ser Ser Ile Glu Arg Lys Lys Ser Lys Lys
1               5                   10                  15

His Asn Asn Arg Arg Phe Ser Asp Glu Gln Ile Lys Ser Leu Glu Ser
            20                  25                  30

Val Phe Glu Arg Glu Asn Lys Leu Glu Pro Arg Lys Val Glu Met
        35                  40                  45

Ala Arg Glu Leu Gly Leu His Pro Arg Gln Val Ala Ile Trp Phe Gln
50                  55                  60

Asn Arg Arg Ala Arg Trp Lys Ser Lys Gln Val Glu Gln Asp Tyr Tyr
65                  70                  75                  80

Asn Leu Lys Ala Asp Tyr Asp Thr Leu Ala His Arg Phe Glu Ser Leu
                85                  90                  95

Lys Lys Glu Lys His Ala Leu Leu His Gln Val Ser Gln Leu Lys Glu
            100                 105                 110

Leu Asp Ser Gly Ser Glu Asn Gly Gly Gly Glu Leu Lys Asn Gly Lys
        115                 120                 125

Ser Ser Ser Gly Pro Leu Glu Tyr Met Gln Gly Asp Lys Leu Val Ser
    130                 135                 140

Glu Glu Glu Glu Glu Glu Arg Arg Glu Asn Leu Asp Leu Ala Ser
145                 150                 155                 160

Leu Phe Asp Gln Ser Cys Ser Asn Trp Trp Asp Ile Trp Ser Ser Asn
                165                 170                 175

Ser

<210> SEQ ID NO 14
<211> LENGTH: 183
<212> TYPE: PRT
<213> ORGANISM: Helianthus tuberosus 2

<400> SEQUENCE: 14

Leu Arg Arg Gly Arg Asn Val Val Arg Glu Glu Asp Lys Lys His
1               5                   10                  15

Asn Asn Ser Ser Ser Arg Arg Phe Ser Asp Glu Gln Ile Lys Ser Leu
            20                  25                  30

Glu Ser Val Phe Lys Arg Glu Asn Lys Leu Glu Pro Arg Lys Val
        35                  40                  45

Glu Met Ala Arg Glu Leu Gly Leu His Pro Arg Gln Val Ala Ile Trp
    50                  55                  60

Phe Gln Asn Arg Arg Ala Arg Trp Lys Ser Lys Gln Val Glu Gln Asp
65                  70                  75                  80

Tyr Ser Asn Leu Lys Ala Asp Tyr Asp Thr Leu Ala Gln Arg Phe Glu
                85                  90                  95

Ser Leu Lys Lys Glu Lys His Ala Leu Leu His Gln Val Ser Gln Leu
            100                 105                 110

Lys Glu Leu Asp Ser Gly Ser Glu Asn Gly Gly Gly Glu Leu Lys Asn
        115                 120                 125
```

Gly Asn Ser Ser Ser Gly Pro Leu Asp Met Ala Ile Tyr Ser Asp Glu
              130                 135                 140

Tyr Met Gln Gly Asp Lys Leu Val Ser Glu Glu Glu Glu Arg His Glu
145                 150                 155                 160

Asn Leu Asp Met Ala Ser Leu Phe Asp Gln Ser Cys Ser Asn Trp Trp
                165                 170                 175

Asp Ile Trp Ser Ser Asn Ser
                180

<210> SEQ ID NO 15
<211> LENGTH: 186
<212> TYPE: PRT
<213> ORGANISM: Helianthus tuberosus 3

<400> SEQUENCE: 15

Arg Gly Ala Glu Arg Ser Ile Glu Arg Lys Lys Ser Lys Lys His Asn
1               5                   10                  15

Asn Ser Ser Arg Arg Phe Ser Asp Glu Gln Ile Lys Ser Leu Glu
            20                  25                  30

Ser Val Phe Lys Arg Glu Asn Lys Leu Glu Pro Arg Lys Lys Val Glu
            35                  40                  45

Met Ala Arg Glu Leu Gly Leu His Pro Arg Gln Val Ala Ile Trp Phe
        50                  55                  60

Gln Asn Arg Arg Ala Arg Trp Lys Ser Lys Gln Val Glu Gln Asp Tyr
65                  70                  75                  80

Ser Asn Leu Lys Ala Asp Tyr Asp Ser Leu Ala Gln Arg Phe Glu Ser
                85                  90                  95

Leu Lys Lys Glu Lys His Ala Leu Leu His Gln Val Ser Gln Leu Lys
            100                 105                 110

Glu Leu Asp Ser Gly Ser Glu Asn Gly Gly Gly Glu Leu Lys Asn Gly
        115                 120                 125

Asn Ser Ser Ser Gly Pro Leu Asp Met Ala Ile Tyr Ser Asp Glu Tyr
    130                 135                 140

Met Gln Gly Asp Lys Leu Val Ser Glu Glu Glu Glu Glu Glu Glu Glu
145                 150                 155                 160

Arg His Glu Asn Leu Asp Met Ala Ser Leu Phe Asp Gln Ser Cys Ser
                165                 170                 175

Asn Trp Trp Asp Leu Trp Ser Ser Asn Ser
            180                 185

<210> SEQ ID NO 16
<211> LENGTH: 1362
<212> TYPE: DNA
<213> ORGANISM: Helianthus annuus

<400> SEQUENCE: 16
ccccaacaaa ggtaaaagaa atttttaataa tggccgtgta agacaaaccc tccagtcgtt     60
ttcgtaaaag agttggggtg tctaaatttc attcatcacc tttctttttc ttttcatta    120 tttatattta tttttattca tcatgtcaat tttgtttgac aaattaggcc tagctagcta    180
ggtgtccaaa accaaacgca taacattgcc cacaaccatc aacttatgtt gacaattgta    240
aataagctgc tagctagctt gttcatcaat tatcaaaaca cttgtctttg ttaatccaaa    300
ccatatatct taaagccggt gtataagatg atcgattcgg ggaaatgaat cttgattatc    360
atgatatctt tacaggtggc aggaaagcta gctagctagc taaattcagt gtcttcctcc    420

```
ttacgattga gattattgaa atttatttat tatgtgaagc aaatgtaatg catgtgtgaa      480
agcgtactat tggaggagcc ctatcccaca tcgaacgaat aagaccttcc ggttgtatta      540
ataagatctt gggttactcc ctctatcacc aattggtttt agagtggaac cccatagact      600
tcaatacgta catccttcat tttgtccta attgaatttg tacttatcat agcatacttt       660
gacaaaaaca tatacctgga ttaactacaa atgaacatga tcatctcaca tatatatatt     720
accttctcta gcttttacta tatatatata tatatatata tatatatata ttctcattta      780
agagaacaaa tttaagtact atatattaat tatagttgag cgttaaatcc gtcacgagtc      840
attctttaaa tccgtagata caagtaccgc gtggaattgg aaactcattg gatccttttg      900
gataaataga aatattccca tcgatcataa acaattaata tgagtataca taatgaaaac     960
taaccttcaa caccgttgtt aattcatttt atacgccatt ccaagtatgc ctaggcggta     1020
gagattgttg tctttgaagg agaagatcga ttaggattca aatcctagca tggggtagat     1080
tagcatgaat atggtataac tatgggtagg attaatgtaa cattcgccgt tgcaaaaaaa     1140
aaaaatcatt tttatcgtcg gtgcacgttt taaggttatt aattaataac ttgtaactaa     1200
ttgtaagcat caacacatgt tatgtcgtac cagattttg tattattaat tattagtctg       1260
ctcatgtata tttaataatt aataataatc ggttaggcat attgtcttcc aagtgatatg     1320
aataaaatta gttgtggaaa taagaaaaag gaaatatgat ta                         1362

<210> SEQ ID NO 17
<211> LENGTH: 677
<212> TYPE: DNA
<213> ORGANISM: Arabidopsis thaliana

<400> SEQUENCE: 17
gtaaatcccc agactcatct ctctctctcc ttttcttttg atttctagat ttgctagttt       60
gtttcgattg ttcttctaga tagaaattaa cgagtgattt ttgatttaac cgattcgcat      120 caatgccct tcttcttatt gcgtcgatct catggatcgg gatccatcgt tcctctatct       180
gatttctctt gtgggaaaga atttcaagct ttatggtttt gtagtaatga acgtttatca      240
ttttcgttcg agggaagatt tttaaacttt cgttatgcgg attctggata ttaggctgtt      300
tttttttttt tttttaatc gattgaagga tgtcaattta tagattgggc tgtagattgc      360
tagtttatgt cattgatatt gaattgtaag tttttcgatc ttccagtcat acaaatcact     420
aattgcctca agataggaaa atccattggc agtatataga tggagttcat atcttaagca    480
caggtttata tggtcattac atttctagct tttgtttgtt aggactgatt catgttgggt    540
ttttggggtt attctttata acgggtcatg cttgtatata tgtagtatca atacatttct    600
gatttgtggt tatgcttgat gcaaaaaaga tccaatcttt cgagttggta gtgagttaca   660
tttgttactt ttggtag                                                     677
```